(12) United States Patent
Lai et al.

(10) Patent No.: US 10,407,438 B2
(45) Date of Patent: Sep. 10, 2019

(54) CRYSTALLINE FORMS OF DARUNAVIR

(71) Applicant: Gilead Sciences, Inc., Foster City, CA (US)

(72) Inventors: Chiajen Lai, Livermore, CA (US); Bing Shi, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/793,684

(22) Filed: Oct. 25, 2017

(65) Prior Publication Data

US 2018/0170945 A1 Jun. 21, 2018

Related U.S. Application Data

(60) Provisional application No. 62/413,601, filed on Oct. 27, 2016.

(51) Int. Cl.
| | | |
|---|---|---|
| *C07D 493/04* | (2006.01) | |
| *A61K 31/34* | (2006.01) | |
| *A61P 31/18* | (2006.01) | |

(52) U.S. Cl.
CPC ............ *C07D 493/04* (2013.01); *A61P 31/18* (2018.01); *C07B 2200/13* (2013.01)

(58) Field of Classification Search
CPC .............................. C07D 493/04; A61K 31/34
See application file for complete search history.

(56) References Cited

U.S. PATENT DOCUMENTS

| | | | |
|---|---|---|---|
| 6,248,775 B1 | 6/2001 | Vazquez et al. | |
| 7,126,015 B2 | 10/2006 | Kesteleyn et al. | |
| 7,470,506 B1 | 12/2008 | Erickson et al. | |
| 7,595,408 B2 | 9/2009 | Quaedflieg et al. | |
| 7,700,645 B2 | 4/2010 | Vermeersch et al. | |
| 7,772,411 B2 | 8/2010 | Goyvaerts et al. | |
| 7,959,408 B2 | 6/2011 | Belmonte | |
| RE42,889 E | 11/2011 | Vazquez et al. | |
| RE43,596 E | 8/2012 | Vazquez et al. | |
| RE43,802 E | 11/2012 | Vazquez et al. | |
| 8,518,987 B2 | 8/2013 | Vermeersch et al. | |
| 8,597,876 B2 | 12/2013 | Erickson et al. | |
| 8,703,980 B2 | 4/2014 | Vellanki et al. | |
| 8,921,415 B2 | 12/2014 | Marom | |
| 9,062,067 B2 | 6/2015 | Ahire et al. | |
| 9,175,005 B2 | 11/2015 | Parthasaradhi Reddy et al. | |
| 9,216,990 B2 | 12/2015 | Vellanki et al. | |
| 2007/0104740 A1 | 5/2007 | Voorspoels | |
| 2012/0148803 A1 | 6/2012 | Schleiermacher et al. | |
| 2012/0251826 A1 | 10/2012 | Vellanki et al. | |
| 2012/0288563 A1 | 11/2012 | Reddy et al. | |
| 2013/0195978 A1 | 8/2013 | Parthasarashi Reddy et al. | |
| 2014/0066638 A1 | 3/2014 | Ahire et al. | |
| 2015/0141382 A1 | 5/2015 | Kamat et al. | |
| 2015/0141383 A1 | 5/2015 | Phull et al. | |
| 2015/0203506 A1 | 7/2015 | Chivukula et al. | |
| 2015/0336980 A1 | 11/2015 | Vermeersch et al. | |

FOREIGN PATENT DOCUMENTS

| | | | | |
|---|---|---|---|---|
| CN | 102584844 | * | 7/2012 | ........... C07D 493/04 |
| CN | 102584844 B | | 7/2012 | |
| CN | 104744488 A | | 7/2015 | |
| IN | 10/2012 | | 3/2012 | |
| IN | 11/2012 | | 3/2012 | |
| IN | 06/2014 | | 2/2014 | |
| IN | 40/2015 | | 10/2015 | |
| IN | 14/2016 | | 4/2016 | |
| WO | WO-9506030 A1 | | 3/1995 | |
| WO | WO-2001046120 A1 | | 6/2001 | |
| WO | WO-2005063770 A1 | | 7/2005 | |
| WO | WO-2011048604 A2 | | 4/2011 | |
| WO | WO-2011051978 A2 | | 5/2011 | |
| WO | WO-2011083287 A2 | | 7/2011 | |
| WO | WO-2011145099 A1 | | 11/2011 | |
| WO | WO-2013114382 A1 | | 8/2013 | |
| WO | WO-2016/092525 A1 | | 6/2016 | |
| WO | WO-2018081292 A1 | | 5/2018 | |

OTHER PUBLICATIONS

Chen et al., (1997) "A Practical Method for the Preparation of α'-Chloroketones of N-Carbamate Protected-α-Aminoacids", Tetrahedron Letters, 38: 3175-78.

Evans, et al., (1985) "A Stereocontrolled Synthesis of Hydroxyethylene Dipeptide Isoteres Using Novel, Chiral Aminoalkyl Epoxides and γ-(Aminoalkyl) γ-Lactones", Journal of Organic Chemistry, 50: 4615-25.

Ghosh, et al., (1991) "Di(Z-Pyridyl) Carbonate Promoted Alkoxycarbonylation of Amines: A Convenient Synthesis of Functionalized Carbamates", Tetrahedron Letters, 32: 4251-54.

Ghosh, et al., (1992) "An Efficient Synthesis of Functionalized Urethanes from Azides", Journal of the Chemical Society, Chemical Communications, 1308-10.

Ghosh, et al., (1998) "Potent HIV Protease Inhibitors Incorporating High-Affinity P2-Ligands and (R)-(Hydroxyethlyamino) Sulfonamide Isostere", Bioorganic & Medicinal Chemistry Letters, 8: 687-90.

Indian Patent Application No. 1994/MUM/2012, Published on Feb. 7, 2014, "Pharmaceutical Composition of Darunavir", Malhotra, et al., Cipla Limited, (20 pages).

Indian Patent Application No. 2548/CHE/2009, Published on Mar. 16, 2012, "Processes for Preparation of Amorphous Darunavir", Jetti, et al., Matrix Laboratories Ltd., (11 pages).

Indian Patent Application No. 3027/MUM/2014, Published on Apr. 1, 2016, "Crystalline Form of Darunavir and Process for Preparing Thereof", Desai, et al., Cadila Healthcare Limited, (24 pages).

Indian Patent Application No. 3106/CHE/2009, Published on Mar. 9, 2012, "Novel Crystalline Form of Darunavir and Process for its Preparation", Jetti, et al., Matrix Laboratories Ltd., (13 pages).

Indian Patent Application No. 999/MUM/2014, Published on Oct. 2, 2015, Solvates of Hiv Protease Inhibitor and Processes for Preparation Thereof, Singh, et al., Lupin Limited, (8 pages).

International Search Report for PCT International Application No. PCT/US2017/058325, dated Mar. 19, 2018, (10 Pages).

Kanemitsu, et al., (2016) "A Concise One-Pot Organo- and Biocatalyzed Preparation of Enantiopure Hexahydrofuro[2,3-b]furan-3-ol: An Approach to the Synthesis of HIV Protease Inhibitors", European Journal of Organic Chemistry, 1874-80.

Luly, et al., (1987) "A Synthesis of Protected Aminoalkyl Epoxides from α-Amino Acids", Journal of Organic Chemistry, 52: 1487-92.

* cited by examiner

*Primary Examiner* — Irina Neagu

(57) ABSTRACT

The present invention relates to novel crystalline forms of darunavir, the pharmaceutical formulations, and the therapeutic uses thereof in treating viral infections.

13 Claims, 42 Drawing Sheets

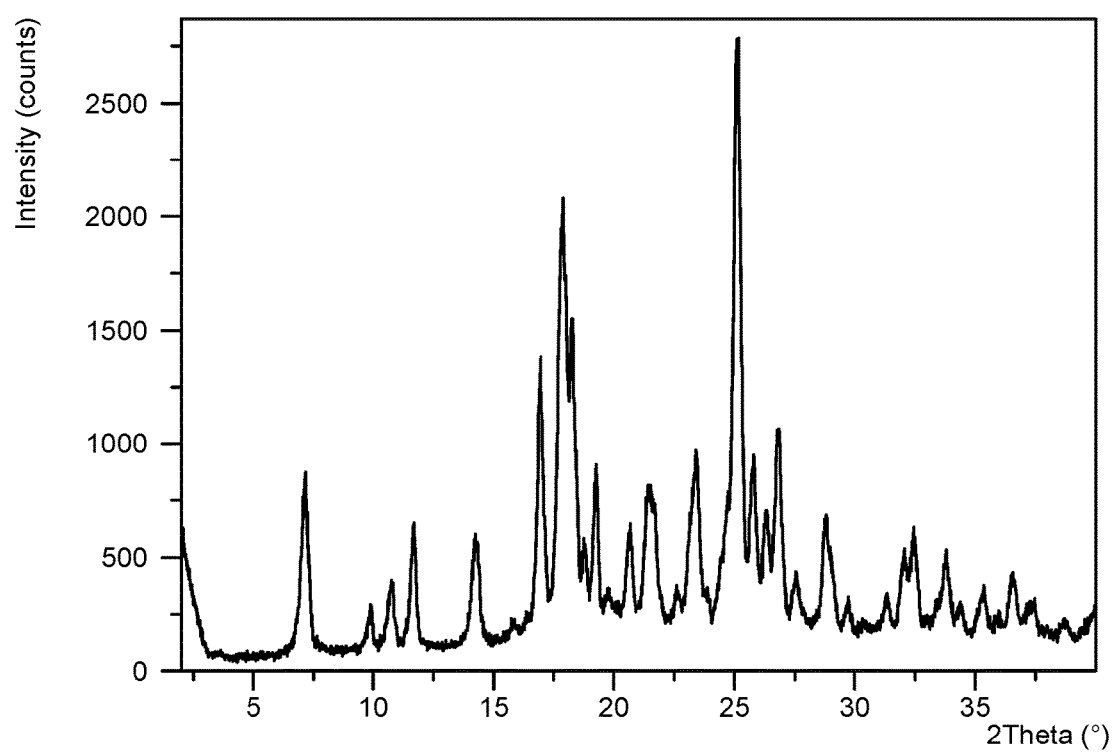
FIG. 1: XRPD pattern for Formula I Form I

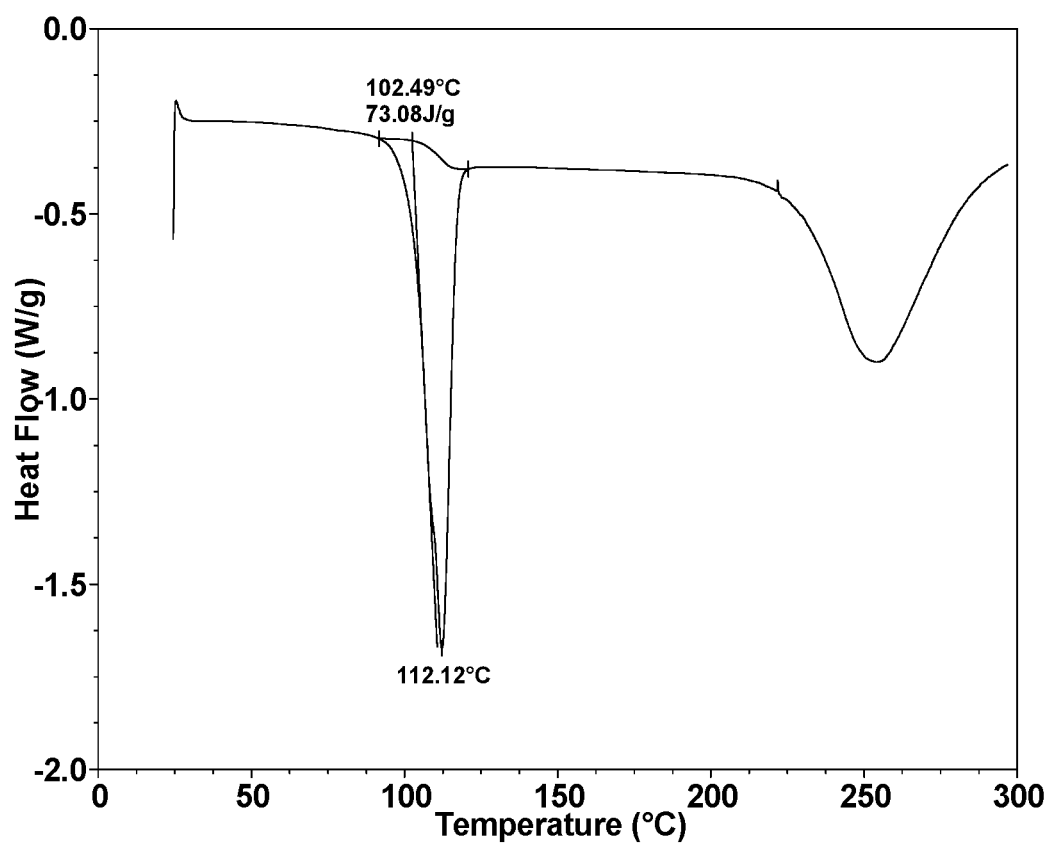
FIG. 2: DSC for Formula I Form I

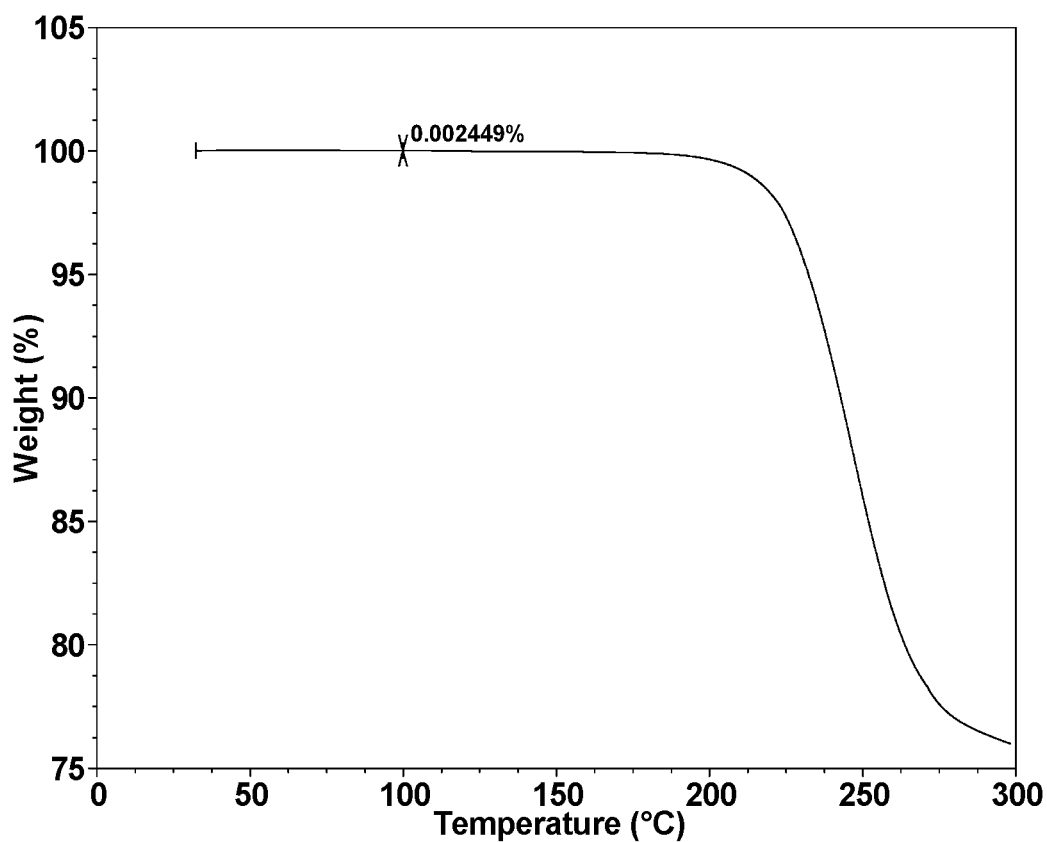
FIG. 3: TGA for Formula I Form I

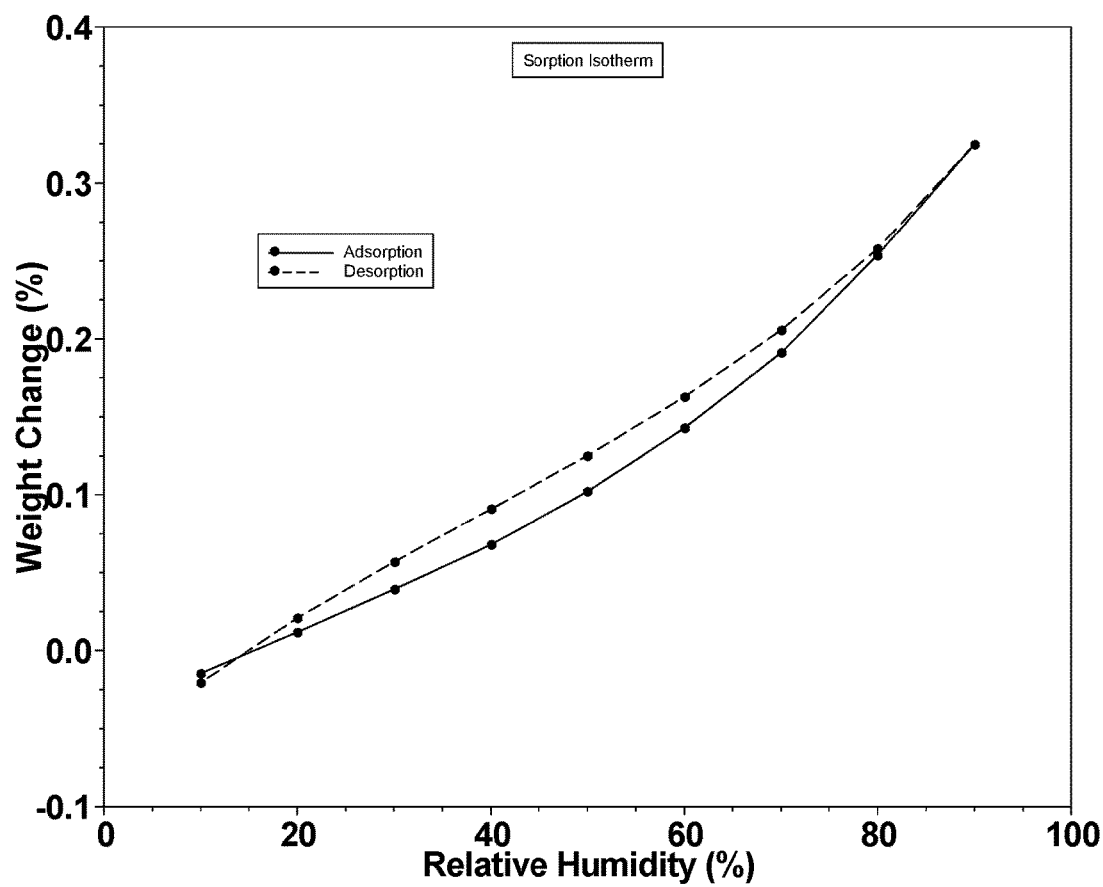
FIG. 4: DVS for Formula I Form I

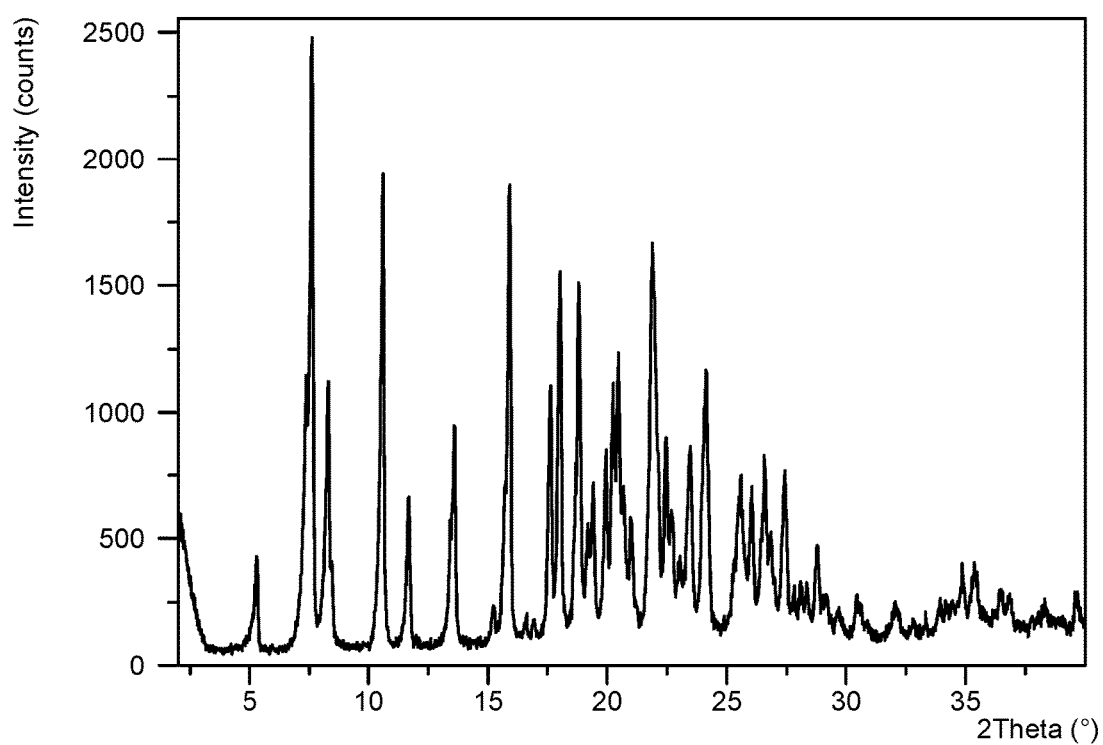
FIG. 5: XRPD pattern for Formula I Hydrate I

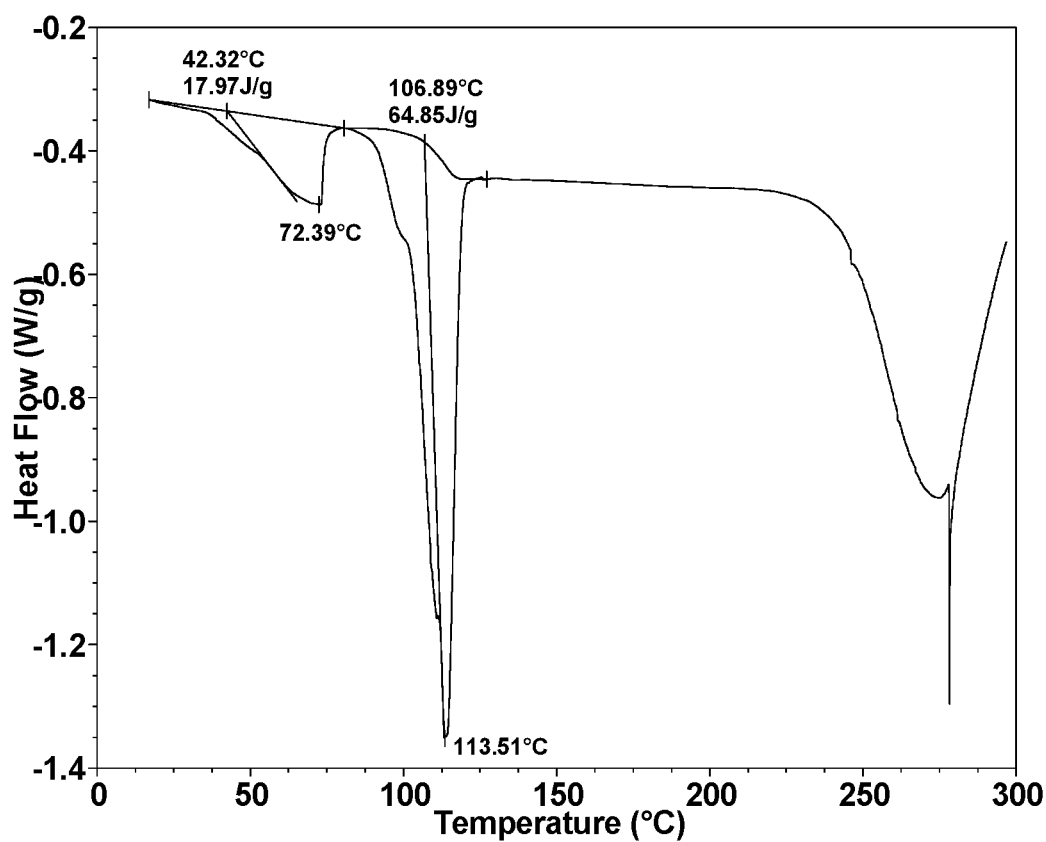
FIG. 6a: DSC for Formula I Hydrate I

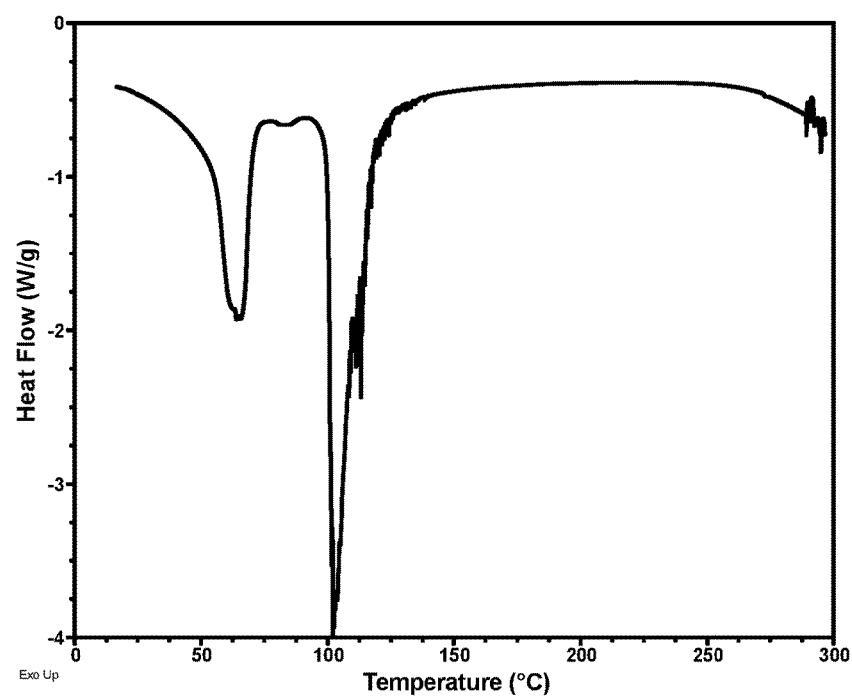
FIG. 6b - DSC thermogram of Formula I, Hydrate I with approximately 6 equiv water

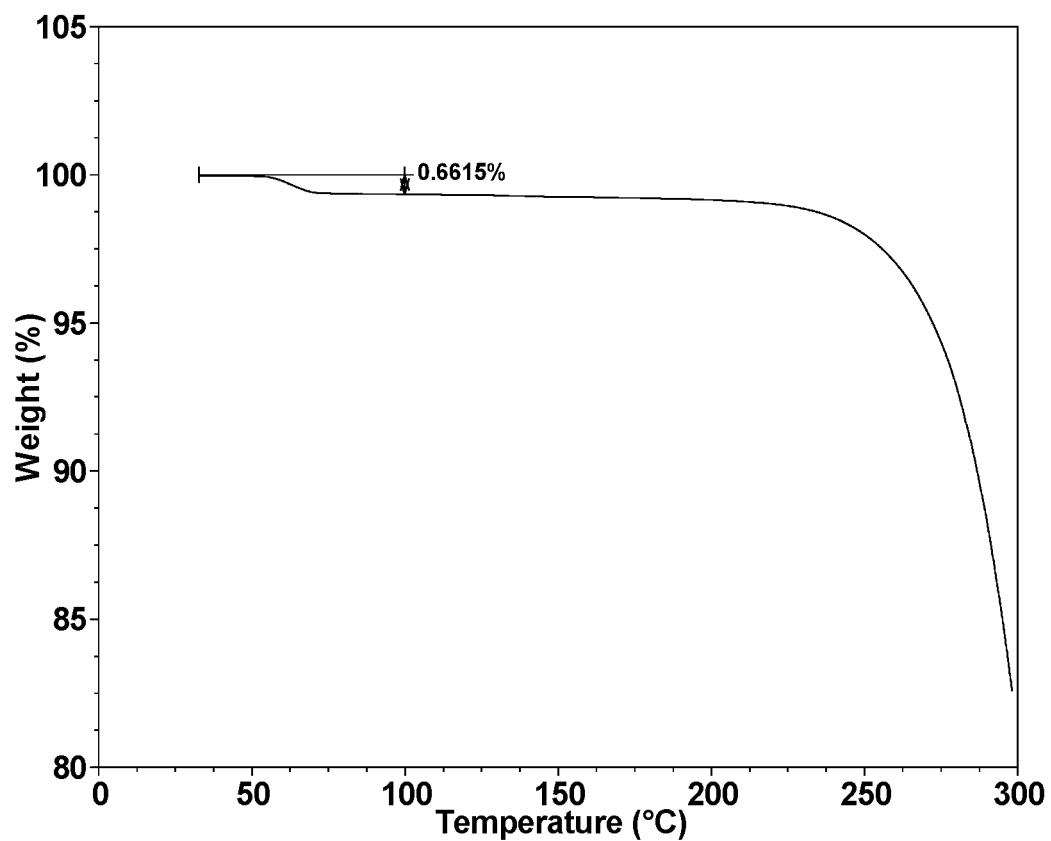
FIG. 7a: TGA for Formula I Hydrate I

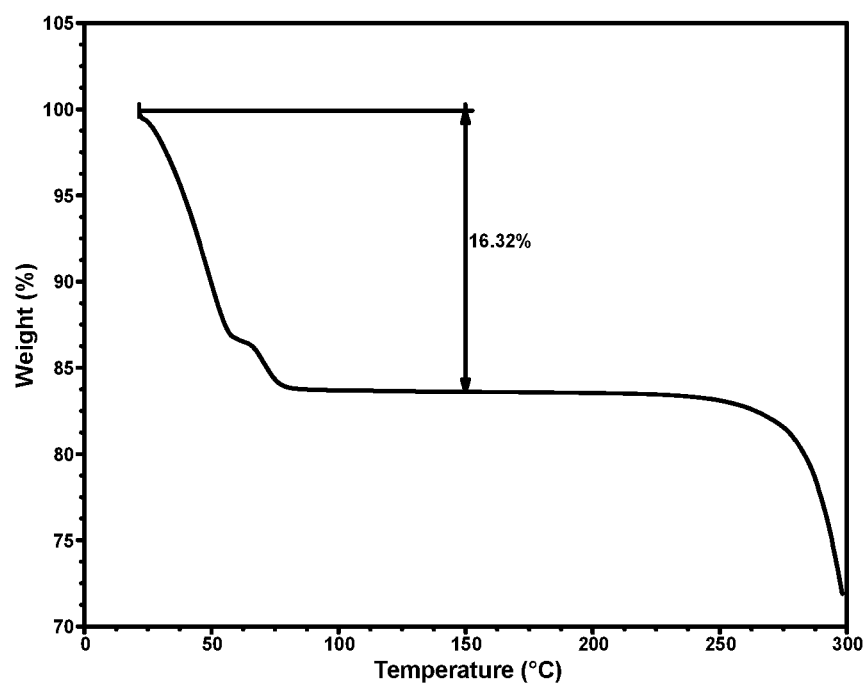
FIG. 7b - TGA thermogram of Formula I, Hydrate I with approximately 6 equiv water

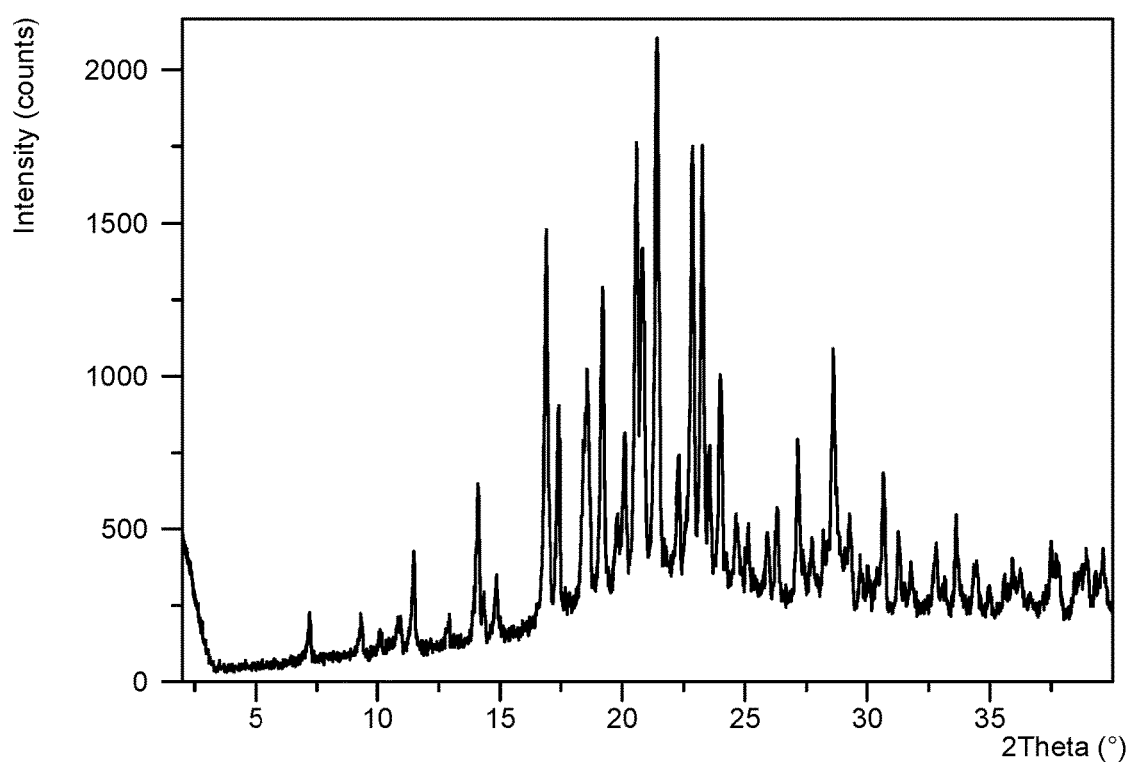
FIG. 8: XRPD pattern for Formula I Acetic Acid Solvate I

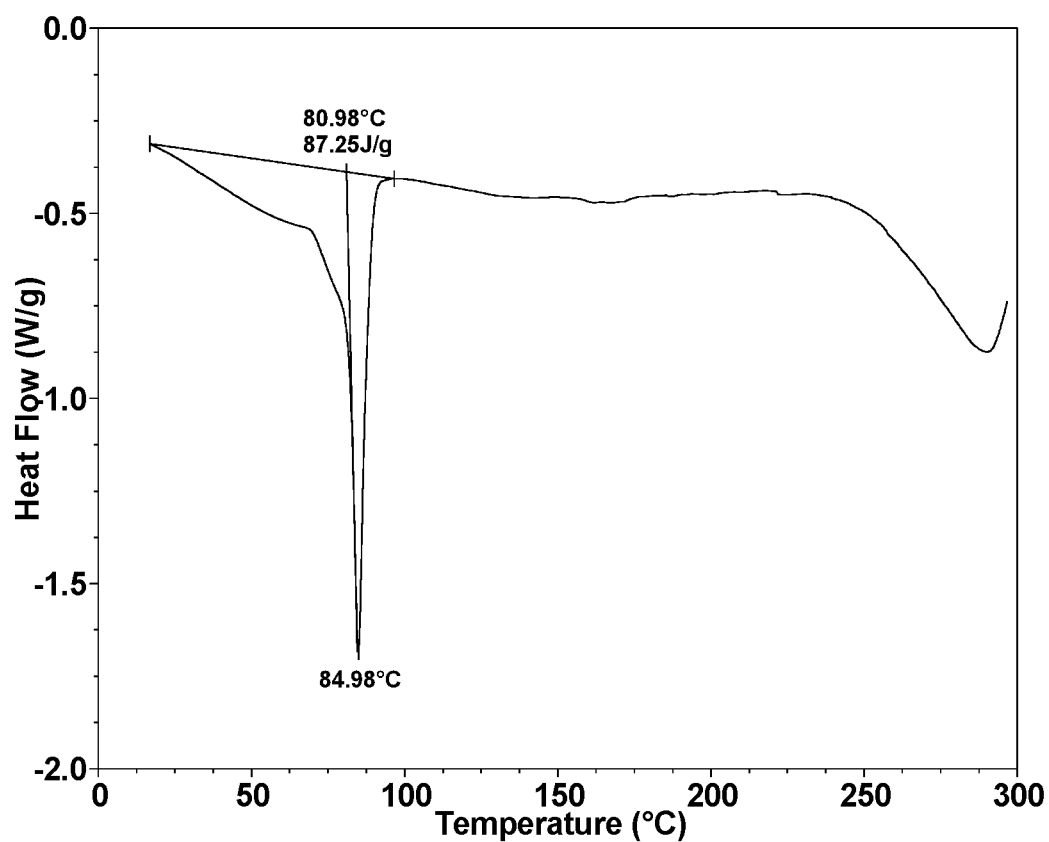
FIG. 9: DSC for Formula I Acetic Acid Solvate I

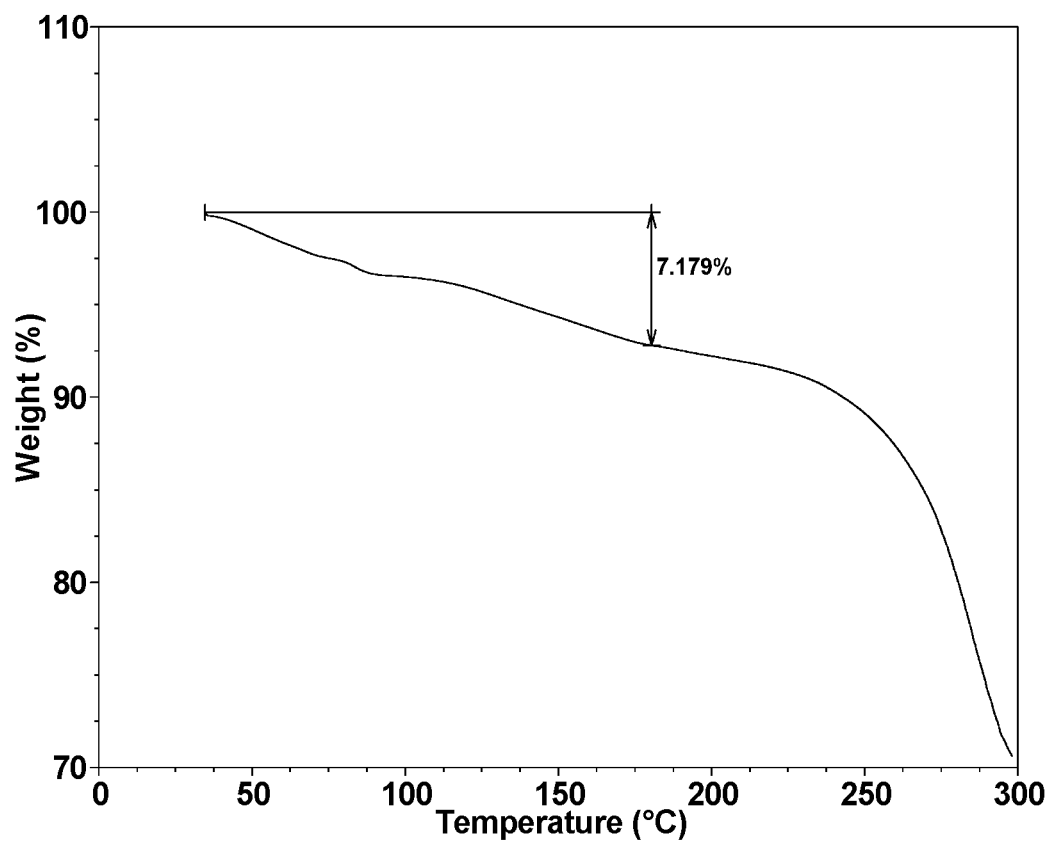
FIG. 10: TGA for Formula I Acetic Acid Solvate I

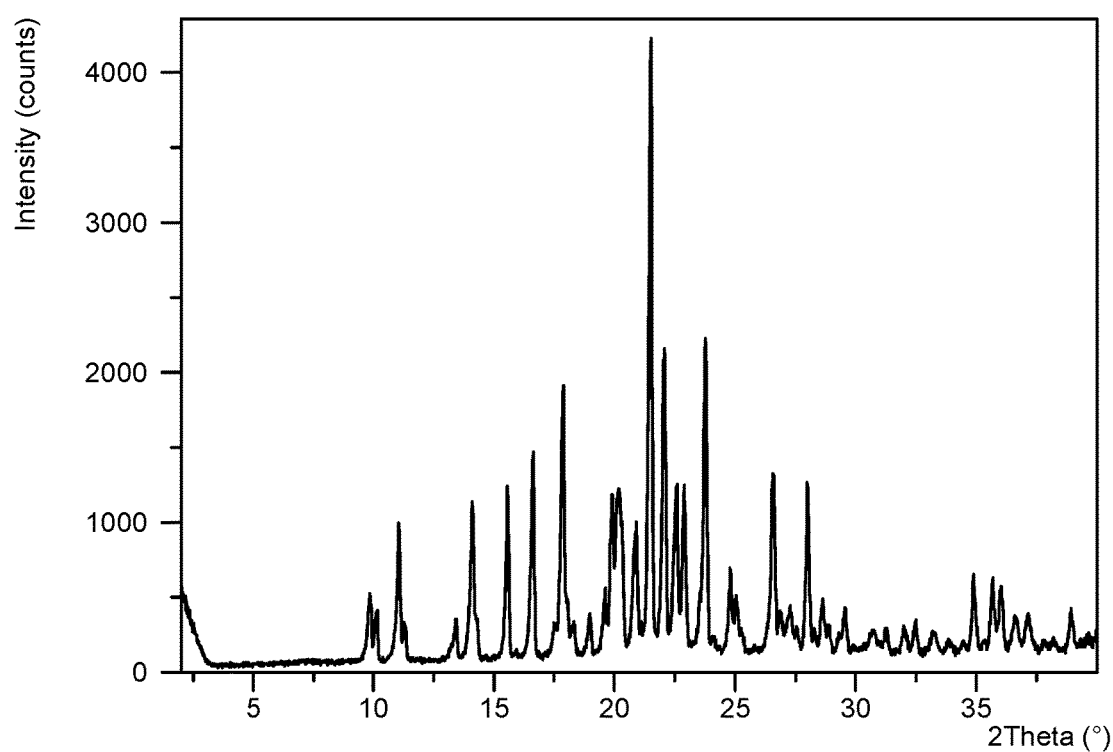
FIG. 11: XRPD pattern for Formula I Esylate I

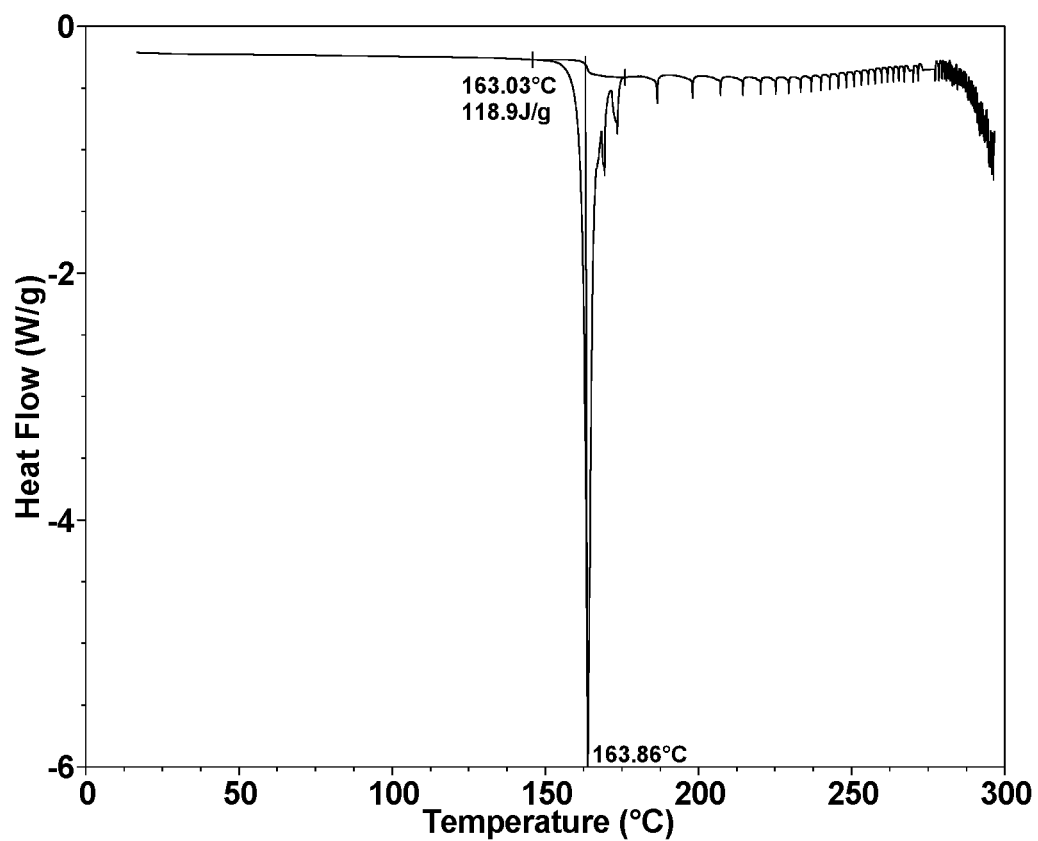
FIG. 12: DSC for Formula I Esylate I

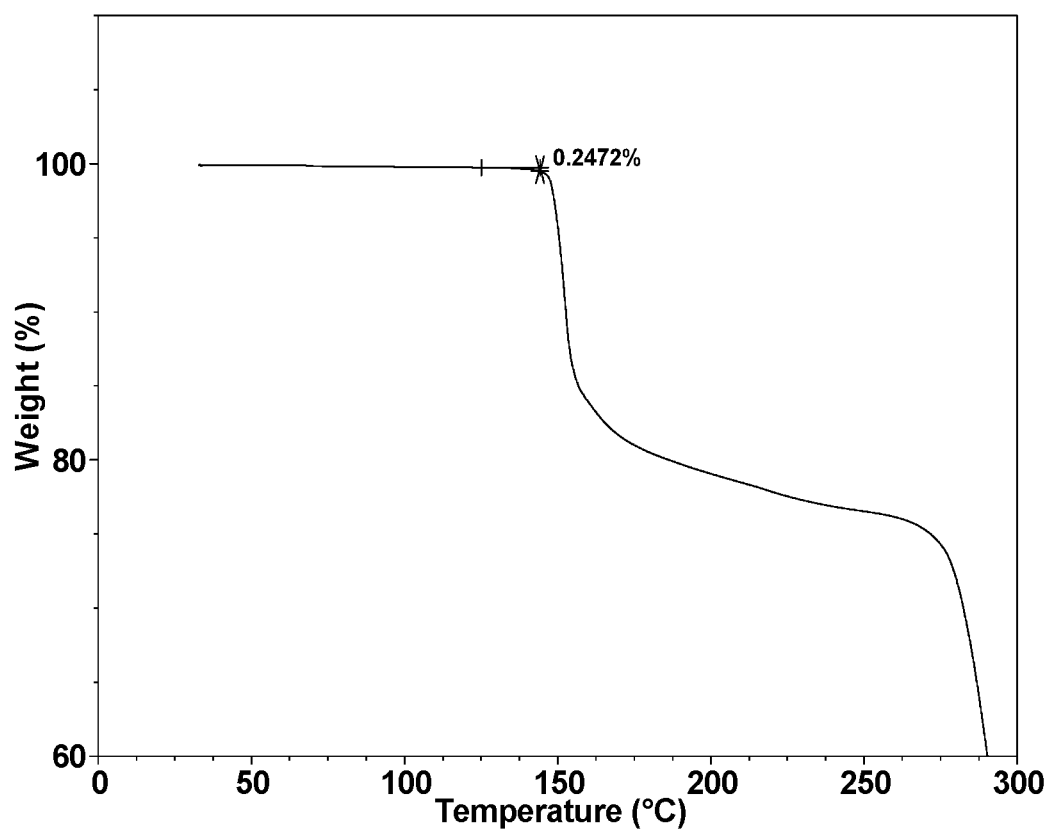
FIG. 13: TGA for Formula I Esylate I

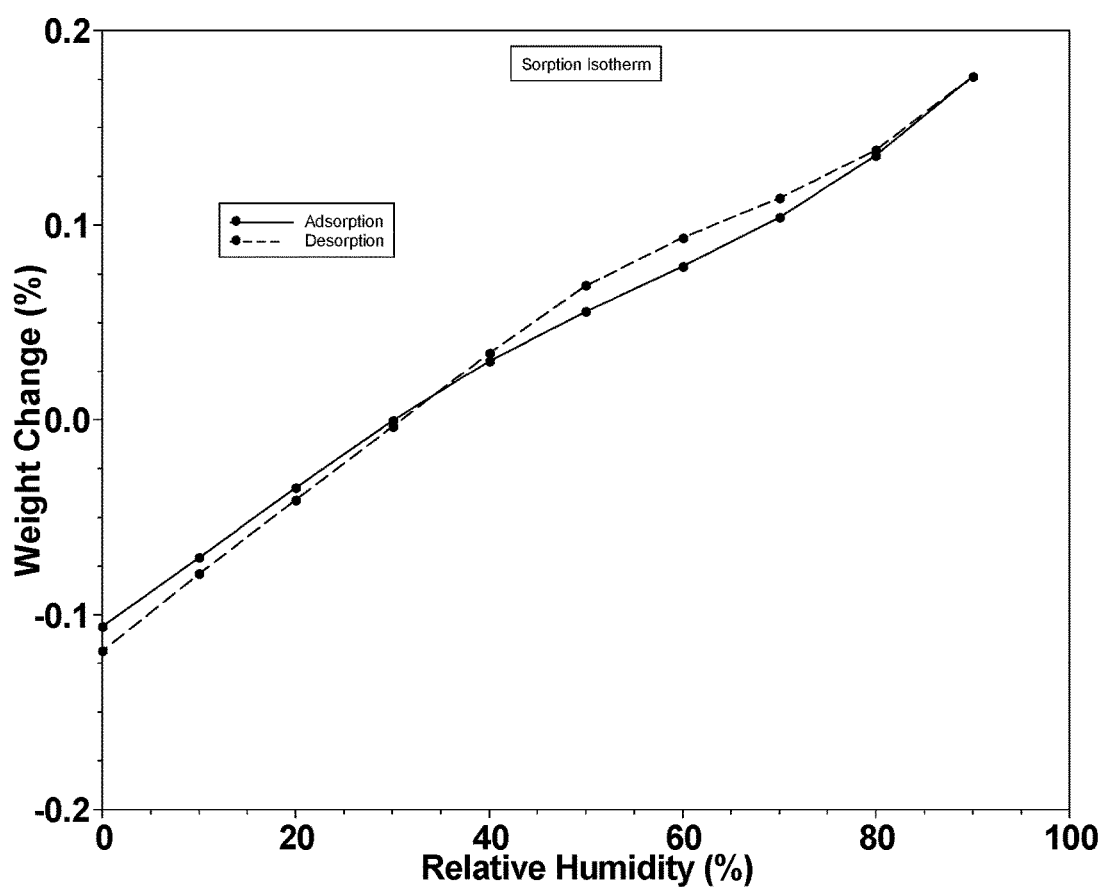
FIG. 14: DVS for Formula I Esylate I

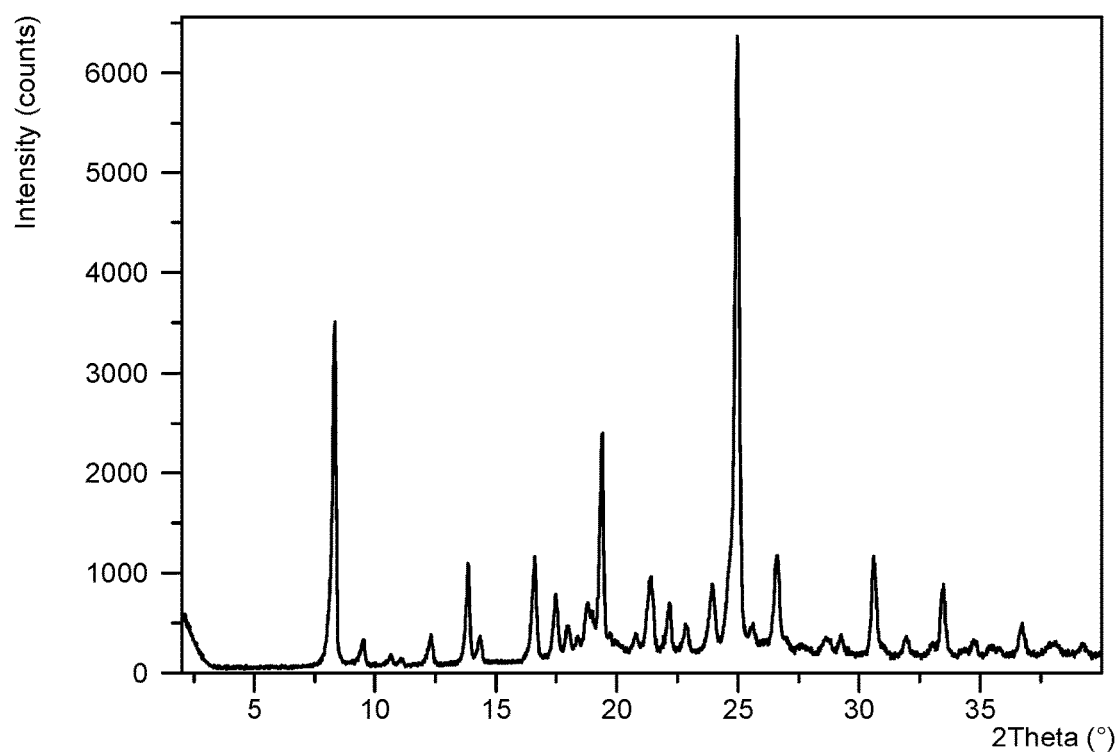
FIG. 15: XRPD pattern for Formula I Besylate I

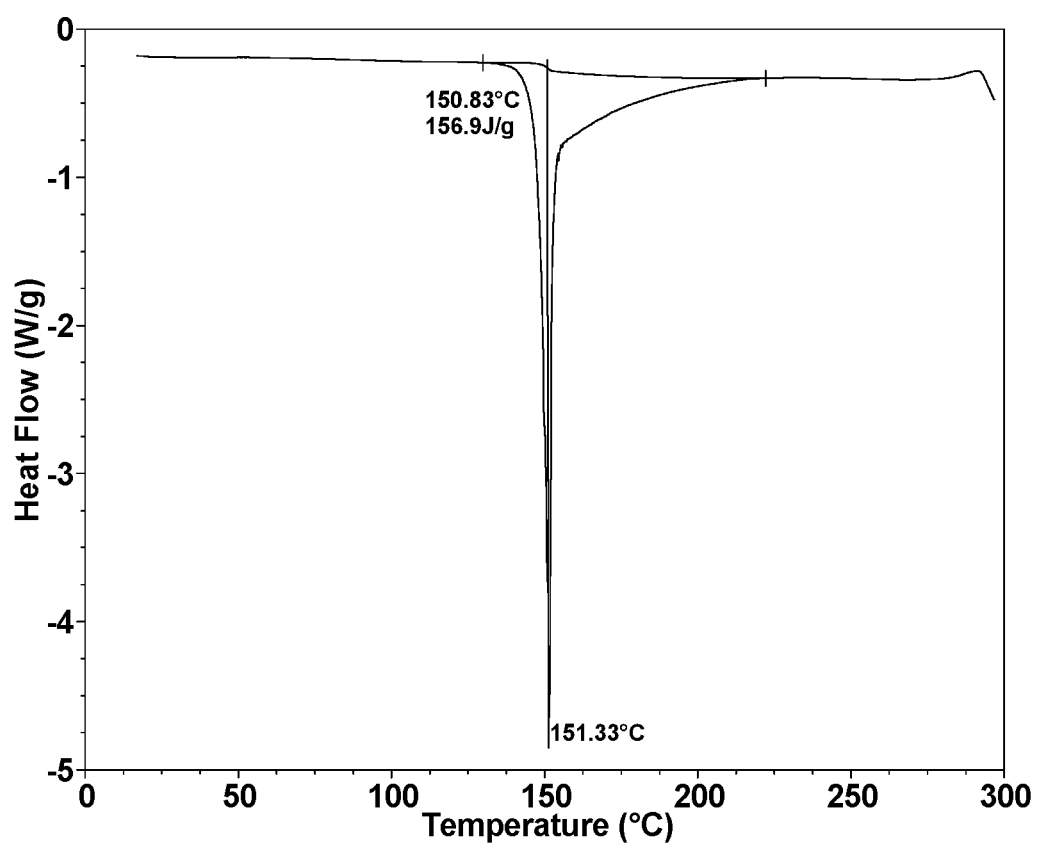
FIG. 16: DSC for Formula I Besylate I

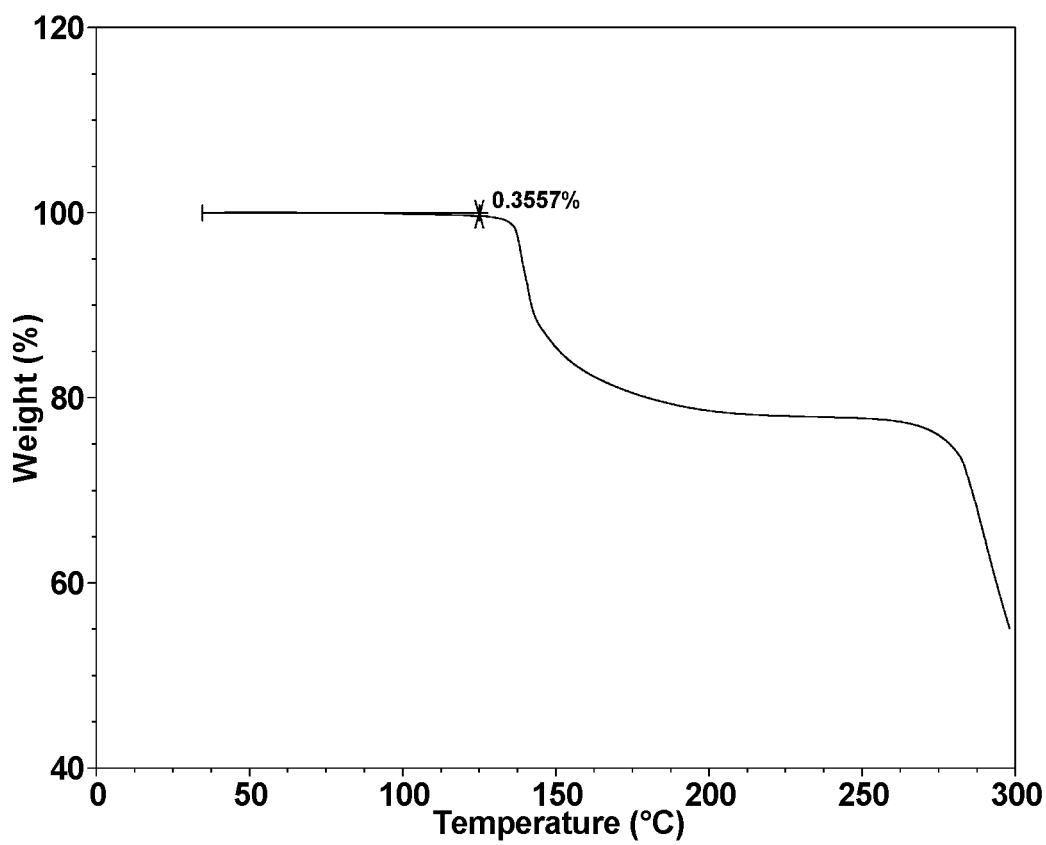
FIG. 17: TGA for Formula I Besylate I

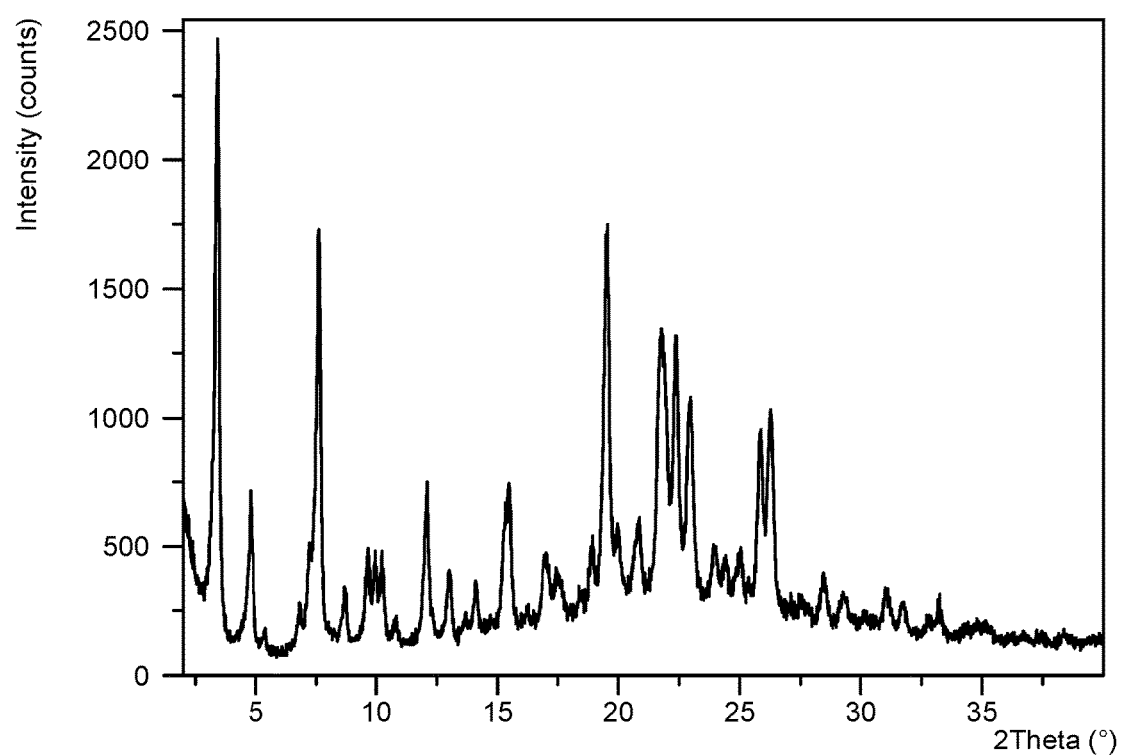
FIG. 18: XRPD pattern for Formula I Hemisulfate I

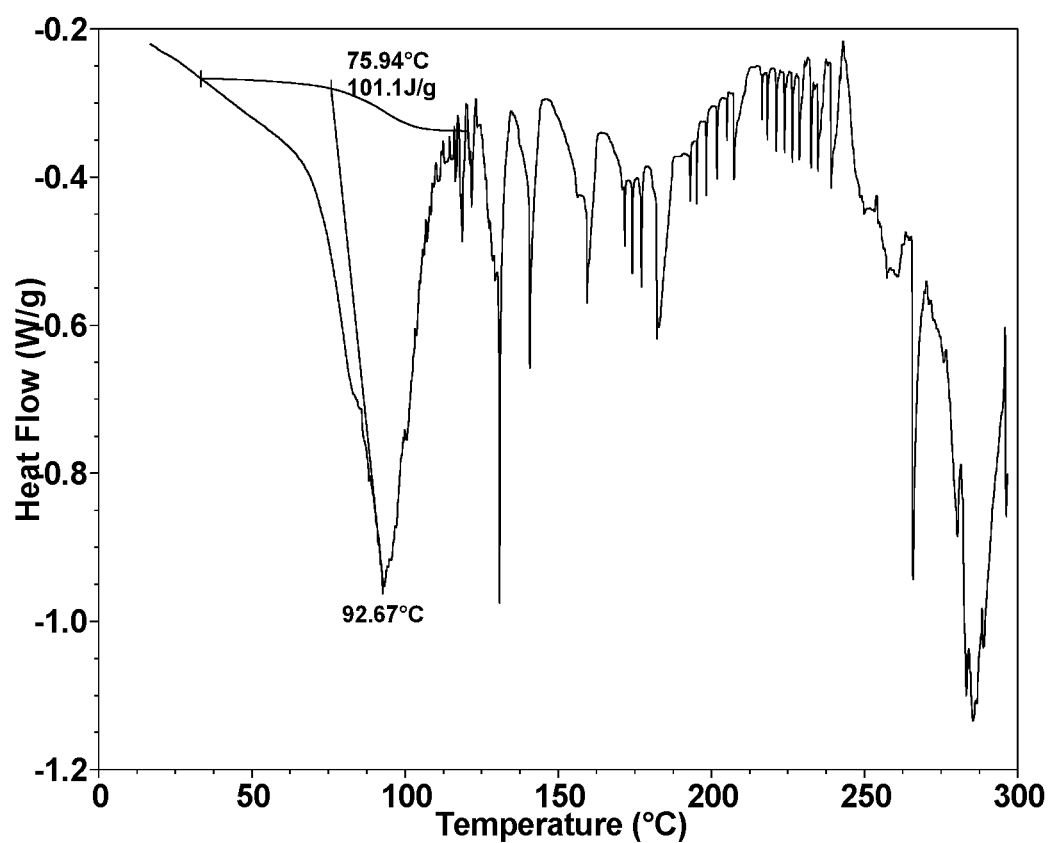
FIG. 19: DSC for Formula I Hemisulfate I

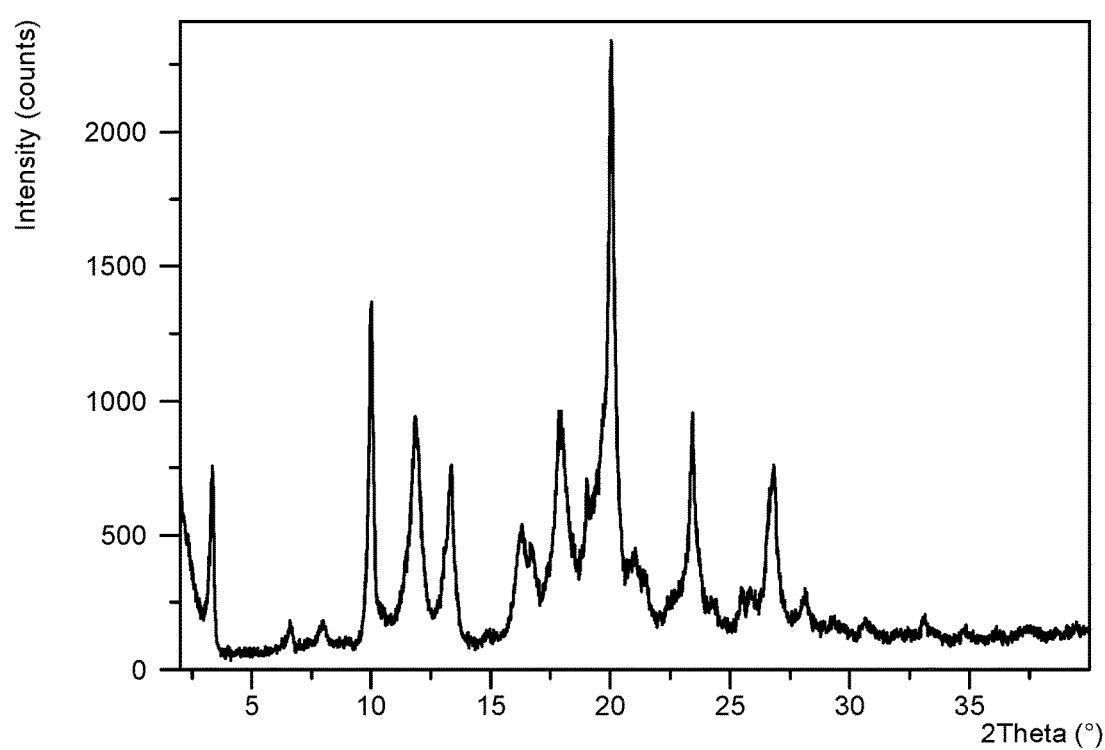
FIG. 20: XRPD pattern for Formula I Napsylate I

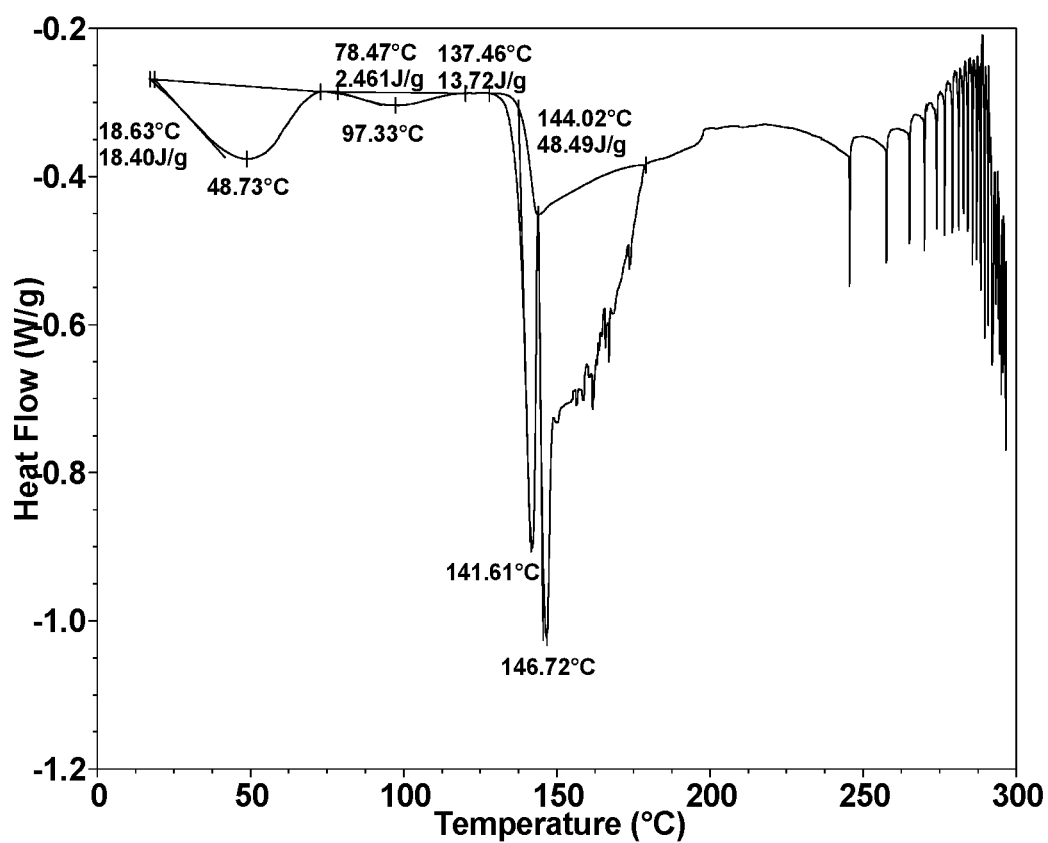
FIG. 21: DSC for Formula I Napsylate I

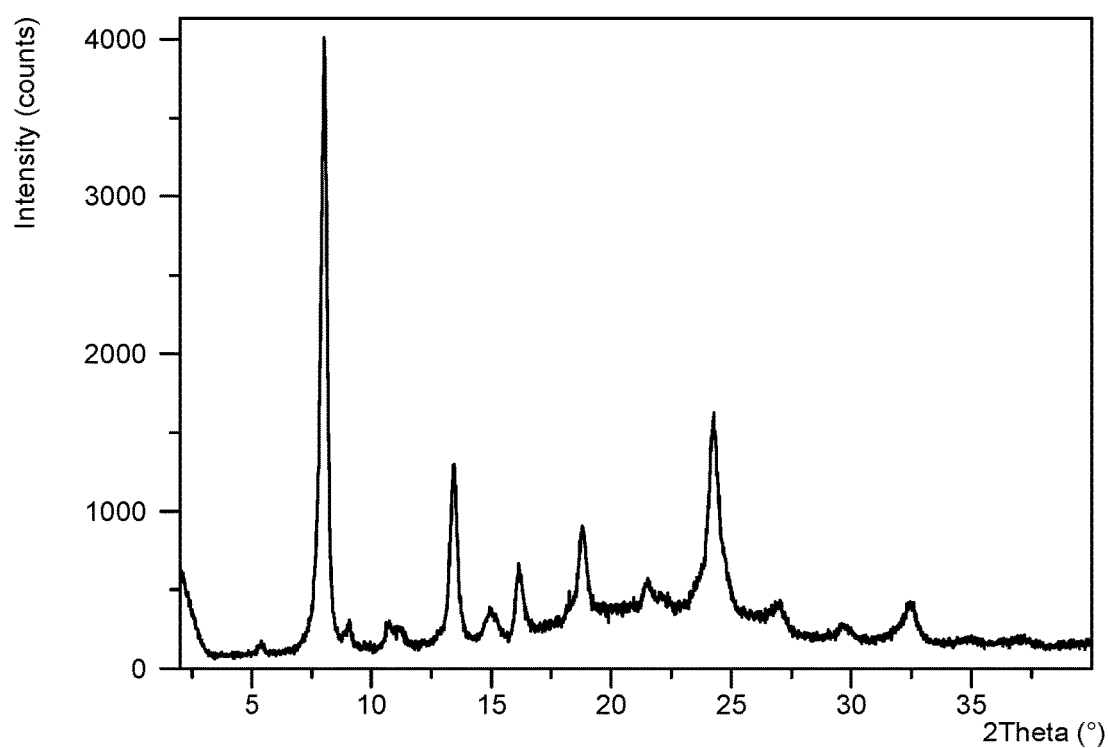
FIG. 22: XRPD pattern for Formula I Hemiedisylate I

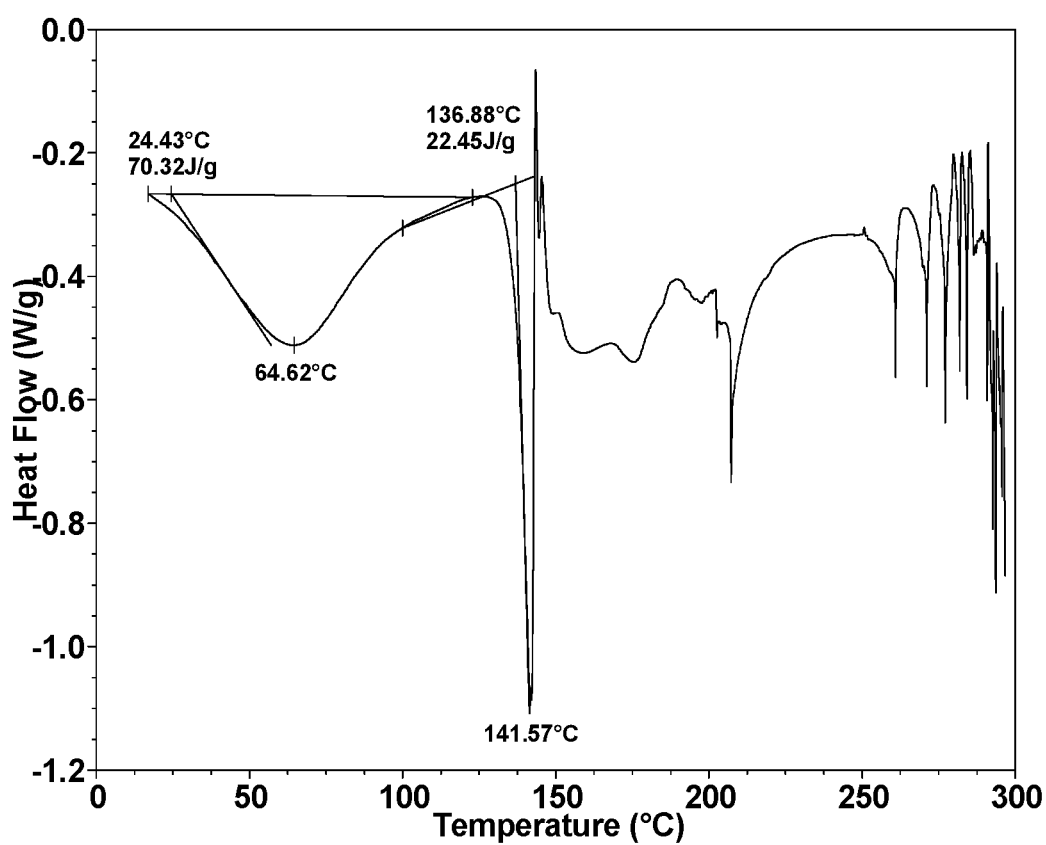
FIG. 23: DSC for Formula I Hemiedisylate I

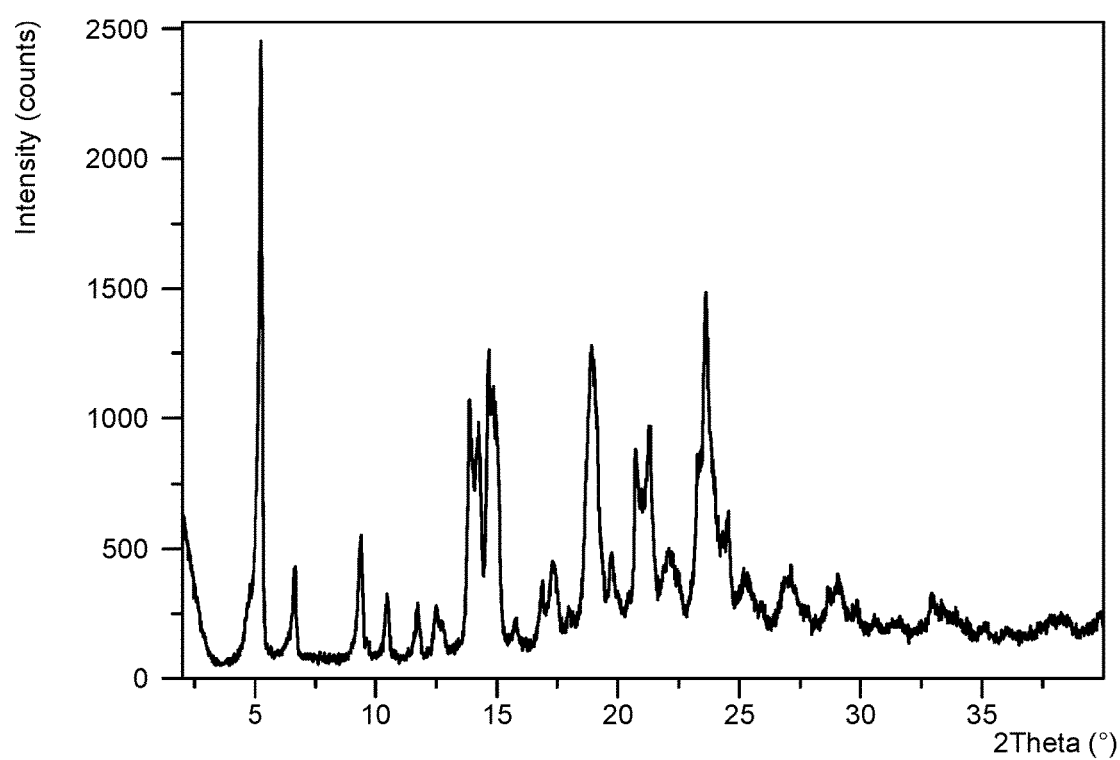
FIG. 24: XRPD pattern for Formula I Tosylate I

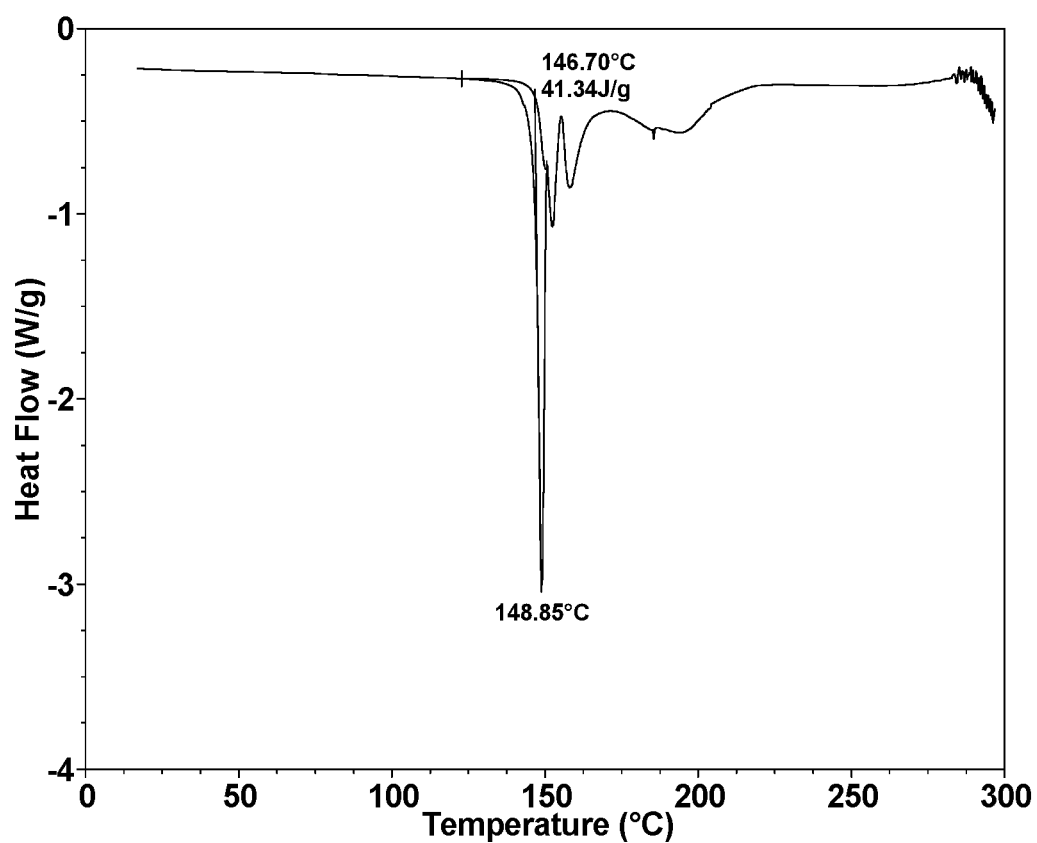
FIG. 25: DSC for Formula I Tosylate I

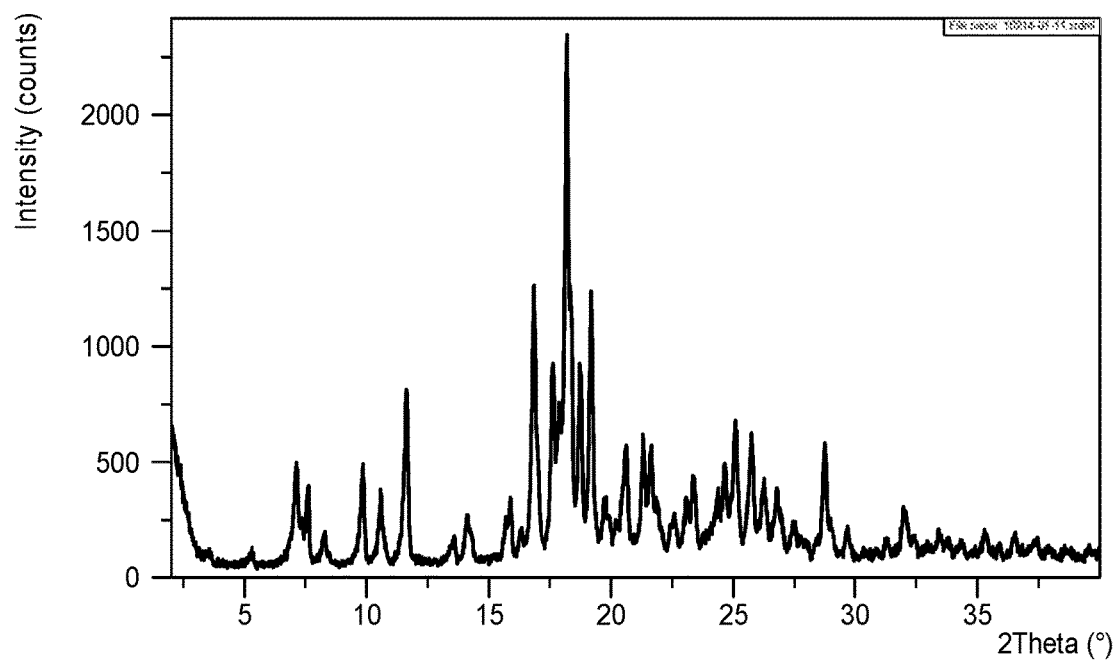
FIG. 26 - XRPD pattern of Formula I, Material A

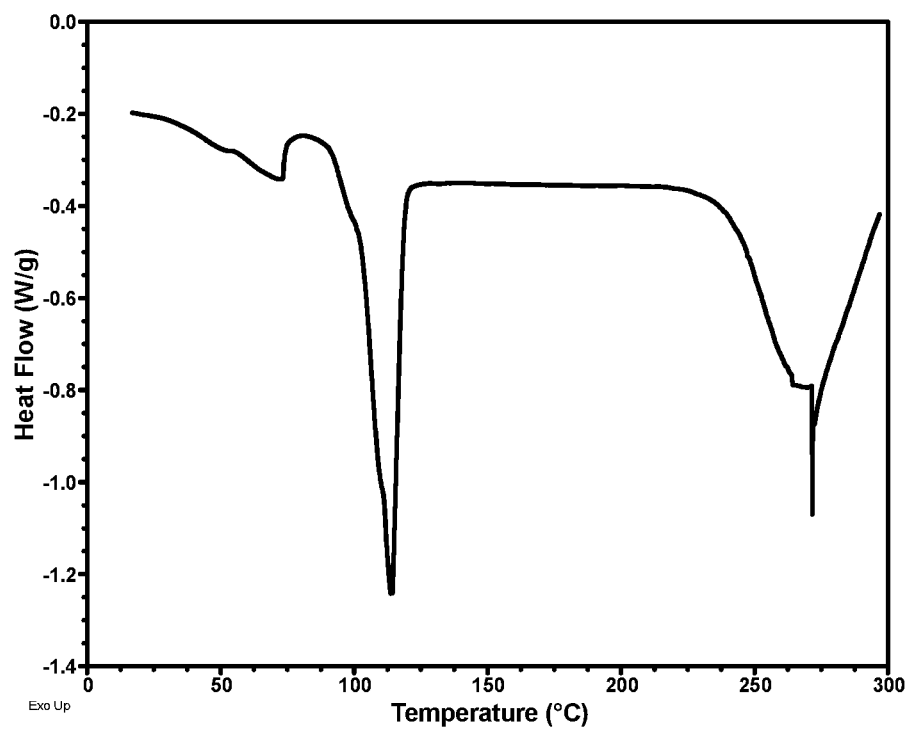
FIG. 27 - DSC thermogram of Formula I, Material A

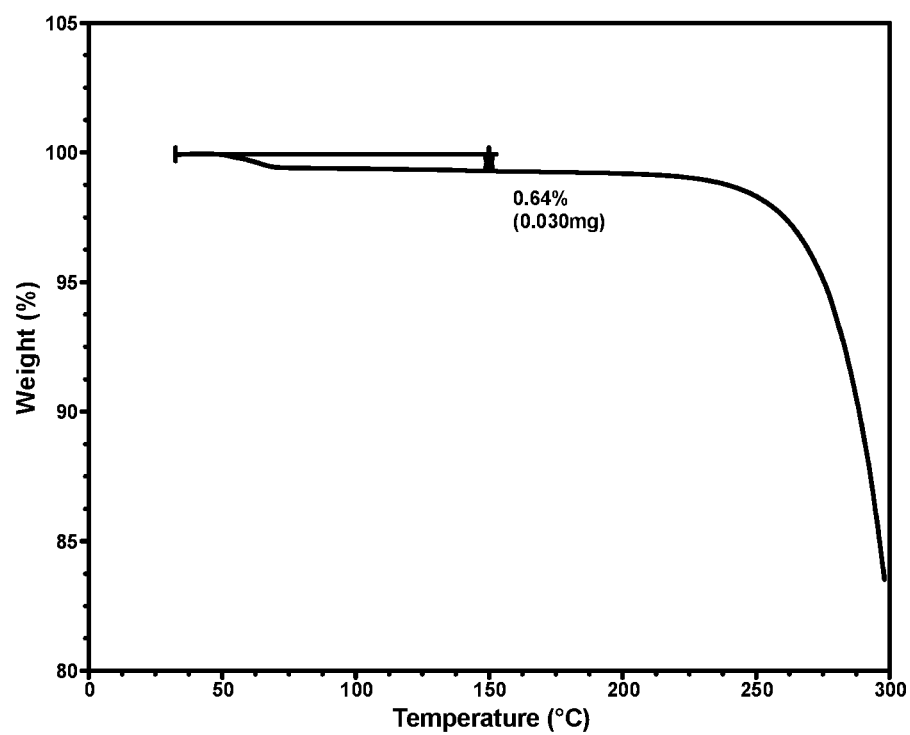
FIG. 28 - TGA thermogram of Formula I, Material A

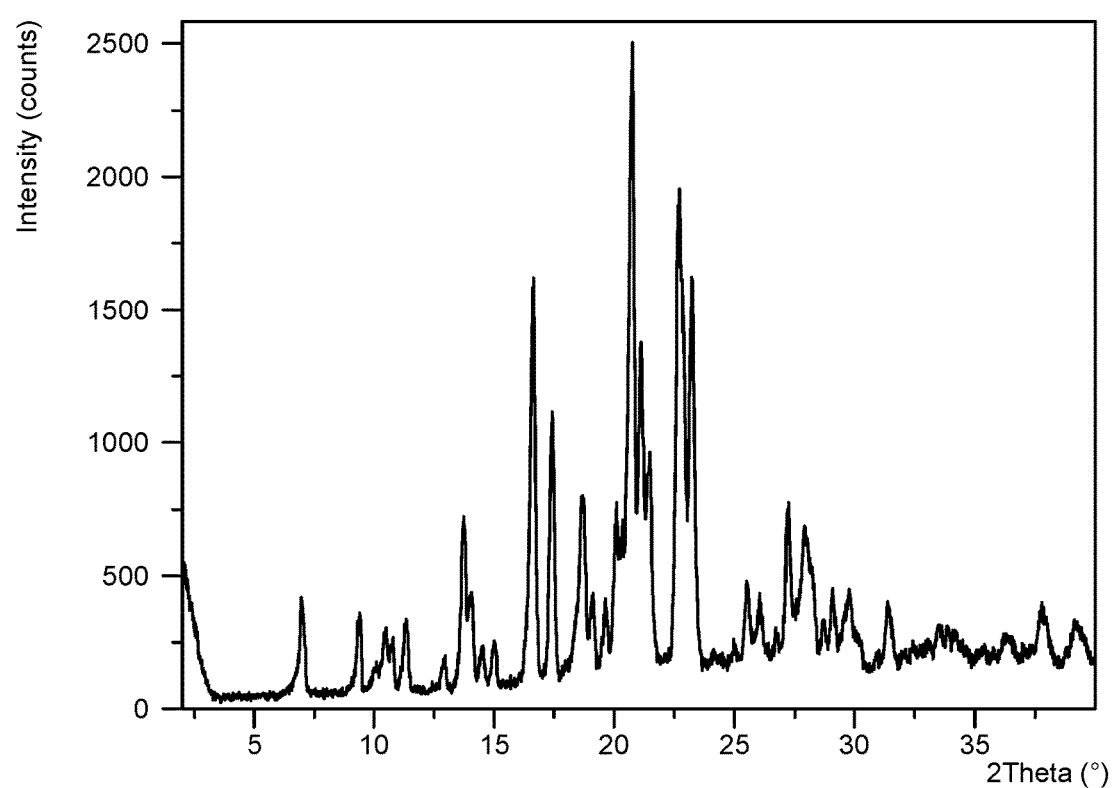
FIG. 29 - XRPD pattern of free base Formula I, MEK solvate

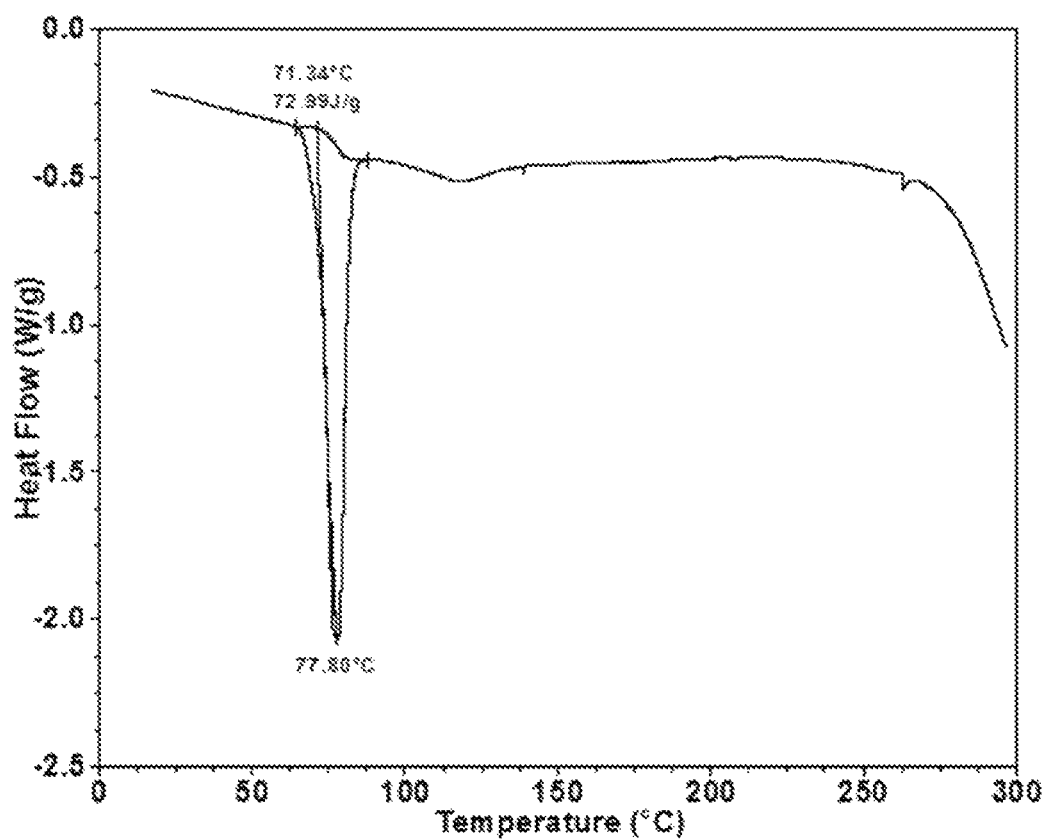
FIG. 30 - DSC thermogram of free base Formula I, MEK, solvate

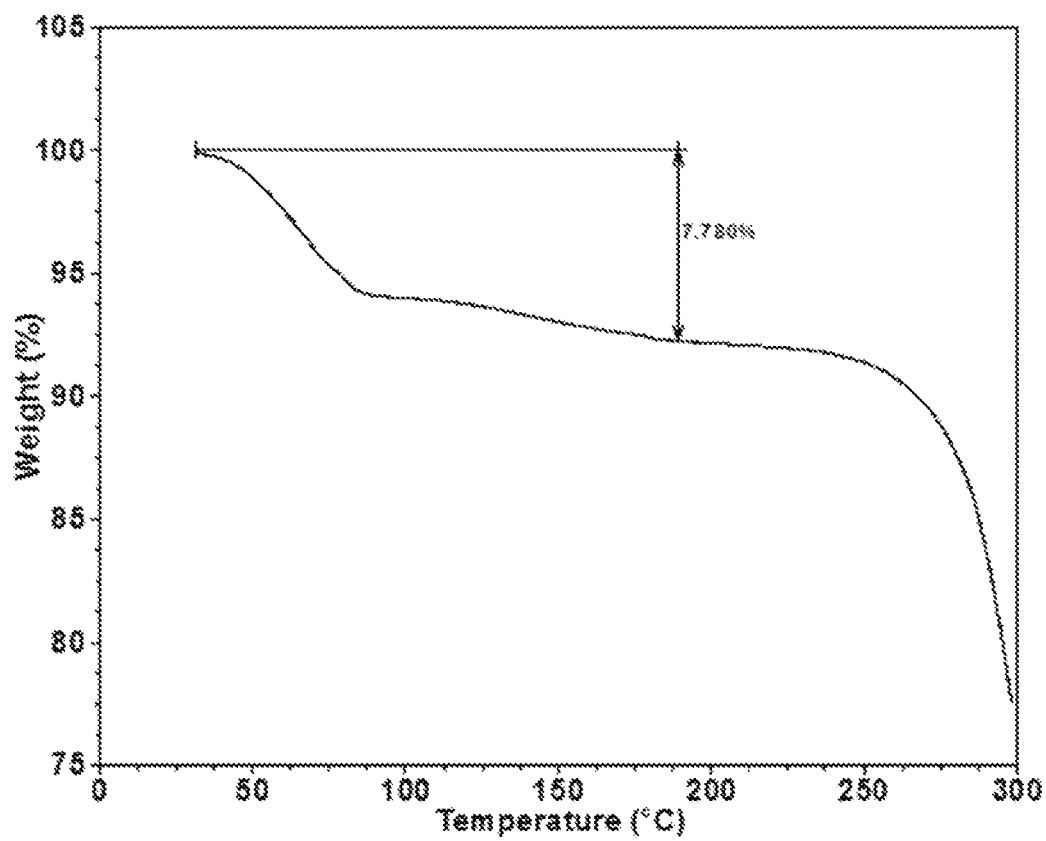
FIG. 31 - TGA thermogram of free base Formula I, MEK solvate

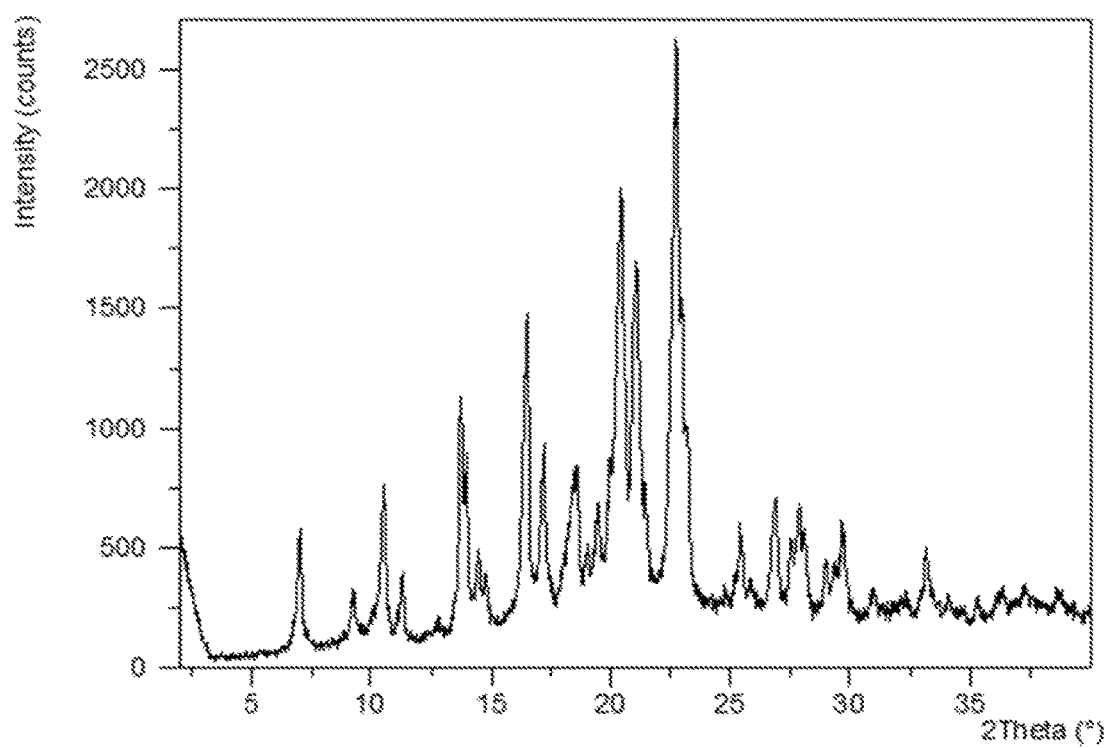
FIG. 32 - XRPD pattern of free base Formula I, MeTHF solvate

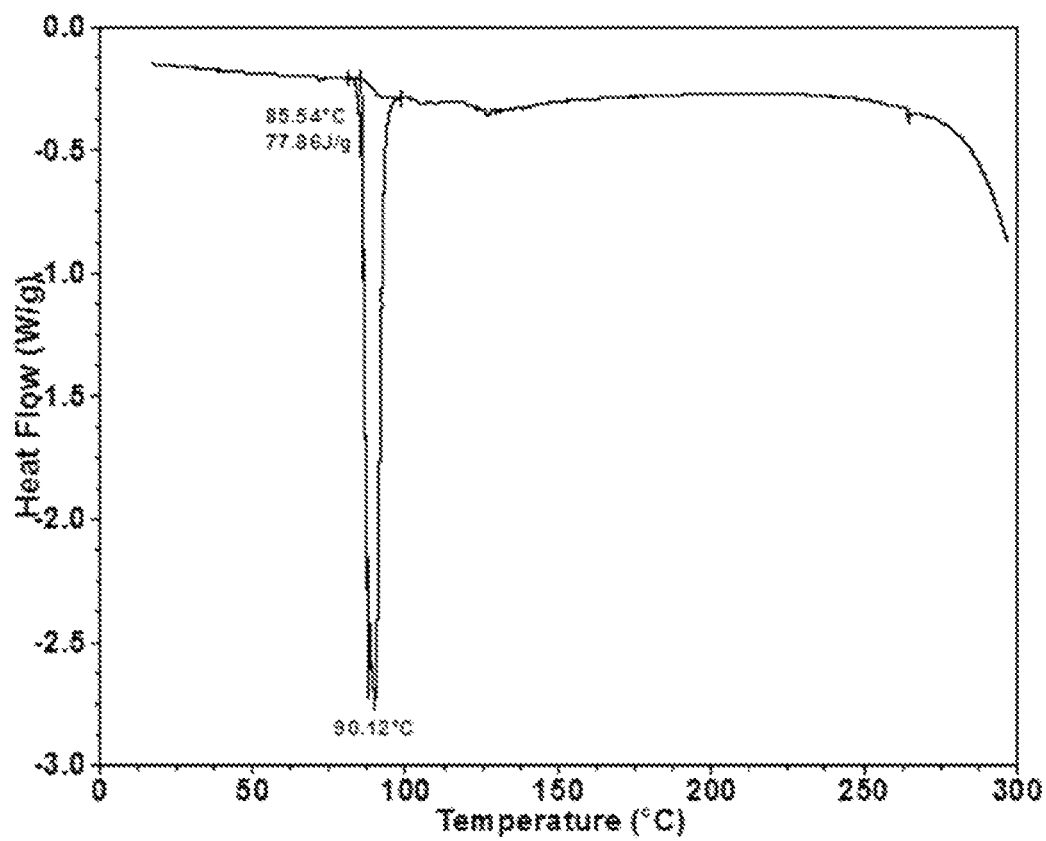
FIG. 33- DSC thermogram of free base Formula I, MeTHF solvate

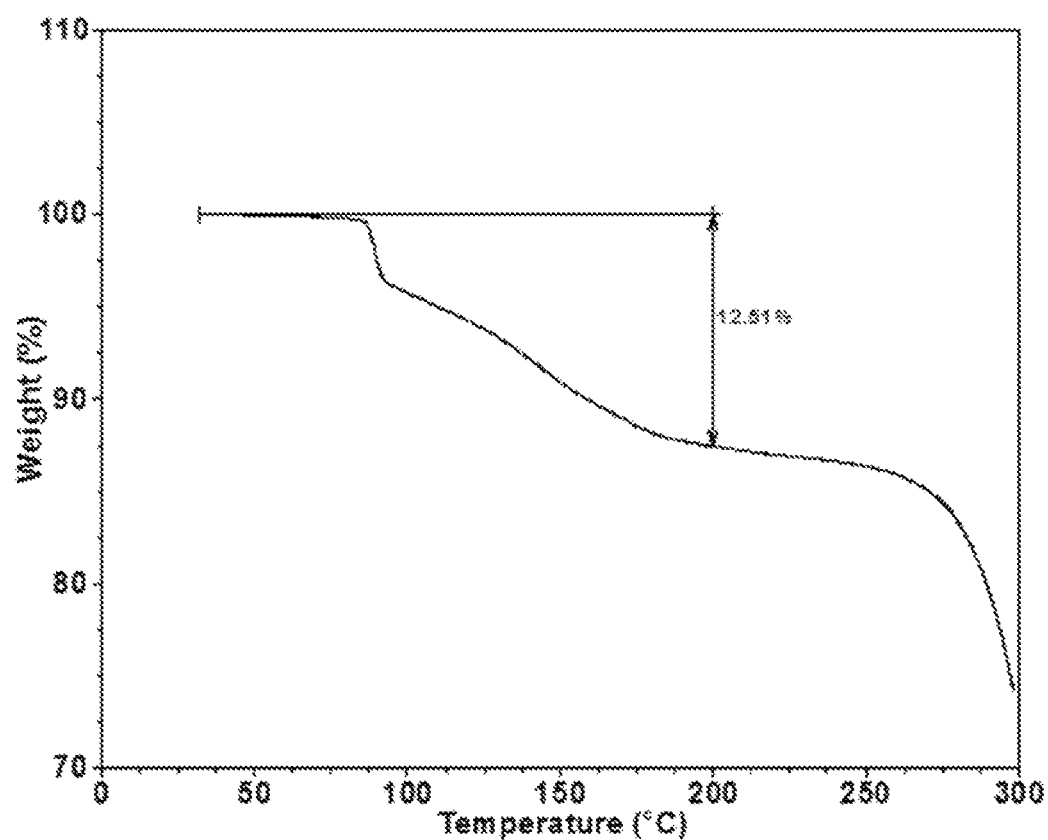
FIG. 34- TGA thermogram of free base Formula I, MeTHF solvate

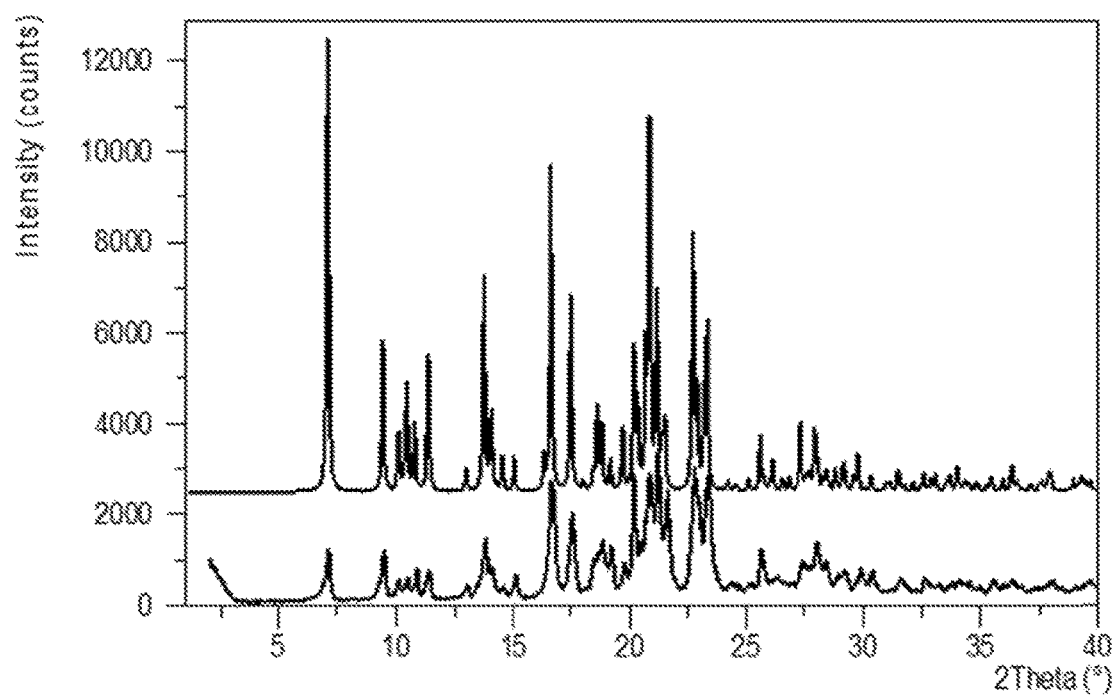
FIG. 35- XRPD pattern of Formula I, MeOAc solvate

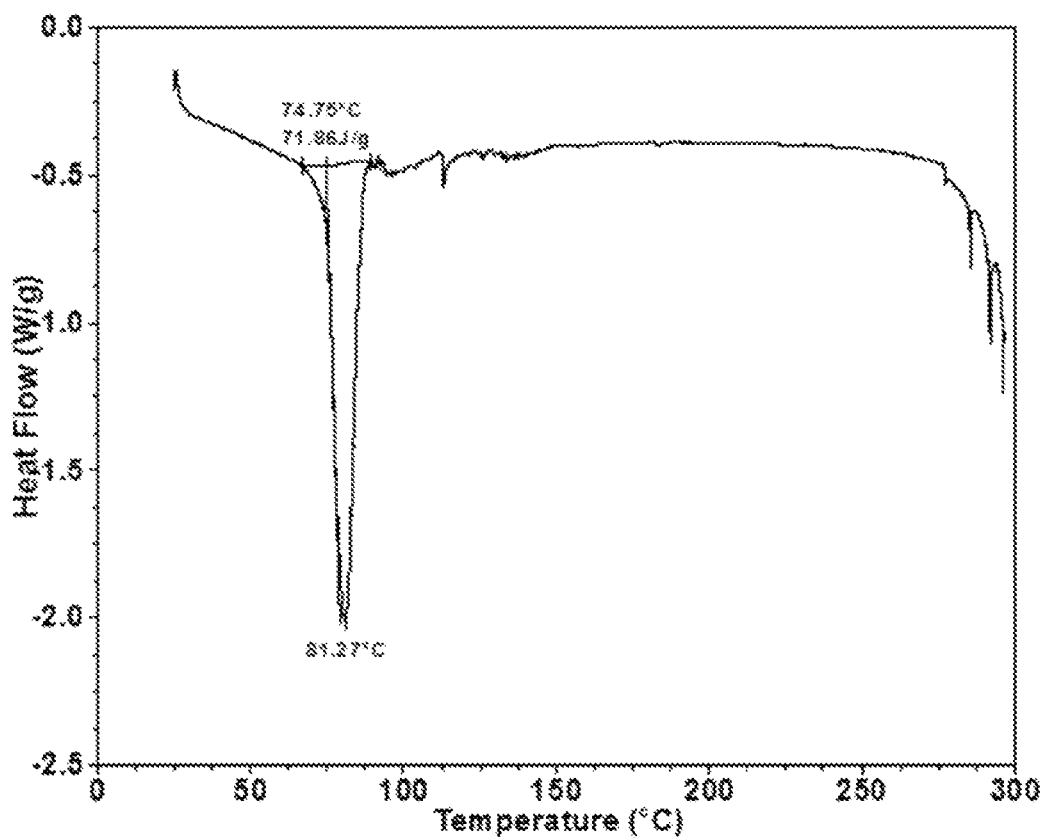
FIG. 36 - DSC thermogram of Formula I, MeOAc solvate

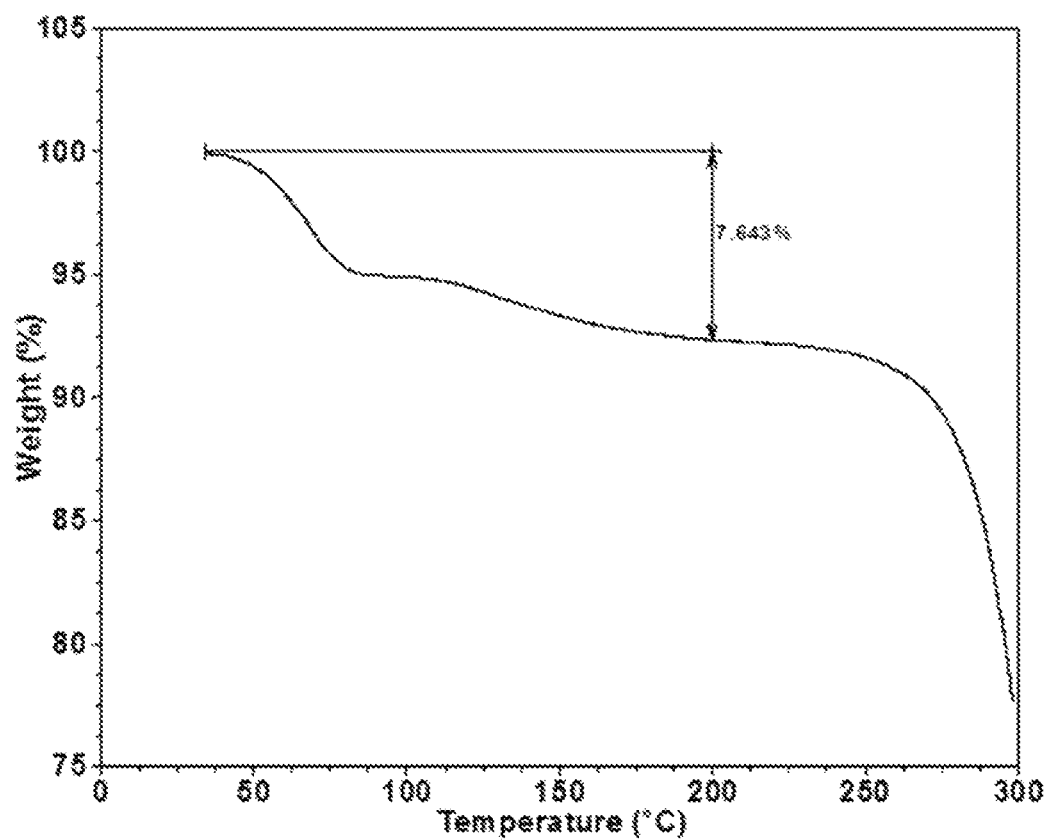
FIG. 37 - TGA thermogram of Formula I, MeOAc solvate

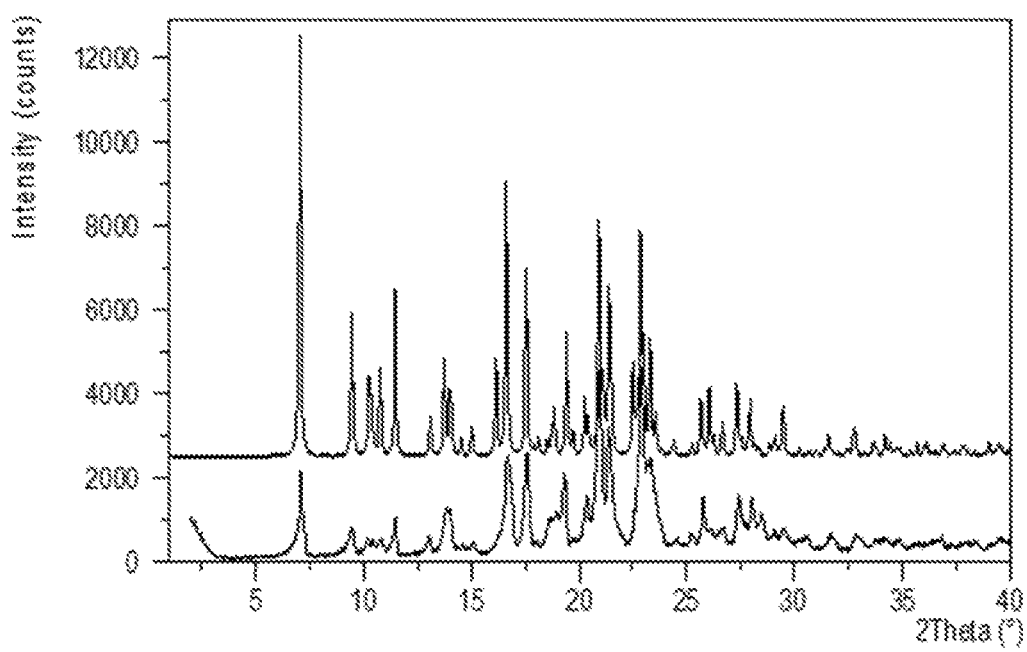
FIG. 38 - XRPD pattern of Formula I, ethyl formate solvate

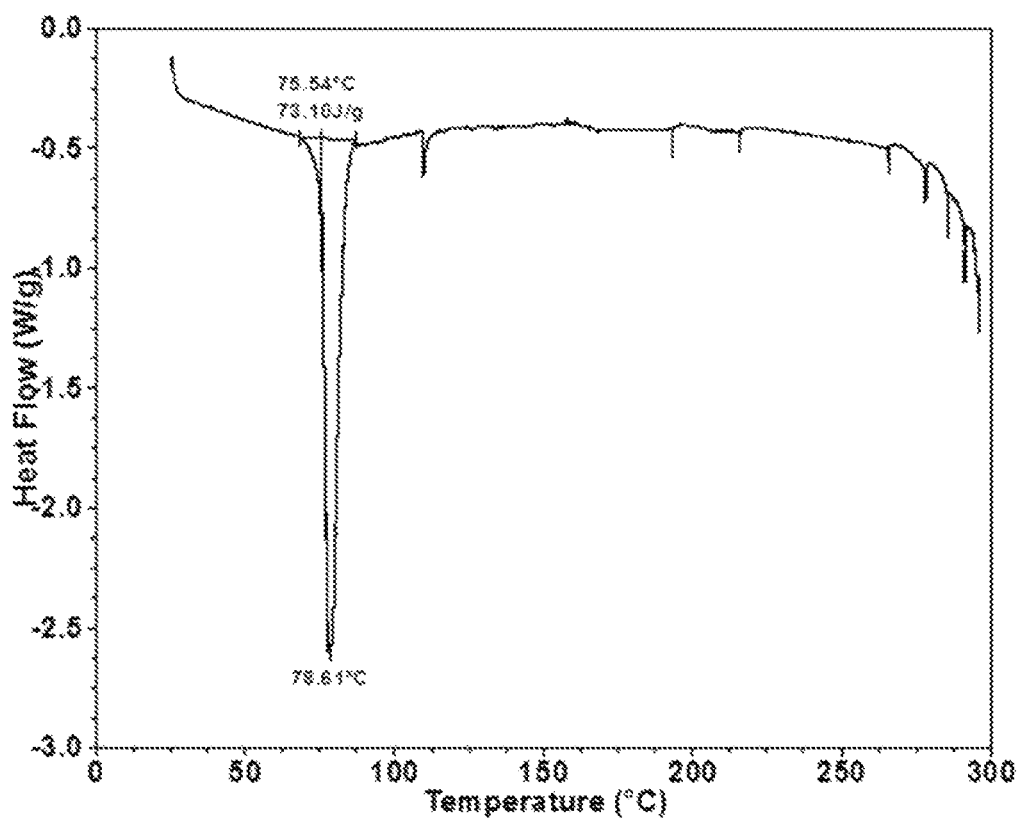
FIG. 39 - DSC thermogram of Formula I, ethyl formate solvate

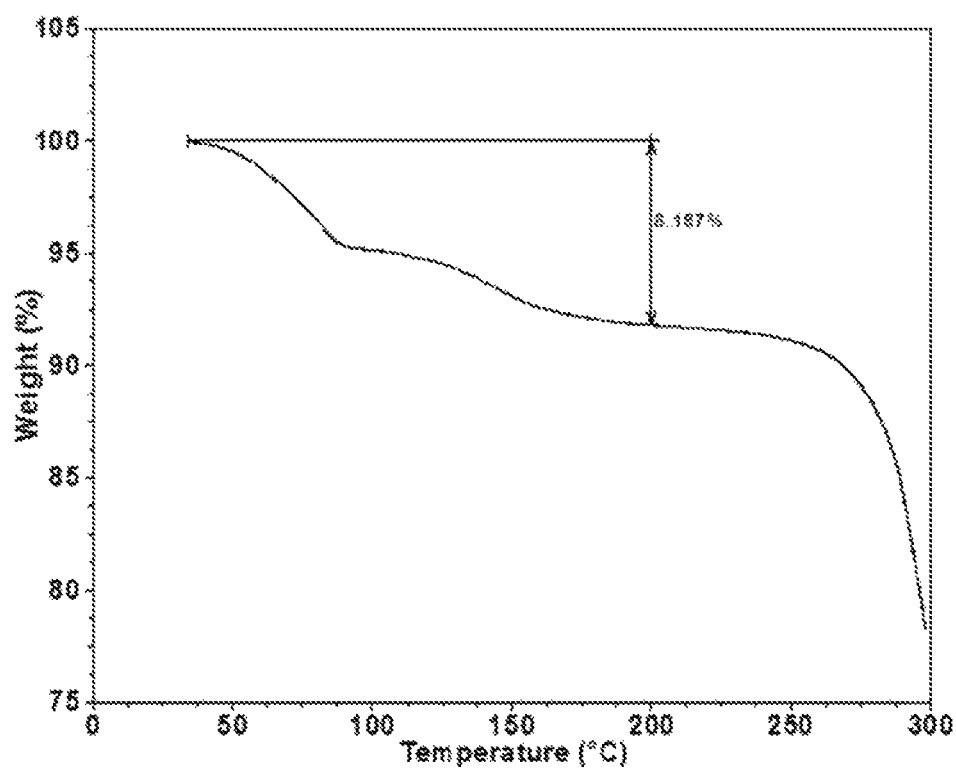
FIG. 40 - TGA thermogram of Formula I, ethyl formate solvate

CRYSTALLINE FORMS OF DARUNAVIR

CROSS-REFERENCE TO RELATED APPLICATION

This Application claims the benefit of U.S. Provisional Application 62/413,601 filed on Oct. 27, 2016. The entire contents of this application are incorporated herein by reference in their entirety.

FIELD

The present invention relates to novel crystalline forms of darunavir, and the pharmaceutical formulations and therapeutic uses thereof.

BACKGROUND

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. N. Engl. J Med. (1998) 338:853-860; Richman, D. D. Nature (2001) 410:995-1001).

A goal of antiretroviral therapy is to achieve viral suppression in the HIV infected patient. Treatment guidelines published by the United States Department of Health and Human Services provide that achievement of viral suppression requires the use of combination therapies, i.e., several drugs from at least two or more drug classes. In addition, decisions regarding the treatment of HIV infected patients are complicated when the patient requires treatment for other medical conditions. Because the standard of care requires the use of multiple different drugs to suppress HIV, as well as to treat other conditions the patient may be experiencing, the potential for drug interaction is a criterion for selecting a drug regimen. Therefore, there is a need for antiretroviral therapies having a decreased potential for drug interactions.

Despite the success of potent and well-tolerated antiretroviral therapy (ART), mutations of the HIV-1 virus continue to occur in clinical settings. For example, some treatment-experienced patients on ART experience drug resistance. As a result, achieving virological suppression in this patient population is complex. In view of these challenges, there remains a significant medical need for safe and effective new therapies that address virologic resistance. Moreover, new therapies for patients experiencing virologic resistance must also: (i) exhibit tolerability, long-term safety, and adherence (Costagliola D. Demographics of HIV and aging Curr. Opin. HIV AIDS, 2014, 9(4), 294); as well as (ii) consider the aging patient population, non-HIV-related comorbidities, and regimen simplification.

As discussed in PCT Publication no. WO1995/06030, darunavir demonstrates antiviral activity.

Darunavir (Formula I) has the following structure:

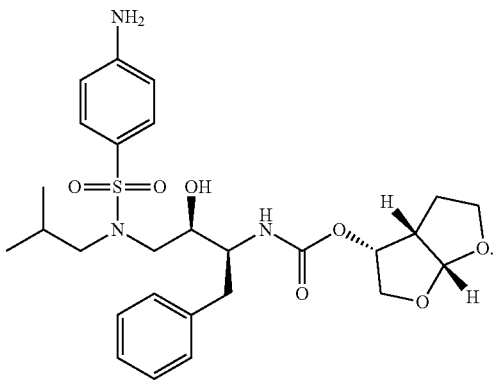

Formula I

There is a need for stable forms of the compound of Formula I with suitable chemical and physical stability for the formulation, therapeutic use, manufacturing, and storage of the compound.

SUMMARY

In some embodiments, the present invention is directed to novel forms of a compound of Formula I.

In some embodiments, the present invention is directed to crystalline forms of darunavir.

In some embodiments, the present invention is directed to darunavir Form I (Formula I Form I).

In some embodiments, the present invention is directed to a hydrated darunavir (Formula I Hydrate I).

In some embodiments, the present invention is directed to a solvated darunavir (Formula I Solvate). In some embodiments, the solvate is acetic acid (Formula I, Acetic Acid Solvate I).

In some embodiments, the present invention is directed to darunavir esylate (Formula I Esylate I).

In some embodiments, the present invention is directed to darunavir besylate (Formula I Besylate I).

In some embodiments, the present invention is directed to darunavir hemisulfate (Formula I Hemisulfate I).

In some embodiments, the present invention is directed to darunavir hemiedisylate (Formula I Hemiedisylate I).

In some embodiments, the present invention is directed to darunavir napsylate (Formula I Napsylate I).

In some embodiments, the present invention is directed to darunavir tosylate (Formula I Tosylate I).

In some embodiments, the present invention is directed to a free base form of darunavir (Formula I, Material A).

In some embodiments, the present invention is directed to a methyl ethyl ketone (MEK) solvate form of darunavir (Formula I, MEK solvate).

In some embodiments, the present invention is directed to a methyl tetrahydrofuran (MeTHF) solvate form of darunavir (Formula I, MeTHF solvate).

In some embodiments, the present invention is directed to a methyl acetate (MeOAc) form of darunavir (Formula I, MeOAc solvate).

In some embodiments, the present invention is directed to an ethyl formate solvate form of darunavir (Formula I, ethyl formate solvate).

In some embodiments, the present invention is directed to methods of treating and/or prophylactically preventing an HIV infection by administering a therapeutically effective amount of a compound (e.g. Formula I) provided herein.

In some embodiments, the present invention is directed to a compound (e.g., a compound of Formula I) provided herein for use in methods of treating and/or prophylactically preventing an HIV infection.

In some embodiments, the present invention is directed to the use of a compound (e.g., a compound of Formula I) provided herein in the manufacture of a medicament for treating or prophylactically preventing HIV infection.

DESCRIPTION OF THE FIGURES

FIG. 1 shows an XRPD pattern of the compound of Formula I Form I.

FIG. 2 shows a DSC thermogram of the compound of Formula I Form I.

FIG. 3 shows a TGA thermogram of the compound of Formula I Form I.

FIG. 4 shows a DVS pattern of the compound of Formula I Form I.

FIG. 5 shows an XRPD pattern of the compound of Formula I Hydrate I.

FIG. 6a shows a DSC thermogram of the compound of Formula I Hydrate I.

FIG. 6b shows a DSC thermogram of a compound of Formula I, Hydrate I having about 6 equiv. of associated water.

FIG. 7a shows a TGA thermogram of the compound of Formula I Hydrate I.

FIG. 7b shows a TGA thermogram of a compound of Formula I, Hydrate I, having about 6 equiv. of associated water.

FIG. 8 shows an XRPD pattern of the compound of Formula I Acetic Acid Solvate I.

FIG. 9 shows a DSC thermogram of the compound of Formula I Acetic Acid Solvate I.

FIG. 10 shows a TGA thermogram of the compound of Formula I Acetic Acid Solvate I.

FIG. 11 shows an XRPD pattern of the compound of Formula I Esylate I.

FIG. 12 shows a DSC thermogram of the compound of Formula I Esylate I.

FIG. 13 shows a TGA thermogram of the compound of Formula I Esylate I.

FIG. 14 shows a DVS pattern of the compound of Formula I Esylate I.

FIG. 15 shows an XRPD pattern of the compound of Formula I Besylate I.

FIG. 16 shows a DSC thermogram of the compound of Formula I Besylate I.

FIG. 17: shows a TGA thermogram of the compound of Formula I Besylate I.

FIG. 18 shows an XRPD pattern of the compound of Formula I Hemisulfate I.

FIG. 19 shows a DSC thermogram of the compound of Formula I Hemisulfate I.

FIG. 20 shows an XRPD pattern of the compound of Formula I Napsylate I.

FIG. 21 shows a DSC thermogram of the compound of Formula I Napsylate I.

FIG. 22 shows an XRPD pattern of the compound of Formula I Hemiedisylate I.

FIG. 23 shows a DSC thermogram of the compound of Formula I Hemiedisylate I.

FIG. 24 shows an XRPD pattern of the compound of Formula I Tosylate I.

FIG. 25 shows a DSC thermogram of the compound of Formula I Tosylate I.

FIG. 26 shows a XRPD pattern of a compound of Formula I, Material A.

FIG. 27 shows a DSC thermogram of a compound of Formula I, Material A.

FIG. 28 shows a TGA thermogram of a compound of Formula I, Material A.

FIG. 29 shows a XRPD pattern of a compound of Formula I, MEK solvate.

FIG. 30 shows a DSC thermogram of a compound of Formula I, MEK solvate.

FIG. 31 shows a TGA thermogram of a compound of Formula I, MEK solvate.

FIG. 32 shows a XRPD pattern of a compound of Formula I, MeTHF solvate.

FIG. 33 shows a DSC thermogram of a compound of Formula I, MeTHF solvate.

FIG. 34 shows a TGA thermogram of a compound of Formula I, MeTHF solvate.

FIG. 35 shows a XRPD pattern of a compound of Formula I, MeOAc solvate.

FIG. 36 shows a DSC thermogram of a compound of Formula I, MeOAc solvate.

FIG. 37 shows a TGA thermogram of a compound of Formula I, MeOAc solvate.

FIG. 38 shows a XRPD pattern of a compound of Formula I, ethyl formate solvate.

FIG. 39 shows a DSC thermogram of a compound of Formula I, ethyl formate solvate.

FIG. 40 shows a TGA thermogram of a compound of Formula I, ethyl formate solvate.

DETAILED DESCRIPTION

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments that reference throughout this specification to "a compound" includes the crystalline, salt, co-crystal, and solvate forms of the formulas and/or compounds disclosed herein. Thus, the appearance or the phrase "a compound of Formula I" comprises Formula I Form I, Formula I Hydrate I, Formula I Solvate I (e.g., Acetic Acid Solvate I), Formula I Esylate I, Formula I Besylate I, Formula I Hemisulfate I, Formula I Napsylate I, Formula I Hemiedisylate I, and Formula I Tosylate I. Similarly, the appearance or the phrase "a compound of Formula I" also comprises Formula I, Material A, Formula I, MEK (methyl ethyl ketone) solvate, Formula I, MeTHF (methyl tetrahydrofuran) solvate, Formula I, MeOAc (methyl acetate) solvate, and Formula I, ethyl formate solvate.

The invention disclosed herein is also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula I, for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula I can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, and/or emulsifier, or a combination of one or more of the above which has been approved by the United States Food and Drug Administration as being acceptable for use in humans or domestic animals.

A "pharmaceutical composition" refers to a formulation of a compound of the invention and a medium generally accepted in the art for the delivery of the biologically active compound to mammals, e.g., humans. Such a medium includes all pharmaceutically acceptable excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above. In certain embodiments, the term "treatment" is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life. In certain embodiments, the term "treatment" as used herein is intended to mean the administration of a compound or composition according to the present invention to alleviate or eliminate symptoms of HIV infection and/or to reduce viral load in a patient. In certain embodiments, the term "treatment" as used herein is further or alternatively intended to mean the administration of a compound or composition according to the present invention to maintain a reduced viral load in a patient. In certain embodiments, the term "treatment" as used herein is further or alternatively intended to mean the administration of a compound or composition according to the present invention post-exposure of the individual to the virus as a subsequent or additional therapy to a first-line therapy (e.g., for maintenance of low viral load). In a particular embodiment, the term "treatment" as used herein is further or alternatively intended to mean the prevention of an HIV infection from taking hold if an individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound of Formula I disclosed herein. In certain specific embodiments, methods for reducing the risk of acquiring HIV (e.g., HIV-1 and/or HIV-2) comprise administration of a compound of Formula I disclosed herein in combination with safer sex practices. In certain embodiments, methods for reducing the risk of acquiring HIV (e.g., HIV-1 and/or HIV-2) comprise administration of a compound of Formula I to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

"Prevention" or "preventing" means any treatment of a disease or condition that causes the clinical symptoms of the disease or condition not to develop. The term "prevention" also encompasses the administration of a therapeutically effective amount of a compound or composition according to the present invention pre-exposure of the individual to the virus (e.g., pre-exposure prophylaxis), to prevent the appearance of symptoms of the disease and/or to prevent the virus from reaching detectible levels in the blood.

The terms "subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In some embodiments, the subject (or the patient) is a human. "Human (or patient) in need thereof" refers to a human who may have or is suspect to have diseases or conditions that would benefit from certain treatment; for example, being treated with the compounds disclosed herein according to the present application. The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical excipient.

The term "substantially as shown in" when referring, for example, to an XRPD pattern, a DSC thermogram, a DVS graph, or a TGA thermogram includes a pattern, thermogram or graph that is not necessarily identical to those depicted herein, but that falls within the limits of experimental error or deviations when considered by one of ordinary skill in the art.

In some embodiments, the term "substantially pure" or "substantially free" with respect to a particular crystalline form of a compound means that the composition comprising the crystalline form contains less than 99%, less than 95%, less than 90%, less than 85%, less than 80%, less than 75%, less than 70%, less than 65%, less than 60%, less than 55%, less than 50%, less than 40%, less than 30%, less than 20%, less than 15%, less than 10%, less than 5%, or less than 1% by weight of other substances, including other crystalline forms and/or impurities. In certain embodiments, "substantially pure" or "substantially free of" refers to a substance free of other substances, including other crystalline forms and/or impurities. Impurities may, for example, include by-products or left over reagents from chemical reactions, contaminants, degradation products, other crystalline forms, water, and solvents.

Crystalline Forms of Formula I

It is desirable to develop a crystalline form of Formula I that may be useful in the synthesis of Formula I. A crystalline form of a Formula I may be an intermediate to the synthesis of Formula I. A crystalline form may have properties such as bioavailability, stability, purity, and/or manufacturability at certain conditions that may be suitable for medical or pharmaceutical uses.

Crystalline forms of Formula I, including substantially pure forms, may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of the compound of Formula I may provide advantages such as improving: the manufacturing process of the compound, the stability or storability of a drug product form of the compound, the stability or storability of a drug substance of the compound and/or the bioavailability and/or stability of the compound as an active agent.

The use of certain solvents and/or processes have been found to produce different crystalline forms of the compound Formula I described herein which may exhibit one or more favorable characteristics described above. The processes for the preparation of the crystalline forms described herein and characterization of these crystalline forms are described in detail below.

One skilled in the art understands that a compound structure may be named or identified using commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure for darunavir provided above may also be named or identified as (3R,3aS,6aR)-hexahydrofuro[2,3-b]furan-3-yl ((2S,3R)-4-(4-amino-N-isobutylphenylsulfonamido)-3-hydroxy-l-phenylbutan-2-yl)carbamate under IUPAC and R1S,2R)-3-[[(4-aminophenyl)sulfonyl](2-methylpropyl)amino]-2-hydroxy-1-(phenylmethyl) propyl]-carbamic acid (3R,3aS,6aR)-hexahydrofuro[2,3-b]furan-3-yl ester under CAS; CAS Registry Number 206361-99-1.

In particular embodiments, crystalline forms of Formula I are disclosed.

Formula I Form I

In some embodiments, provided is crystalline Form I of the compound of Formula I (Formula I Form I), wherein the crystal structure exhibits an X-ray powder diffraction (XRPD) pattern substantially as shown in FIG. 1. Crystalline Formula I Form I may exhibit a differential scanning calorimetry (DSC) thermogram substantially as shown in FIG. 2. Crystalline Formula I Form I may exhibit a thermogravimetric analysis (TGA) thermogram substantially as shown in FIG. 3. Crystalline Formula I Form I may exhibit a dynamic vapor sorption (DVS) graph substantially as shown in FIG. 4.

In some embodiments of crystalline Formula I Form I, at least one, at least two, at least three, at least four, or all of the following (a)-(d) apply: (a) crystalline Formula I Form I has an XRPD pattern substantially as shown in FIG. 1; (b) crystalline Formula I Form I has a DSC thermogram substantially as shown in FIG. 2; (c) crystalline Formula I Form I has a TGA graph substantially as shown in FIG. 3; (d) crystalline Formula I Form I has a DVS graph substantially as shown in FIG. 4.

In some embodiments, crystalline Formula I Form I has at least one, at least two, at least three, or all of the following properties:
an XRPD pattern substantially as shown in FIG. 1
a DSC thermogram substantially as shown in FIG. 2
a TGA graph substantially as shown in FIG. 3
a DVS graph substantially as shown in FIG. 4.

In some embodiments, crystalline Formula I Form I has an XRPD pattern displaying at least two, at least three, at least four, at least five, or at least six of the degree 2θ-reflections with the greatest intensity as the XRPD pattern substantially as shown in FIG. 1.

In certain embodiments, crystalline Formula I Form I has an XRPD pattern comprising degree 2θ-reflections (+/−0.2 degrees 2θ) at 7.2°, 17.8°, and 25.1°. In some embodiments, crystalline Formula I Form I has an XRPD pattern comprising degree 2θ-reflections (+/−0.2 degrees 2θ) at 7.2°, 17.8°, and 25.1° and one or more of the degree 2θ-reflections (+/−0.2 degrees 2θ) at 10.8°, 14.3° and 18.3°. In some embodiments, crystalline Formula I Form I has an XRPD pattern comprising degree 2θ-reflections (+/−0.2 degrees 2θ) at 7.2°, 17.8°, and 25.1° and one of the degree 2θ-reflections (+/−0.2 degrees 2θ) at 10.8°, 14.3° and 18.3°. In some embodiments, crystalline Formula I Form I has an XRPD pattern comprising degree 2θ-reflections (+/−0.2 degrees 2θ) at 7.2°, 17.8°, and 25.1° and two of the degree 2θ-reflections (+/−0.2 degrees 2θ) at 10.8°, 14.3° and 18.3°. In some embodiments, crystalline Formula I Form I has an XRPD pattern comprising degree 2θ-reflections (+/−0.2 degrees 2θ) at 7.2°, 17.8°, 25.1°, 10.8°, 14.3° and 18.3°. In some embodiments, crystalline Formula I Form I has an XRPD pattern comprising any three degree 2θ-reflections (+/−0.2 degrees 2θ) selected from the group consisting of 7.2°, 17.8°, 25.1°, 10.8°, 14.3° and 18.3°. In some embodiments, crystalline Formula I Form I has an XRPD pattern comprising any three degree 2θ-reflections (+/−0.2 degrees 2θ) selected from the group consisting of 7.2°, 9.9°, 10.8°, 11.7°, 14.3°, 16.9°, 17.8°, 18.3°, 18.8°, 19.3°, 20.7°, 21.4°, 23.4°, 25.1°, 25.8°, 26.3°, 26.8°, 27.5°, 28.7°, 29.7°, 31.3°, 32.0°, 32.5°, 33.8°, 35.3°, 36.5°, and 37.4°. In some embodiments, crystalline Formula I Form I has an XRPD pattern comprising any six degree 2θ-reflections (+/−0.2 degrees 2θ) selected from the group consisting of 7.2°, 9.9°, 10.8°, 11.7°, 14.3°, 16.9°, 17.8°, 18.3°, 18.8°, 19.3°, 20.7°, 21.4°, 23.4°, 25.1°, 25.8°, 26.3°, 26.8°, 27.5°, 28.7°, 29.7°, 31.3°, 32.0°, 32.5°, 33.8°, 35.3°, 36.5°, and 37.4°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 7.2°, 9.9°, 10.8°, 11.7°, 14.3°, 16.9°, 17.8°, 18.3°, 18.8°, 19.3°, 20.7°, 21.4°, 23.4°, 25.1°, 25.8°, 26.3°, 26.8°, 27.5°, 28.7°, 29.7°, 31.3°, 32.0°, 32.5°, 33.8°, 35.3°, 36.5°, and 37.4° and at least one, at least two, at least three, or all of the following properties:
an XRPD pattern substantially as shown in FIG. 1
a DSC thermogram substantially as shown in FIG. 2
a TGA graph substantially as shown in FIG. 3
a DVS graph substantially as shown in FIG. 4.

Formula I Hydrate I

In some embodiments, provided is crystalline compound of Formula I Hydrate I (crystalline Formula I Hydrate I), wherein the crystal structure exhibits an X-ray powder diffraction (XRPD) pattern substantially as shown in FIG. 5. Crystalline Formula I Hydrate I may exhibit a differential scanning calorimetry (DSC) thermogram substantially as shown in FIG. 6a and FIG. 6b. The Hydrate I forms of Formula I created and characterized here may have a range of water content. FIG. 6a shows a DSC thermogram of Hydrate I where some water has been taken up and associated with Formula I. FIG. 6b show a DSC thermogram of Hydrate I where more water (approximately 6 equivalents) has been taken up by Formula I. Crystalline Formula I Hydrate I may exhibit a thermogravimetric analysis (TGA) graph substantially as shown in FIG. 7a. FIG. 7a is a TGA graphic representation of Hydrate I where some water is associated with Formula I. FIG. 7b shows a TGA graph for Formula I Hydrate I where more (approximately 6 equivalents of) water is present. Accordingly, in some embodiments, Formula I Hydrate I has more than about 6 equivalents of water. In some embodiments, Formula I Hydrate I has approximately 6-12, approximately 6-10, or approximately 6-8 equivalents of water. In some embodiments, Formula I Hydrate I has approximately 8 equivalents of water. In some embodiments, Formula I Hydrate I has approximately 10 equivalents of water. In some embodiments, Formula I Hydrate I has approximately 12 equivalents of water.

In some embodiments of crystalline Formula I Hydrate I, at least one, at least two, or all of the following (a)-(c) apply: (a) crystalline Formula I Hydrate I has an XRPD pattern substantially as shown in FIG. 5; (b) crystalline Formula I Hydrate I has a DSC thermogram substantially as shown in FIG. 6; (c) crystalline Formula I Hydrate I has a TGA graph substantially as shown in FIG. 7.

In some embodiments of crystalline Formula I Hydrate I, at least one, at least two, or all of the following (a)-(c) apply: (a) crystalline Formula I Hydrate I has an XRPD pattern substantially as shown in FIG. 5; (b) crystalline Formula I Hydrate I has a thermogram substantially as shown in FIG. 6b; and (c) crystalline Formula I Hydrate I has a TGA graph substantially as shown in FIG. 7b In some embodiments, crystalline Formula I Hydrate I has at least one, at least two, or all of the following properties:
an XRPD pattern substantially as shown in FIG. 5
a DSC thermogram substantially as shown in FIG. 6a
a TGA graph substantially as shown in FIG. 7a In some embodiments, crystalline Formula I Hydrate I has at least one, at least two, or all of the following properties:
an XRPD pattern substantially as shown in FIG. 5
a DSC thermogram substantially as shown in FIG. 6b
a TGA graph substantially as shown in FIG. 7b In some embodiments, crystalline Formula I Hydrate I has an XRPD pattern displaying at least two, at least three, at least four, at least five, or at least six of the degree 2θ-reflections with the greatest intensity as the XRPD pattern substantially as shown in FIG. 5.

In certain embodiments, crystalline Formula I Hydrate I has an XRPD pattern comprising degree 2θ-reflections (+/−0.2 degrees 2θ) at 5.3°, 7.6°, and 15.9°. In some embodiments, crystalline Formula I Hydrate I has an XRPD pattern comprising degree 2θ-reflections (+/−0.2 degrees 2θ) at 5.3°, 7.6°, and 15.9° and one or more of the degree 2θ-reflections (+/−0.2 degrees 2θ) at 10.6°, 18.0°, and 21.9°. In some embodiments, crystalline Formula I Hydrate I has an XRPD pattern comprising degree 2θ-reflections (+/−0.2 degrees 2θ) at 5.3°, 7.6°, and 15.9° and one of the degree 2θ-reflections (+/−0.2 degrees 2θ) at 10.6°, 18.0°, and 21.9°. In some embodiments, crystalline Formula I Hydrate I has an XRPD pattern comprising degree 2θ-reflections (+/−0.2 degrees 2θ) at 5.3°, 7.6°, and 15.9° and two of the degree 2θ-reflections (+/−0.2 degrees 2θ) at 10.6°, 18.0°, and 21.9°. In some embodiments, crystalline Formula I Hydrate I has an XRPD pattern comprising degree 2θ-reflections (+/−0.2 degrees 2θ) at 5.3°, 7.6°, 15.9°, 10.6°, 18.0°, and 21.9°. In some embodiments, crystalline Formula I Hydrate I has an XRPD pattern comprising any three degree 2θ-reflections (+/−0.2 degrees 2θ) selected from the group consisting of 5.3°, 7.6°, 15.9°, 10.6°, 18.0°, and 21.9°. In some embodiments, crystalline Formula I Hydrate I has an XRPD pattern comprising any three degree 2θ-reflections (+/−0.2 degrees 2θ) selected from the group consisting of 5.3°, 7.4°, 7.6°, 8.3°, 10.6°, 11.7°, 13.6°, 15.9°, 17.6°, 18.0°, 18.8°, 19.2°, 19.4°, 19.9°, 20.2°, 20.5°, 20.7°, 21.0°, 21.9°, 22.4°, 22.7°, 23.5°, 24.1°, 25.6°, 26.0°, 26.6°, 27.4°, 28.8°, 34.9°, and 35.4°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 5.3°, 7.4°, 7.6°, 8.3°, 10.6°, 11.7°, 13.6°, 15.9°, 17.6°, 18.0°, 18.8°, 19.2°, 19.4°, 19.9°, 20.2°, 20.5°, 20.7°, 21.0°, 21.9°, 22.4°, 22.7°, 23.5°, 24.1°, 25.6°, 26.0°, 26.6°, 27.4°, 28.8°, 34.9°, and 35.4° and at least one, at least two, at least three, or all of the following properties:
an XRPD pattern substantially as shown in FIG. 5,
a DSC thermogram substantially as shown in FIG. 6a or 6b, and
a TGA graph substantially as shown in FIG. 7a or 7b.

Formula I Acetic Acid Solvate

In some embodiments, provided is crystalline Formula I Acetic Acid Solvate (crystalline Formula I Acetic Acid Solvate I), wherein the crystal structure exhibits an X-ray powder diffraction (XRPD) pattern substantially as shown in FIG. 8. Crystalline Formula I Acetic Acid Solvate I may exhibit a differential scanning calorimetry (DSC) thermogram substantially as shown in FIG. 9. Crystalline Formula I Acetic Acid Solvate I may exhibit a thermogravimetric analysis (TGA) graph substantially as shown in FIG. 10.

In some embodiments of crystalline Formula I Acetic Acid Solvate I, at least one, at least two, or all of the following (a)-(c) apply: (a) crystalline Formula I Acetic Acid Solvate I has an XRPD pattern substantially as shown in FIG. 8; (b) crystalline Formula I Acetic Acid Solvate I has a DSC thermogram substantially as shown in FIG. 9; (c) crystalline Formula I Acetic Acid Solvate I has a TGA graph substantially as shown in FIG. 10.

In some embodiments, crystalline Formula I Acetic Acid Solvate I has at least one, at least two, or all of the following properties:
an XRPD pattern substantially as shown in FIG. 8
a DSC thermogram substantially as shown in FIG. 9
a TGA graph substantially as shown in FIG. 10

In some embodiments, crystalline Formula I Acetic Acid Solvate I has an XRPD pattern displaying at least two, at least three, at least four, at least five, or at least six of the degree 2θ-reflections with the greatest intensity as the XRPD pattern substantially as shown in FIG. 8.

In certain embodiments, crystalline Formula I Acetic Acid Solvate I has an XRPD pattern comprising degree 2θ-reflections (+/−0.2 degrees 2θ) at 7.2°, 16.8°, and 21.3°. In some embodiments, crystalline Formula I Acetic Acid Solvate I has an XRPD pattern comprising degree 2θ-reflections (+/−0.2 degrees 2θ) at 7.2°, 16.8°, and 21.3° and one or more of the degree 2θ-reflections (+/−0.2 degrees 2θ) at 14.0°, 20.5°, and 23.1°. In some embodiments, crystalline Formula I Acetic Acid Solvate I has an XRPD pattern comprising degree 2θ-reflections (+/−0.2 degrees 2θ) at 7.2°, 16.8°, and 21.3° and one of the degree 2θ-reflections (+/−0.2 degrees 2θ) at 14.0°, 20.5°, and 23.1°. In some embodiments, crystalline Formula I Acetic Acid Solvate I has an XRPD pattern comprising degree 2θ-reflections (+/−0.2 degrees 2θ) at 7.2°, 16.8°, and 21.3° and two of the degree 2θ-reflections (+/−0.2 degrees 2θ) at 14.0°, 20.5°, and 23.1°. In some embodiments, crystalline Formula I Acetic Acid Solvate I has an XRPD pattern comprising degree 2θ-reflections (+/−0.2 degrees 2θ) at 7.2°, 16.8°, 21.3°, 14.0°, 20.5°, and 23.1°. In some embodiments, crystalline Formula I Acetic Acid Solvate I has an XRPD pattern comprising any three degree 2θ-reflections (+/−0.2 degrees 2θ) selected from the group consisting of 7.2°, 16.8°, 21.3°, 14.0°, 20.5°, and 23.1°. In some embodiments, crystalline Formula I Acetic Acid Solvate I has an XRPD pattern comprising any three degree 2θ-reflections (+/−0.2 degrees 2θ) selected from the group consisting of 7.2°, 9.3°, 10.0°, 10.7°, 11.4°, 12.8°, 14.0°, 14.7°, 16.8°, 17.3°, 18.4°, 19.1°, 20.0°, 20.5°, 21.3°, 22.1°, 22.8°, 23.1°, 23.8°, 24.5°, 25.0°, 25.8°, 26.2°, 27.0°, 28.4°, 29.2°, 30.5°, 31.3°, 32.7°, 33.6°, 38.8°, and 39.5°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 7.2°, 9.3°, 10.0°, 10.7°, 11.4°, 12.8°, 14.0°, 14.7°, 16.8°, 17.3°, 18.4°, 19.1°, 20.0°, 20.5°, 21.3°, 22.1°, 22.8°, 23.1°, 23.8°, 24.5°, 25.0°, 25.8°, 26.2°, 27.0°, 28.4°, 29.2°, 30.5°, 31.3°, 32.7°, 33.6°, 38.8°, and 39.5° and at least one, at least two, at least three, or all of the following properties:

an XRPD pattern substantially as shown in FIG. 8,
a DSC thermogram substantially as shown in FIG. 9, and
a TGA graph substantially as shown in FIG. 10.

Formula I Esylate I

In some embodiments, provided is crystalline Formula I Esylate I (crystalline Formula I Esylate I), wherein the crystal structure exhibits an X-ray powder diffraction (XRPD) pattern substantially as shown in FIG. 11. Crystalline Formula I Esylate I may exhibit a differential scanning calorimetry (DSC) thermogram substantially as shown in FIG. 12. Crystalline Formula I Esylate I may exhibit a thermogravimetric analysis (TGA) graph substantially as shown in FIG. 13. Crystalline Formula I Esylate I may exhibit dynamic vapor sorption (DVS) graphs substantially as shown in FIG. 14.

In some embodiments of crystalline Formula I Esylate I, at least one, at least two, at least three, or all of the following (a)-(d) apply: (a) crystalline Formula I Esylate I has an XRPD pattern substantially as shown in FIG. 11; (b) crystalline Formula I Esylate I has a DSC thermogram substantially as shown in FIG. 12; (c) crystalline Formula I Esylate I has a TGA graph substantially as shown in FIG. 13; (d) crystalline Formula I Esylate I has a dynamic vapor sorption (DVS) graph as shown in FIG. 14.

In some embodiments, crystalline Formula I Esylate I has at least one, at least two, or all of the following properties:

an XRPD pattern substantially as shown in FIG. 11
a DSC thermogram substantially as shown in FIG. 12
a TGA graph substantially as shown in FIG. 13
a DVS graph as shown in FIG. 14.

In some embodiments, crystalline Formula I Esylate I has an XRPD pattern displaying at least two, at least three, at least four, at least five, or at least six of the degree 2θ-reflections with the greatest intensity as the XRPD pattern substantially as shown in FIG. 11.

In certain embodiments, crystalline Formula I Esylate I has an XRPD pattern comprising degree 2θ-reflections (+/−0.2 degrees 2θ) at 9.9°, 17.9°, and 21.5°. In some embodiments, crystalline Formula I Esylate I has an XRPD pattern comprising degree 2θ-reflections (+/−0.2 degrees 2θ) at 9.9°, 17.9°, and 21.5° and one or more of the degree 2θ-reflections (+/−0.2 degrees 2θ) at 8.2°, 18.6°, and 19.7°. In some embodiments, crystalline Formula I Esylate I has an XRPD pattern comprising degree 2θ-reflections (+/−0.2 degrees 2θ) at 9.9°, 17.9°, and 21.5° and one of the degree 2θ-reflections (+/−0.2 degrees 2θ) at 8.2°, 18.6°, and 19.7°. In some embodiments, crystalline Formula I Esylate I has an XRPD pattern comprising degree 2θ-reflections (+/−0.2 degrees 2θ) at 9.9°, 17.9°, and 21.5° and two of the degree 2θ-reflections (+/−0.2 degrees 2θ) at 8.2°, 18.6°, and 19.7°. In some embodiments, crystalline Formula I Esylate I has an XRPD pattern comprising degree 2θ-reflections (+/−0.2 degrees 2θ) at 9.9°, 17.9°, 21.5°, 8.2°, 18.6°, and 19.7°. In some embodiments, crystalline Formula I Esylate I has an XRPD pattern comprising any three degree 2θ-reflections (+/−0.2 degrees 2θ) selected from the group consisting of 9.9°, 17.9°, 21.5°, 8.2°, 18.6°, and 19.7°. In some embodiments, crystalline Formula I Esylate I has an XRPD pattern comprising any three degree 2θ-reflections (+/−0.2 degrees 2θ) selected from the group consisting of 9.9°, 10.2°, 11.1°, 11.3°, 13.4°, 14.1°, 15.6°, 16.6°, 17.9°, 19.0°, 19.6°, 19.9°, 20.3°, 20.9°, 21.5°, 22.1°, 22.6°, 22.9°, 23.8°, 24.8°, 25.0°, 26.6°, 27.3°, 28.0°, 28.6°, 29.6°, 32.5°, 34.9°, 35.7°, 36.0°, 36.6°, 37.1°, and 38.9°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 9.9°, 10.2°, 11.1°, 11.3°, 13.4°, 14.1°, 15.6°, 16.6°, 17.9°, 19.0°, 19.6°, 19.9°, 20.3°, 20.9°, 21.5°, 22.1°, 22.6°, 22.9°, 23.8°, 24.8°, 25.0°, 26.6°, 27.3°, 28.0°, 28.6°, 29.6°, 32.5°, 34.9°, 35.7°, 36.0°, 36.6°, 37.1°, and 38.9° and at least one, at least two, at least three, or all of the following properties:

an XRPD pattern substantially as shown in FIG. 11
a DSC thermogram substantially as shown in FIG. 12
a TGA graph substantially as shown in FIG. 13
a DVS graph as substantially shown in FIG. 14.

Formula I Besylate I

In some embodiments, provided is crystalline Formula I Besylate I (crystalline Formula I Besylate I), wherein the crystal structure exhibits an X-ray powder diffraction (XRPD) pattern substantially as shown in FIG. 15. Crystalline Formula I Besylate I may exhibit a differential scanning calorimetry (DSC) thermogram substantially as shown in FIG. 16. Crystalline Formula I Besylate I may exhibit a thermogravimetric analysis (TGA) graph substantially as shown in FIG. 17.

In some embodiments of crystalline Formula I Besylate I, at least one, at least two, or all of the following (a)-(c) apply: (a) crystalline Formula I Besylate I has an XRPD pattern substantially as shown in FIG. 15; (b) crystalline Formula I Besylate I has a DSC thermogram substantially as shown in FIG. 16; (c) crystalline Formula I Besylate I has a TGA graph substantially as shown in FIG. 17.

In some embodiments, crystalline Formula I Besylate I has at least one, at least two, or all of the following properties:

an XRPD pattern substantially as shown in FIG. 15
a DSC thermogram substantially as shown in FIG. 16
a TGA graph substantially as shown in FIG. 17.

In some embodiments, crystalline Formula I Besylate I has an XRPD pattern displaying at least two, at least three, at least four, at least five, or at least six of the degree 2θ-reflections with the greatest intensity as the XRPD pattern substantially as shown in FIG. 15.

In certain embodiments, crystalline Formula I Besylate I has an XRPD pattern comprising degree 2θ-reflections (+/−0.2 degrees 2θ) at 8.4°, 19.4°, and 25.0°. In some embodiments, crystalline Formula I Besylate I has an XRPD pattern comprising degree 2θ-reflections (+/−0.2 degrees 2θ) at 8.4°, 19.4°, and 25.0° and one or more of the degree 2θ-reflections (+/−0.2 degrees 2θ) at 13.9°, 16.6°, and 30.6°. In some embodiments, crystalline Formula I Besylate I has an XRPD pattern comprising degree 2θ-reflections (+/−0.2 degrees 2θ) at 8.4°, 19.4°, and 25.0° and one of the degree 2θ-reflections (+/−0.2 degrees 2θ) at 13.9°, 16.6°, and 30.6°. In some embodiments, crystalline Formula I Besylate I has an XRPD pattern comprising degree 2θ-reflections (+/−0.2 degrees 2θ) at 8.4°, 19.4°, and 25.0° and two of the degree 2θ-reflections (+/−0.2 degrees 2θ) at 13.9°, 16.6°, and 30.6°. In some embodiments, crystalline Formula I Besylate I has an XRPD pattern comprising degree 2θ-reflections (+/−0.2 degrees 2θ) at 8.4°, 19.4°, 25.0°, 13.9°, 16.6°, and 30.6°. In some embodiments, crystalline Formula I Besylate I has an XRPD pattern comprising any three degree 2θ-reflections (+/−0.2 degrees 2θ) selected from the group consisting of 8.4°, 19.4°, 25.0°, 13.9°, 16.6°, and 30.6°. In some embodiments, crystalline Formula I Besylate I has an XRPD pattern comprising any three degree 2θ-reflections (+/−0.2 degrees 2θ) selected from the group consisting of 8.4°, 12.3°, 13.9°, 16.6°, 17.5°, 18.8°, 19.4°, 21.4°, 22.2°, 24.0°, 25.0°, 26.5°, 30.6°, 33.5°, and 36.7°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 8.4°, 12.3°, 13.9°, 16.6°, 17.5°, 18.8°, 19.4°, 21.4°, 22.2°, 24.0°, 25.0°, 26.5°, 30.6°, 33.5°, and 36.7° and at least one, at least two, at least three, or all of the following properties:
an XRPD pattern substantially as shown in FIG. 15,
a DSC thermogram substantially as shown in FIG. 16, and
a TGA graph substantially as shown in FIG. 17.

Formula I Hemisulfate I

In some embodiments, provided is crystalline Formula I Hemisulfate I (crystalline Formula I Hemisulfate I), wherein the crystal structure exhibits an X-ray powder diffraction (XRPD) pattern substantially as shown in FIG. 18. Crystalline Formula I Hemisulfate I may exhibit a differential scanning calorimetry (DSC) thermogram substantially as shown in FIG. 19.

In some embodiments of crystalline Formula I Hemisulfate I, at least one, or all of the following (a)-(b) apply: (a) crystalline Formula I Hemisulfate I has an XRPD pattern substantially as shown in FIG. 18; (b) crystalline Formula I Hemisulfate I has a DSC thermogram substantially as shown in FIG. 19.

In some embodiments, crystalline Formula I Hemisulfate I has at least one, or all of the following properties:
an XRPD pattern substantially as shown in FIG. 18 and
a DSC thermogram substantially as shown in FIG. 19.

In some embodiments, crystalline Formula I Hemisulfate I has an XRPD pattern displaying at least two, at least three, at least four, at least five, or at least six of the degree 2θ-reflections with the greatest intensity as the XRPD pattern substantially as shown in FIG. 18.

In certain embodiments, crystalline Formula I Hemisulfate I has an XRPD pattern comprising degree 2θ-reflections (+/−0.2 degrees 2θ) at 3.4°, 7.6°, and 19.5°. In some embodiments, crystalline Formula I Hemisulfate I has an XRPD pattern comprising degree 2θ-reflections (+/−0.2 degrees 2θ) at 3.4°, 7.6°, and 19.5° and one or more of the degree 2θ-reflections (+/−0.2 degrees 2θ) at 4.8°, 21.7° and 22.3°. In some embodiments, crystalline Formula I Hemisulfate I has an XRPD pattern comprising degree 2θ-reflections (+/−0.2 degrees 2θ) at 3.4°, 7.6°, and 19.5° and one of the degree 2θ-reflections (+/−0.2 degrees 2θ) at 4.8°, 21.7° and 22.3°. In some embodiments, crystalline Formula I Hemisulfate I has an XRPD pattern comprising degree 2θ-reflections (+/−0.2 degrees 2θ) at 3.4°, 7.6°, and 19.5° and two of the degree 2θ-reflections (+/−0.2 degrees 2θ) at 4.8°, 21.7° and 22.3°. In some embodiments, crystalline Formula I Hemisulfate I has an XRPD pattern comprising degree 2θ-reflections (+/−0.2 degrees 2θ) at 3.4°, 7.6°, 19.5°, 4.8°, 21.7° and 22.3°. In some embodiments, crystalline Formula I Hemisulfate I has an XRPD pattern comprising any three degree 2θ-reflections (+/−0.2 degrees 2θ) selected from the group consisting of 3.4°, 7.6°, 19.5°, 4.8°, 21.7° and 22.3°. In some embodiments, crystalline Formula I Hemisulfate I has an XRPD pattern comprising any three degree 2θ-reflections (+/−0.2 degrees 2θ) selected from the group consisting of 3.4°, 4.8°, 7.6°, 8.7°, 9.7°, 10.2°, 12.1°, 13.0°, 14.1°, 15.5°, 17.0°, 17.5°, 18.9°, 19.5°, 20.8°, 21.7°, 22.3°, 22.9°, 23.9°, 25.0°, 25.8°, 26.3°, 28.4°, 29.3°, 31.1°, 31.7°, and 33.2°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 3.4°, 4.8°, 7.6°, 8.7°, 9.7°, 10.2°, 12.1°, 13.0°, 14.1°, 15.5°, 17.0°, 17.5°, 18.9°, 19.5°, 20.8°, 21.7°, 22.3°, 22.9°, 23.9°, 25.0°, 25.8°, 26.3°, 28.4°, 29.3°, 31.1°, 31.7°, and 33.2° and at least one, at least two, at least three, or all of the following properties:
an XRPD pattern substantially as shown in FIG. 18 and
a DSC thermogram substantially as shown in FIG. 19.

Formula I Napsylate I

In some embodiments, provided is crystalline Formula I Napsylate I (crystalline Formula I Napsylate I), wherein the crystal structure exhibits an X-ray powder diffraction (XRPD) pattern substantially as shown in FIG. 20. Crystalline Formula I Napsylate I may exhibit a differential scanning calorimetry (DSC) thermogram substantially as shown in FIG. 21.

In some embodiments of crystalline Formula I Napsylate I, at least one, or all of the following (a)-(b) apply: (a) crystalline Formula I Napsylate I has an XRPD pattern substantially as shown in FIG. 20; (b) crystalline Formula I Napsylate I has a DSC thermogram substantially as shown in FIG. 21.

In some embodiments, crystalline Formula I Napsylate I has at least one, or all of the following properties:
an XRPD pattern substantially as shown in FIG. 20, and
a DSC thermogram substantially as shown in FIG. 21.

In some embodiments, crystalline Formula I Napsylate I has an XRPD pattern displaying at least two, at least three, at least four, at least five, or at least six of the degree 2θ-reflections with the greatest intensity as the XRPD pattern substantially as shown in FIG. 20.

[A-Z]In certain embodiments, crystalline Formula I Napsylate I has an XRPD pattern comprising degree 2θ-reflections (+/−0.2 degrees 2θ) at 3.4°, 10.0°, and 20.0°. In some embodiments, crystalline Formula I Napsylate I has an XRPD pattern comprising degree 2θ-reflections (+/−0.2 degrees 2θ) at 3.4°, 10.0°, and 20.0° and one or more of the degree 2θ-reflections (+/−0.2 degrees 2θ) at 11.8°, 13.3°, and 23.4°. In some embodiments, crystalline Formula I Napsylate I has an XRPD pattern comprising degree 2θ-reflections (+/−0.2 degrees 2θ) at 3.4°, 10.0°, and 20.0° and one of the degree 2θ-reflections (+/−0.2 degrees 2θ) at 11.8°, 13.3°, and 23.4°. In some embodiments, crystalline Formula I Napsylate I has an XRPD pattern comprising degree 2θ-reflections (+/−0.2 degrees 2θ) at 3.4°, 10.0°, and 20.0° and two of the degree 2θ-reflections (+/−0.2 degrees 2θ) at 11.8°, 13.3°, and 23.4°. In some embodiments, crystalline Formula I Napsylate I has an XRPD pattern comprising degree 2θ-reflections (+/−0.2 degrees 2θ) at 3.4°, 10.0°, 20.0°, 11.8°, 13.3°, and 23.4°. In some embodiments, crystalline Formula I Napsylate I has an XRPD pattern comprising any three degree 2θ-reflections (+/−0.2 degrees 2θ) selected from the group consisting of 3.4°, 10.0°, 20.0°, 11.8°, 13.3°, and 23.4°. In some embodiments, crystalline Formula I Napsylate I has an XRPD pattern comprising any three degree 2θ-reflections (+/−0.2 degrees 2θ) selected from the group consisting of 3.4°, 6.7°, 8.0°, 10.1°, 11.8°, 13.3°, 16.3°, 16.7°, 17.9°, 20.0°, 21.1°, 23.4°, 25.6°, 26.8°, 28.1°, and 33.1°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 3.4°, 6.7°, 8.0°, 10.1°, 11.8°, 13.3°, 16.3°, 16.7°, 17.9°, 20.0°, 21.1°, 23.4°, 25.6°, 26.8°, 28.1°, and 33.1° and at least one, at least two, at least three, or all of the following properties:
- an XRPD pattern substantially as shown in FIG. 20, and
- a DSC thermogram substantially as shown in FIG. 21.

Formula I Hemiedisylate I

In some embodiments, provided is crystalline Formula I Hemiedisylate I (crystalline Formula I Hemiedisylate I), wherein the crystal structure exhibits an X-ray powder diffraction (XRPD) pattern substantially as shown in FIG. 22. Crystalline Formula I Hemiedisylate I may exhibit a differential scanning calorimetry (DSC) thermogram substantially as shown in FIG. 23.

In some embodiments of crystalline Formula I Hemiedisylate I, at least one, or all of the following (a)-(b) apply: (a) crystalline Formula I Hemiedisylate I has an XRPD pattern substantially as shown in FIG. 22; (b) crystalline Formula I Hemiedisylate I has a DSC thermogram substantially as shown in FIG. 23.

In some embodiments, crystalline Formula I Hemiedisylate I has at least one, or all of the following properties:
- an XRPD pattern substantially as shown in FIG. 22, and
- a DSC thermogram substantially as shown in FIG. 23.

In some embodiments, crystalline Formula I Hemiedisylate I has an XRPD pattern displaying at least two, at least three, at least four, at least five, or at least six of the degree 2θ-reflections with the greatest intensity as the XRPD pattern substantially as shown in FIG. 22.

In certain embodiments, crystalline Formula I Hemiedisylate I has an XRPD pattern comprising degree 2θ-reflections (+/−0.2 degrees 2θ) at 8.0°, 13.5°, and 24.2°. In some embodiments, crystalline Formula I Hemiedisylate I has an XRPD pattern comprising degree 2θ-reflections (+/−0.2 degrees 2θ) at 8.0°, 13.5°, and 24.2° and one or more of the degree 2θ-reflections (+/−0.2 degrees 2θ) at 16.1°, 18.8°, and 32.6°. In some embodiments, crystalline Formula I Hemiedisylate I has an XRPD pattern comprising degree 2θ-reflections (+/−0.2 degrees 2θ) at 8.0°, 13.5°, and 24.2° and one of the degree 2θ-reflections (+/−0.2 degrees 2θ) at 16.1°, 18.8°, and 32.6°. In some embodiments, crystalline Formula I Hemiedisylate I has an XRPD pattern comprising degree 2θ-reflections (+/−0.2 degrees 2θ) at 8.0°, 13.5°, and 24.2° and two of the degree 2θ-reflections (+/−0.2 degrees 2θ) at 16.1°, 18.8°, and 32.6°. In some embodiments, crystalline Formula I Hemiedisylate I has an XRPD pattern comprising degree 2θ-reflections (+/−0.2 degrees 2θ) at 8.0°, 13.5°, 24.2°, 16.1°, 18.8°, and 32.6°. In some embodiments, crystalline Formula I Hemiedisylate I has an XRPD pattern comprising any three degree 2θ-reflections (+/−0.2 degrees 2θ) selected from the group consisting of 8.0°, 13.5°, 24.2°, 16.1°, 18.8°, and 32.6°. In some embodiments, crystalline Formula I Hemiedisylate I has an XRPD pattern comprising any three degree 2θ-reflections (+/−0.2 degrees 2θ) selected from the group consisting of 5.4°, 8.0°, 9.1°, 10.7°, 13.5°, 14.9°, 16.1°, 18.8°, 21.5°, 24.2°, 27.0°, and 32.6°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 5.4°, 8.0°, 9.1°, 10.7°, 13.5°, 14.9°, 16.1°, 18.8°, 21.5°, 24.2°, 27.0°, and 32.6° and at least one, at least two, at least three, or all of the following properties:
- an XRPD pattern substantially as shown in FIG. 22, and
- a DSC thermogram substantially as shown in FIG. 23.

Formula I Tosylate I

In some embodiments, provided is crystalline Formula I Tosylate I (crystalline Formula I Tosylate I), wherein the crystal structure exhibits an X-ray powder diffraction (XRPD) pattern substantially as shown in FIG. 24. Crystalline Formula I Tosylate I may exhibit a differential scanning calorimetry (DSC) thermogram substantially as shown in FIG. 25.

In some embodiments of crystalline Formula I Tosylate I, at least one, or all of the following (a)-(b) apply: (a) crystalline Formula I Tosylate I has an XRPD pattern substantially as shown in FIG. 24; (b) crystalline Formula I Tosylate I has a DSC thermogram substantially as shown in FIG. 25.

In some embodiments, crystalline Formula I Tosylate I has at least one, or all of the following properties:
- an XRPD pattern substantially as shown in FIG. 24, and
- a DSC thermogram substantially as shown in FIG. 25.

In some embodiments, crystalline Formula I Tosylate I has an XRPD pattern displaying at least two, at least three, at least four, at least five, or at least six of the degree 2θ-reflections with the greatest intensity as the XRPD pattern substantially as shown in FIG. 24.

In certain embodiments, crystalline Formula I Tosylate I has an XRPD pattern comprising degree 2θ-reflections (+/−0.2 degrees 2θ) at 5.3°, 18.9°, and 23.6°. In some embodiments, crystalline Formula I Tosylate I has an XRPD pattern comprising degree 2θ-reflections (+/−0.2 degrees 2θ) at 5.3°, 18.9°, and 23.6° and one or more of the degree 2θ-reflections (+/−0.2 degrees 2θ) at 9.4°, 14.6°, and 21.3°. In some embodiments, crystalline Formula I Tosylate I has an XRPD pattern comprising degree 2θ-reflections (+/−0.2 degrees 2θ) at 5.3°, 18.9°, and 23.6° and one of the degree 2θ-reflections (+/−0.2 degrees 2θ) at 9.4°, 14.6°, and 21.3°. In some embodiments, crystalline Formula I Tosylate I has an XRPD pattern comprising degree 2θ-reflections (+/−0.2 degrees 2θ) at 5.3°, 18.9°, and 23.6° and two of the degree 2θ-reflections (+/−0.2 degrees 2θ) at 9.4°, 14.6°, and 21.3°. In some embodiments, crystalline Formula I Tosylate I has an XRPD pattern comprising degree 2θ-reflections (+/−0.2 degrees 2θ) at 5.3°, 18.9°, 23.6°, 9.4°, 14.6°, and 21.3°. In some embodiments, crystalline Formula I Tosylate I has an XRPD pattern comprising any three degree 2θ-reflections (+/−0.2 degrees 2θ) selected from the group consisting of 5.3°, 18.9°, 23.6°, 9.4°, 14.6°, and 21.3°. In some embodiments, crystalline Formula I Tosylate I has an XRPD pattern comprising any three degree 2θ-reflections (+/−0.2 degrees 2θ) selected from the group consisting of 5.3°, 6.7°, 9.4°, 10.5°, 11.7°, 12.5°, 13.8°, 14.3°, 14.6°, 15.0°, 16.8°, 17.3°, 18.9°, 19.7°, 20.7°, 21.3°, 22.1°, 23.3°, 23.6°, 24.5°, 25.2°, 26.8°, and 29.1°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 5.3°, 6.7°, 9.4°, 10.5°, 11.7°, 12.5°, 13.8°, 14.3°, 14.6°, 15.0°, 16.8°, 17.3°, 18.9°, 19.7°, 20.7°, 21.3°, 22.1°, 23.3°, 23.6°, 24.5°, 25.2°, 26.8°, and 29.1° and at least one, at least two, at least three, or all of the following properties:
- an XRPD pattern substantially as shown in FIG. 24, and
- a DSC thermogram substantially as shown in FIG. 25.

Formula I, Material A form

In some embodiments, provided is free base Formula I, material A (Formula I, Material A), wherein the crystal structure exhibits an X-ray powder diffraction (XRPD) pattern substantially as shown in FIG. 26. Material A is formed when Hydrate I, a labile hydrate, is dehydrated under vacuum, at elevated temperatures, or by a combination of elevated temperatures and vacuum. Formula I, Material A, may exhibit a differential scanning calorimetry (DSC) thermogram substantially as shown in FIG. 27. Formula I, Material A, may exhibit a thermogravimetric analysis (TGA) thermogram substantially as shown in FIG. 28. In some embodiments, Formula I Material A has less than about 0.2 equivalents of water. In some embodiments, Formula I Hydrate I has approximately 0.05-0.2, or approximately 0.1-0.2.

In some embodiments of Formula I, Material A, at least one, at least two, at least three, or all of the following (a)-(c) apply: (a) Formula I, Material A has an XRPD pattern substantially as shown in FIG. 26; (b) Formula I, Material A has a DSC thermogram substantially as shown in FIG. 27; (c) Formula I, Material A has a TGA graph substantially as shown in FIG. 28.

In some embodiments, Formula I, Material A has at least one, at least two, at least three, or all of the following properties:
an XRPD pattern substantially as shown in FIG. 26,
a DSC thermogram substantially as shown in FIG. 27, and
a TGA graph substantially as shown in FIG. 28.

In some embodiments, Formula I, Material A form has an XRPD pattern displaying at least two, at least three, at least four, at least five, or at least six of the degree 2θ-reflections with the greatest intensity as the XRPD pattern substantially as shown in FIG. 26.

In certain embodiments, Formula I, Material A has an XRPD pattern comprising degree 2θ-reflection (+/−0.2 degrees 2θ) at 5.2°, 11.7°, and 18.2°. In some embodiments, Formula I, Material A has an XRPD pattern comprising degree 2θ-reflections (+/−0.2 degrees 2θ) at 5.2°, 11.7°, and 18.2°, and one or more of the degree 2θ-reflections (+/−0.2 degrees 2θ) at 7.1°, 9.9° and 19.2°. In some embodiments, Formula I, Material A has an XRPD pattern comprising degree 2θ-reflections (+/−0.2 degrees 2θ) at 5.2°, 11.7°, and 18.2°, and one of the degree 2θ-reflections (+/−0.2 degrees 2θ) at 10.6°, 20.6° and 28.7°. In some embodiments, Formula I, Material A has an XRPD pattern comprising degree 2θ-reflections (+/−0.2 degrees 2θ) at 7.1°, 9.9° and 19.2°, and one of the degree 2θ-reflections (+/−0.2 degrees 2θ) at 10.6°, 20.6° and 28.7°. In some embodiments, Formula I, Material A has an XRPD pattern comprising degree 2θ-reflections (+/−0.2 degrees 2θ) at 5.2°, 11.7°, and 18.2°, one of the degree 2θ-reflections (+/−0.2 degrees 2θ) at 7.1°, 9.9° and 19.2°, and one of the degree 2θ-reflections (+/−0.2 degrees 2θ) at 10.6°, 20.6° and 28.7°. In some embodiments, Formula I, Material A has an XRPD pattern comprising degree 2θ-reflections (+/−0.2 degrees 2θ) at 5.2°, 11.7°, 18.2°, 7.1°, 9.9°, 19.2°, 10.6°, 20.6°, and 28.7°. In some embodiments, Formula I, Material A has an XRPD pattern comprising any three degree 2θ-reflections (+/−0.2 degrees 2θ) selected from the group consisting of 5.2°, 11.7°, 18.2°, 7.1°, 9.9°, 19.2°, 10.6°, 20.6°, and 28.7°. In some embodiments, Formula I, Material A has an XRPD pattern comprising any three degree 2θ-reflections (+/−0.2 degrees 2θ) selected from the group consisting of 5.2°, 7.1°, 7.6°, 8.3°, 9.9°, 10.6°, 11.7°, 13.5°, 14.1°, 15.9°, 16.8°, 17.6°, 18.2°, 18.4°, 18.8°, 19.2°, 19.8°, 20.6°, 21.3°, 21.6°, 22.6°, 23.1°, 23.4°, 24.7°, 25.1°, 25.7°, 26.2°, 26.8°, 27.4°, 28.7°, 29.7°, 31.7°, 32.0°, 35.3°, 36.5°, and 37.4°. In some embodiments, Formula I, Material A form has an XRPD pattern comprising any six degree 2θ-reflections (+/−0.2 degrees 2θ) selected from the group consisting of 5.2°, 7.1°, 7.6°, 8.3°, 9.9°, 10.6°, 11.7°, 13.5°, 14.1°, 15.9°, 16.8°, 17.6°, 18.2°, 18.4°, 18.8°, 19.2°, 19.8°, 20.6°, 21.3°, 21.6°, 22.6°, 23.1°, 23.4°, 24.7°, 25.1°, 25.7°, 26.2°, 26.8°, 27.4°, 28.7°, 29.7°, 31.7°, 32.0°, 35.3°, 36.5°, and 37.4°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 5.2°, 7.1°, 7.6°, 8.3°, 9.9°, 10.6°, 11.7°, 13.5°, 14.1°, 15.9°, 16.8°, 17.6°, 18.2°, 18.4°, 18.8°, 19.2°, 19.8°, 20.6°, 21.3°, 21.6°, 22.6°, 23.1°, 23.4°, 24.7°, 25.1°, 25.7°, 26.2°, 26.8°, 27.4°, 28.7°, 29.7°, 31.7°, 32.0°, 35.3°, 36.5°, and 37.4° and at least one, at least two, at least three, or all of the following properties:
an XRPD pattern substantially as shown in FIG. 26,
a DSC thermogram substantially as shown in FIG. 27, and
a TGA graph substantially as shown in FIG. 28.

Solvated Darunavir (Formula I, MEK solvate)

In some embodiments, provided is a methyl ethyl ketone (MEK) solvated form of darunavir (Formula I, MEK solvate), wherein the crystal structure exhibits an X-ray powder diffraction (XRPD) pattern substantially as shown in FIG. 29. Formula I, MEK solvate, may exhibit a differential scanning calorimetry (DSC) thermogram substantially as shown in FIG. 30. Formula I, MEK solvate, may exhibit a thermogravimetric analysis (TGA) thermogram substantially as shown in FIG. 31.

In some embodiments of Formula I, MEK solvate, at least one, at least two, at least three, or all of the following (a)-(c) apply: (a) Formula I, MEK solvate has an XRPD pattern substantially as shown in FIG. 29; (b) Formula I, MEK solvate has a DSC thermogram substantially as shown in FIG. 30; (c) Formula I, MEK solvate has a TGA graph substantially as shown in FIG. 31.

In some embodiments, Formula I, MEK solvate has at least one, at least two, at least three, or all of the following properties:
an XRPD pattern substantially as shown in FIG. 29,
a DSC thermogram substantially as shown in FIG. 30, and
a TGA graph substantially as shown in FIG. 31.

In some embodiments, Formula I MEK solvate has an XRPD pattern displaying at least two, at least three, at least four, at least five, or at least six of the degree 2θ-reflections with the greatest intensity as the XRPD pattern substantially as shown in FIG. 29.

In certain embodiments, Formula I, MEK solvate has an XRPD pattern comprising degree 2θ-reflection (+/−0.2 degrees 2θ) at 7.1°, 13.9°, and 21.3°. In some embodiments, Formula I, MEK solvate has an XRPD pattern comprising degree 2θ-reflections (+/−0.2 degrees 2θ) at 7.1°, 13.9°, and 21.3°, and one or more of the degree 2θ-reflections (+/−0.2 degrees 2θ) at 16.8°, 20.7° and 23.0°. In some embodiments, Formula I, MEK solvate has an XRPD pattern comprising degree 2θ-reflections (+/−0.2 degrees 2θ) at 7.1°, 13.9°, and 21.3°, and one or more of the degree 2θ-reflections (+/−0.2 degrees 2θ) at 17.5°, 19.3°, and 28.2°. In some embodiments, Formula I, MEK solvate has an XRPD pattern comprising degree 2θ-reflections (+/−0.2 degrees 2θ) at 16.8°, 20.7° and 23.0°, and one or more of the degree 2θ-reflections (+/−0.2 degrees 2θ) at 17.5°, 19.3°, and 28.2°. In some embodiments, Formula I, MEK solvate has an XRPD pattern comprising degree 2θ-reflections (+/−0.2 degrees 2θ) at 7.1°, 13.9°, and 21.3°, one or more of the degree 2θ-reflections (+/−0.2 degrees 2θ) at 16.8°, 20.7° and 23.0°, and one or more of the degree 2θ-reflections (+/−0.2 degrees 2θ) at 17.5°, 19.3°, and 28.2°. In some embodiments, Formula I, MEK solvate has an XRPD pattern comprising degree 2θ-reflections (+/−0.2 degrees 2θ) at 7.1°, 13.9°, 21.3°, 16.8°, 20.7°, 23.0°, 17.5°, 19.3°, and 28.2°. In some embodiments, Formula I, MEK solvate has an XRPD pattern comprising any three degree 2θ-reflections (+/−0.2 degrees 2θ) selected from the group consisting of 7.1°, 13.9°, 21.3°, 16.8°, 20.7°, 23.0°, 17.5°, 19.3°, and 28.2°. In some embodiments, crystalline MEK solvate of Formula I has an XRPD pattern comprising any three degree 2θ-reflections (+/−0.2 degrees 2θ) selected from the group consisting of 7.1°, 9.4°, 10.5°, 10.8°, 11.4°, 13.0°, 13.7°, 14.1°, 14.5°, 15.0°, 16.6°, 17.5°, 18.8°, 19.1°, 19.6°, 20.1°, 20.8°, 21.1°, 21.5°, 22.6°, 22.9°, 23.3°, 25.0°, 25.5°, 26.1°, 27.2°, 27.9°, 28.2°, 28.7°, 29.1°, 29.8°, 31.4°, 33.6°, 36.4°, 37.7°, and 39.1°. In some embodiments, Formula I, MEK solvate has an XRPD pattern comprising any six degree 2θ-reflections (+/−0.2 degrees 2θ) selected from the group consisting of 7.1°, 9.4°, 10.5°, 10.8°, 11.4°, 13.0°, 13.7°, 14.1°, 14.5°, 15.0°, 16.6°, 17.5°, 18.8°, 19.1°, 19.6°, 20.1°, 20.8°, 21.1°, 21.5°, 22.6°, 22.9°, 23.3°, 25.0°, 25.5°, 26.1°, 27.2°, 27.9°, 28.2°, 28.7°, 29.1°, 29.8°, 31.4°, 33.6°, 36.4°, 37.7°, and 39.1°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 7.1°, 9.4°, 10.5°, 10.8°, 11.4°, 13.0°, 13.7°, 14.1°, 14.5°, 15.0°, 16.6°, 17.5°, 18.8°, 19.1°, 19.6°, 20.1°, 20.8°, 21.1°, 21.5°, 22.6°, 22.9°, 23.3°, 25.0°, 25.5°, 26.1°, 27.2°, 27.9°, 28.2°, 28.7°, 29.1°, 29.8°, 31.4°, 33.6°, 36.4°, 37.7°, and 39.1° and at least one, at least two, at least three, or all of the following properties:

an XRPD pattern substantially as shown in FIG. 29,
a DSC thermogram substantially as shown in FIG. 30, and
a TGA graph substantially as shown in FIG. 31.

Solvated Darunavir (Formula I, MeTHF Solvate)

In some embodiments, provided is a methyl tetrahydrofuran solvated form of darunavir (Formula I, MeTHF solvate), wherein the crystal structure exhibits an X-ray powder diffraction (XRPD) pattern substantially as shown in FIG. 32. Formula I, MeTHF solvate may exhibit a differential scanning calorimetry (DSC) thermogram substantially as shown in FIG. 33. Formula I, MeTHF solvate may exhibit a thermogravimetric analysis (TGA) thermogram substantially as shown in FIG. 34.

In some embodiments of Formula I, MeTHF solvate, at least one, at least two, at least three, or all of the following (a)-(c) apply: (a) Formula I, MeTHF solvate has an XRPD pattern substantially as shown in FIG. 32; (b) Formula I, MeTHF solvate has a DSC thermogram substantially as shown in FIG. 33; (c) Formula I, MeTHF solvate has a TGA graph substantially as shown in FIG. 34.

In some embodiments, Formula I, MeTHF solvate has at least one, at least two, at least three, or all of the following properties:

an XRPD pattern substantially as shown in FIG. 32,
a DSC thermogram substantially as shown in FIG. 33, and
a TGA graph substantially as shown in FIG. 34.

In some embodiments, Formula I, MeTHF solvate has an XRPD pattern displaying at least two, at least three, at least four, at least five, or at least six of the degree 2θ-reflections with the greatest intensity as the XRPD pattern substantially as shown in FIG. 32.

In certain embodiments, Formula I, MeTHF solvate has an XRPD pattern comprising degree 2θ-reflection (+/−0.2 degrees 2θ) at 7.1°, 20.4°, and 22.7°. In some embodiments, Formula I, MeTHF solvate has an XRPD pattern comprising degree 2θ-reflections (+/−0.2 degrees 2θ) at 7.1°, 20.4°, and 22.7°, and one or more of the degree 2θ-reflections (+/−0.2 degrees 2θ) at 10.5°, 13.7° and 16.5°. In some embodiments, Formula I, MeTHF solvate has an XRPD pattern comprising degree 2θ-reflections (+/−0.2 degrees 2θ) at 7.1°, 20.4°, and 22.7°, and one of the degree 2θ-reflections (+/−0.2 degrees 2θ) at 11.3°, 17.2°, and 21.1°. In some embodiments, Formula I, MeTHF solvate has an XRPD pattern comprising degree 2θ-reflections (+/−0.2 degrees 2θ) at 10.5°, 13.7° and 16.5°, and one or more of the degree 2θ-reflections (+/−0.2 degrees 2θ) at 11.3°, 17.2°, and 21.1°. In some embodiments, Formula I, MeTHF solvate has an XRPD pattern comprising degree 2θ-reflections (+/−0.2 degrees 2θ) at 7.1°, 20.4°, and 22.7°, one of the degree 2θ-reflections (+/−0.2 degrees 2θ) at 10.5°, 13.7° and 16.5°, and one of the degree 2θ-reflections (+/−0.2 degrees 2θ) at 11.3°, 17.2°, and 21.1°. In some embodiments, Formula I, MeTHF solvate has an XRPD pattern comprising degree 2θ-reflections (+/−0.2 degrees 2θ) at 7.1°, 20.4°, 22.7°, 10.5°, 13.7°, 16.5°, 11.3°, 17.2°, and 21.1°. In some embodiments, Formula I, MeTHF solvate has an XRPD pattern comprising any three degree 2θ-reflections (+/−0.2 degrees 2θ) selected from the group consisting of 7.1°, 20.4°, 22.7°, 10.5°, 13.7°, 16.5°, 11.3°, 17.2°, and 21.1°. In some embodiments, Formula I, MeTHF solvate has an XRPD pattern comprising any three degree 2θ-reflections (+/−0.2 degrees 2θ) selected from the group consisting of 7.1°, 9.2°, 10.5°, 11.3°, 13.7°, 14.0°, 14.5°, 14.8°, 16.5°, 17.2°, 18.6°, 19.0°, 19.5°, 20.4°, 21.1°, 21.4°, 22.7°, 23.3°, 25.4°, 26.9°, 27.5°, 27.9°, 29.0°, 29.7°, and 33.2°. In some embodiments, Formula I, MeTHF solvate has an XRPD pattern comprising any six degree 2θ-reflections (+/−0.2 degrees 2θ) selected from the group consisting of 7.1°, 9.2°, 10.5°, 11.3°, 13.7°, 14.0°, 14.5°, 14.8°, 16.5°, 17.2°, 18.6°, 19.0°, 19.5°, 20.4°, 21.1°, 21.4°, 22.7°, 23.3°, 25.4°, 26.9°, 27.5°, 27.9°, 29.0°, 29.7°, and 33.2°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 7.1°, 9.2°, 10.5°, 11.3°, 13.7°, 14.0°, 14.5°, 14.8°, 16.5°, 17.2°, 18.6°, 19.0°, 19.5°, 20.4°, 21.1°, 21.4°, 22.7°, 23.3°, 25.4°, 26.9°, 27.5°, 27.9°, 29.0°, 29.7°, and 33.2° and at least one, at least two, at least three, or all of the following properties:

an XRPD pattern substantially as shown in FIG. 32,
a DSC thermogram substantially as shown in FIG. 33, and
a TGA graph substantially as shown in FIG. 34.

Formula I, MeOAc Solvate

In some embodiments, provided is a methyl acetate solved form of darunavir (Formula I, MeOAc solvate), wherein the crystal structure exhibits an X-ray powder diffraction (XRPD) pattern substantially as shown in FIG. 35. Formula I, MeOAc solvate form may exhibit a differential scanning calorimetry (DSC) thermogram substantially as shown in FIG. 36. Formula I, MeOAC solvate form may exhibit a thermogravimetric analysis (TGA) thermogram substantially as shown in FIG. 37.

In some embodiments of Formula I, MeOAc solvate form, at least one, at least two, at least three, or all of the following (a)-(c) apply: (a) Formula I, MeOAc solvate form has an XRPD pattern substantially as shown in FIG. 35; (b) free base Formula I, MeOAc solvate form has a DSC thermogram substantially as shown in FIG. 36; (c) free base Formula I, MeOAC solvate form of Formula I has a TGA graph substantially as shown in FIG. 37.

In some embodiments, Formula I, MeOAc solvate form has at least one, at least two, at least three, or all of the following properties:

an XRPD pattern substantially as shown in FIG. 35,
a DSC thermogram substantially as shown in FIG. 36, and
a TGA graph substantially as shown in FIG. 37.

In some embodiments, Formula I, MeOAc solvate form has an XRPD pattern displaying at least two, at least three, at least four, at least five, or at least six of the degree 2θ-reflections with the greatest intensity as the XRPD pattern substantially as shown in FIG. 35. In certain embodiments, Formula I, MeOAc solvate has an XRPD pattern comprising degree 2θ-reflection (+/−0.2 degrees 2θ) at 7.2°, 13.8°, and 17.6°. In some embodiments, Formula I, MeOAc solvate has an XRPD pattern comprising degree 2θ-reflections (+/−0.2 degrees 2θ) at 7.2°, 13.8°, and 17.6°, and one or more of the degree 2θ-reflections (+/−0.2 degrees 2θ) at 9.5°, 16.7° and 21.3°. In some embodiments, Formula I, MeOAc solvate has an XRPD pattern comprising degree 2θ-reflections (+/−0.2 degrees 2θ) at 7.2°, 13.8°, and 17.6°, and one of the degree 2θ-reflections (+/−0.2 degrees 2θ) at 11.4°, 22.9°, and 29.3°. In some embodiments, Formula I, MeOAc solvate has an XRPD pattern comprising degree 2θ-reflections (+/−0.2 degrees 2θ) at 9.5°, 16.7° and 21.3°, and one or more of the degree 2θ-reflections (+/−0.2 degrees 2θ) at 9.5°, 16.7° and 21.3°. In some embodiments, Formula I, MeOAc solvate has an XRPD pattern comprising degree 2θ-reflections (+/−0.2 degrees 2θ) at 7.2°, 13.8°, and 17.6°, one or more of the degree 2θ-reflections (+/−0.2 degrees 2θ) at 9.5°, 16.7° and 21.3°, and one or more of the degree 2θ-reflections (+/−0.2 degrees 2θ) at 11.4°, 22.9°, and 29.3°. In some embodiments, Formula I, MeOAc solvate has an XRPD pattern comprising degree 2θ-reflections (+/−0.2 degrees 2θ) at 7.2°, 13.8°, and 17.6°, one of the degree 2θ-reflections (+/−0.2 degrees 2θ) at 9.5°, 16.7° and 21.3°, and one of the degree 2θ-reflections (+/−0.2 degrees 2θ) at 11.4°, 22.9°, and 29.3°. In some embodiments, Formula I, MeOAc solvate has an XRPD pattern comprising degree 2θ-reflections (+/−0.2 degrees 2θ) at 7.2°, 13.8°, 17.6°, 9.5°, 16.7°, 21.3°, 11.4°, 22.9°, and 29.3°. In some embodiments, MeOAc solvate of Formula I has an XRPD pattern comprising any three degree 2θ-reflections (+/−0.2 degrees 2θ) selected from the group consisting of 7.2°, 13.8°, 17.6°, 9.5°, 16.7°, 21.3°, 11.4°, 22.9°, and 29.3°. In some embodiments, MeOAc solvate of Formula I has an XRPD pattern comprising any three degree 2θ-reflections (+/−0.2 degrees 2θ) selected from the group consisting of 7.2°, 9.5°, 10.2°, 10.5°, 11.4°, 13.0°, 13.8°, 14.2°, 15.1°, 16.7°, 17.6°, 18.9°, 19.2°, 19.7°, 20.3°, 20.9°, 21.3°, 21.5°, 22.9°, 23.4°, 25.6°, 27.4°, 28.0°, 28.5°, 29.3°, 29.9°, 30.4°, 31.4°, 35.6°, and 36.5°. In some embodiments, MeOAc solvate form of Formula I has an XRPD pattern comprising any six degree 2θ-reflections (+/−0.2 degrees 2θ) selected from the group consisting of 7.2°, 9.5°, 10.2°, 10.5°, 11.4°, 13.0°, 13.8°, 14.2°, 15.1°, 16.7°, 17.6°, 18.9°, 19.2°, 19.7°, 20.3°, 20.9°, 21.3°, 21.5°, 22.9°, 23.4°, 25.6°, 27.4°, 28.0°, 28.5°, 29.3°, 29.9°, 30.4°, 31.4°, 35.6°, and 36.5°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 7.2°, 9.5°, 10.2°, 10.5°, 11.4°, 13.0°, 13.8°, 14.2°, 15.1°, 16.7°, 17.6°, 18.9°, 19.2°, 19.7°, 20.3°, 20.9°, 21.3°, 21.5°, 22.9°, 23.4°, 25.6°, 27.4°, 28.0°, 28.5°, 29.3°, 29.9°, 30.4°, 31.4°, 35.6°, and 36.5°, 29.7°, and 33.2° and at least one, at least two, at least three, or all of the following properties:
   an XRPD pattern substantially as shown in FIG. 35,
   a DSC thermogram substantially as shown in FIG. 36, and
   a TGA graph substantially as shown in FIG. 37.

Formula I, Ethyl Formate Solvate

In some embodiments, provided is an ethyl formate solvated form of darunavir (Formula I, ethyl formate solvate), wherein the crystal structure exhibits an X-ray powder diffraction (XRPD) pattern substantially as shown in FIG. 38. Formula I, ethyl formate solvate may exhibit a differential scanning calorimetry (DSC) thermogram substantially as shown in FIG. 39. Formula I, ethyl formate solvate may exhibit a thermogravimetric analysis (TGA) thermogram substantially as shown in FIG. 40.

In some embodiments of Formula I, ethyl formate solvate, at least one, at least two, at least three, or all of the following (a)-(c) apply: (a) Formula I, ethyl formate has an XRPD pattern substantially as shown in FIG. 38; (b) Formula I, ethyl formate has a DSC thermogram substantially as shown in FIG. 39; (c) Formula I, ethyl formate has a TGA graph substantially as shown in FIG. 40.

In some embodiments, Formula I, ethyl formate solvate has at least one, at least two, at least three, or all of the following properties:
   an XRPD pattern substantially as shown in FIG. 38,
   a DSC thermogram substantially as shown in FIG. 39, and
   a TGA graph substantially as shown in FIG. 40.

In some embodiments, Formula I, ethyl formate solvate has an XRPD pattern displaying at least two, at least three, at least four, at least five, or at least six of the degree 2θ-reflections with the greatest intensity as the XRPD pattern substantially as shown in FIG. 38.

In certain embodiments, Formula I, ethyl formate solvate has an XRPD pattern comprising degree 2θ-reflection (+/−0.2 degrees 2θ) at 7.2°, 14.0°, and 17.6°. In some embodiments, Formula I, ethyl formate solvate has an XRPD pattern comprising degree 2θ-reflections (+/−0.2 degrees 2θ) at 7.2°, 14.0°, and 17.6°, and one or more of the degree 2θ-reflections (+/−0.2 degrees 2θ) at 9.5°, 16.6° and 21.4°. In some embodiments, Formula I, ethyl formate solvate has an XRPD pattern comprising degree 2θ-reflections (+/−0.2 degrees 2θ) at 7.2°, 14.0°, and 17.6°, and one of the degree 2θ-reflections (+/−0.2 degrees 2θ) at 11.5°, 20.9°, and 22.9°. In some embodiments, Formula I, ethyl formate solvate has an XRPD pattern comprising degree 2θ-reflections (+/−0.2 degrees 2θ) at 9.5°, 16.6° and 21.4°, and one or more of the degree 2θ-reflections (+/−0.2 degrees 2θ) at 11.5°, 20.9°, and 22.9°. In some embodiments, free base Formula I, ethyl formate solvate has an XRPD pattern comprising degree 2θ-reflections (+/−0.2 degrees 2θ) at 7.2°, 14.0°, and 17.6°, one of the degree 2θ-reflections (+/−0.2 degrees 2θ) at 9.5°, 16.6° and 21.4°, and one of the degree 2θ-reflections (+/−0.2 degrees 2θ) at 11.5°, 20.9°, and 22.9°. In some embodiments, Formula I, ethyl formate solvate has an XRPD pattern comprising degree 2θ-reflections (+/−0.2 degrees 2θ) at 7.2°, 14.0°, 17.6°, 9.5°, 16.6°, 21.4°, 11.5°, 20.9°, and 22.9°. In some embodiments, ethyl formate solvate of Formula I has an XRPD pattern comprising any three degree 2θ-reflections (+/−0.2 degrees 2θ) selected from the group consisting of 7.2°, 14.0°, 17.6°, 9.5°, 16.6°, 21.4°, 11.5°, 20.9°, and 22.9°. In some embodiments, Formula I, ethyl formate solvate has an XRPD pattern comprising any three degree 2θ-reflections (+/−0.2 degrees 2θ) selected from the group consisting of 7.2°, 9.5°, 10.2°, 10.5°, 10.8°, 11.5°, 13.1°, 14.0°, 16.6°, 17.6°, 18.9°, 19.4°, 20.3°, 20.9°, 21.4°, 21.4°, 22.9°, 23.4°, 24.5°, 26.1°, 26.6°, 27.4°, 28.0°, 28.5°, 29.5°, 30.6°, 31.7°, 32.8°, and 34.9°. In some embodiments, Formula I, ethyl formate solvate has an XRPD pattern comprising any six degree 2θ-reflections (+/−0.2 degrees 2θ) selected from the group consisting of 7.2°, 9.5°, 10.2°, 10.5°, 10.8°, 11.5°, 13.1°, 14.0°, 16.6°, 17.6°, 18.9°, 19.4°, 20.3°, 20.9°, 21.4°, 22.9°, 23.4°, 24.5°, 26.1°, 26.6°, 27.4°, 28.0°, 28.5°, 29.5°, 30.6°, 31.7°, 32.8°, and 34.9°.

In some embodiments, crystalline Formula I Form I has an XRPD pattern comprising any two, three, four, five, six, seven, eight, nine or ten degree 2θ-reflections (+/−0.2 degrees 2θ) selected from the group consisting of 7.2°, 9.5°, 10.2°, 10.5°, 10.8°, 11.5°, 13.1°, 14.0°, 16.6°, 17.6°, 18.9°, 19.4°, 20.3°, 20.9°, 21.4°, 21.4°, 22.9°, 23.4°, 24.5°, 26.1°, 26.6°, 27.4°, 28.0°, 28.5°, 29.5°, 30.6°, 31.7°, 32.8°, and 34.9° and at least one, at least two, at least three, or all of the following properties:

an XRPD pattern substantially as shown in FIG. 38,
a DSC thermogram substantially as shown in FIG. 39, and
a TGA graph substantially as shown in FIG. 40.

Pharmaceutical Compositions

For the purposes of administration, in certain embodiments, the compounds described herein are administered as a raw chemical or are formulated as pharmaceutical compositions. Pharmaceutical compositions of the present invention comprise a therapeutically effective amount of a compound of Formula I, and a pharmaceutically acceptable excipient. The compound of Formula I is present in the composition in an amount which is effective to treat a particular disease or condition of interest. The activity of compounds of Formula I can be determined by one skilled in the art, for example, as described herein. Appropriate therapeutically effective concentrations and dosages can be readily determined by one skilled in the art. In certain embodiments, a compound of Formula I is present in the pharmaceutical composition in an amount from about 320 mg and 1,280 mg. In certain embodiments, a compound of Formula I is present in the pharmaceutical composition in an amount from about 790 mg and 810 mg. In certain embodiments, a compound of Formula I is present in the pharmaceutical composition in an amount from about 795 mg and 805 mg. In certain embodiments, a compound of Formula I is present in the pharmaceutical composition in an amount from about 75 mg to about 800 mg. In certain embodiments, a compound of Formula I is present in the pharmaceutical composition in an amount of about 75 mg. In certain embodiments, a compound of Formula I is present in the pharmaceutical composition in an amount of about 100 mg. In certain embodiments, a compound of Formula I is present in the pharmaceutical composition in an amount of about 150 mg. In certain embodiments, a compound of Formula I is present in the pharmaceutical composition in an amount of about 300 mg. In certain embodiments, a compound of Formula I is present in the pharmaceutical composition in an amount of about 400 mg. In certain embodiments, a compound of Formula I is present in the pharmaceutical composition in an amount of about 600 mg. In certain embodiments, a compound of Formula I is present in the pharmaceutical composition in an amount of about 800 mg. In certain embodiments, a compound of Formula I is present in the pharmaceutical composition in an amount of about 75 mg, 100 mg, 150 mg, 300 mg, 400 mg, 600 mg, or about 800 mg. In certain embodiments, a compound of Formula I is present in the pharmaceutical composition in an amount of about 800 mg.

Administration of the compounds of the invention in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. The pharmaceutical compositions of the invention can be prepared by combining a compound of the invention with an appropriate pharmaceutically acceptable excipient, and may be formulated into preparations in solid, semi-solid, liquid or gaseous forms, such as solid dispersions and solid solutions. Typical routes of administering such pharmaceutical compositions include, without limitation, oral, topical, transdermal, inhalation, parenteral, sublingual, buccal, rectal, vaginal, and intranasal. In a specific embodiment, the pharmaceutical composition is a tablet. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention for treatment of a disease or condition of interest in accordance with the teachings of this invention.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant or other solubilizing excipient may be added to facilitate the formation of a homogeneous solution or suspension. Surfactants are compounds that non-covalently interact with the compound of the invention so as to facilitate dissolution or homogeneous suspension of the compound in the aqueous delivery system.

In other embodiments, a solid pharmaceutical composition intended for oral administration can be prepared by mixing a therapeutically effective amount of a compound of the invention with at least one suitable pharmaceutically acceptable excipient to form a solid preformulation composition, which then may be readily subdivided into equally effective unit dosage forms such as tablets, pills and capsules. Accordingly, in some embodiments, a pharmaceutical composition is provided, which includes a therapeutically effective amount of a compound of Formula I and a pharmaceutically acceptable excipient.

The compounds of the invention are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some embodiments, the compounds of the invention can be administered alone or in combination with other antiviral agents one time a day, or two times a day, or three times a day, or four times a day, for as long as the patient is infected, latently infected, or to prevent infection (e.g. for multiple years, months, weeks, or days).

Provided are also compositions comprising a compound of Formula I as described herein. In a particular embodiment, a composition comprising one of the compounds of Formula I described herein is provided. In a particular embodiment, a composition comprising two of the compounds of Formula I described herein is provided. In a particular embodiment, a composition comprising three of the compounds of Formula I described herein is provided. In a particular embodiment, a composition comprising four of the compounds of Formula I described herein is provided. In other embodiments, the compositions described herein may comprise substantially pure crystalline forms, or may be substantially free of other crystalline forms and/or impurities.

In some embodiments, the composition comprises a crystalline form of Formula I. In certain embodiments are provided compositions comprising a crystalline form as described herein, wherein the Formula I within the composition is substantially pure (i.e., substantially pure Formula I Form I, Formula I Acetic Acid Solvate, Formula I Hydrate I Formula I Esylate I, Formula I Besylate I, Formula I Hemisulfate I, Formula I Napsylate I, Formula I Hemiedisylate I, Formula I Tosylate I, Formula I, Material A, Formula I MEK solvate, Formula I MeTHF solvate, Formula I MeOAc solvate, and Formula I ethyl formate solvate described herein). In particular embodiments of compositions comprising a crystalline form of Formula I, at least about 50%, at least about 60%, at least about 70%, at least about 80%, at least about 85%, at least about 90%, at least about 95%, at least about 96%, at least about 97%, at least about 98%, or at least about 99% of Formula I present in the composition is one of the crystalline forms disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the crystalline forms of Formula I.

In other embodiments of compositions comprising a crystalline form disclosed herein, less than about 50%, less than about 40%, less than about 30%, less than about 20%, less than about 10%, less than about 5%, less than about 4%, less than about 3%, less than about 2% or less than about 1% of Formula I present in the composition are other amorphous or crystal forms of Formula I and/or impurities.

In yet other embodiments of compositions comprising the crystalline forms disclosed herein, impurities make up less than about 5%, less than about 4%, less than about 3%, less than about 2% or less than about 1% of the total mass relative to the mass of the crystalline forms present. Impurities may, for example, include by-products from synthesizing Formula I, contaminants, degradation products, other crystalline forms, amorphous form, water, and solvents. In certain embodiments, impurities include by-products from the process of synthesizing Formula I. In certain embodiments, impurities include contaminants from the process of synthesizing Formula I. In certain embodiments, impurities include degradation products of Formula I. In certain embodiments, impurities include other crystalline forms of Formula I. In certain embodiments, impurities include other crystalline forms of Formula I and/or amorphous forms of Formula I. In certain embodiments, impurities include water or solvent. In certain embodiments of compositions comprising a crystalline form disclosed herein, impurities are selected from the group consisting of by-products from synthesizing Formula I, contaminants, degradation products, other crystalline forms, amorphous forms, water, solvents and combinations thereof.

Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, or four; or one or two; or one to three; or one to four) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, or four; or one or two; or one to three; or one to four) additional therapeutic agents.

In one embodiment, pharmaceutical compositions comprising a compound disclosed herein, or a pharmaceutically acceptable salt thereof, in combination with one or more (e.g., one, two, three, or four; or one or two; or one to three; or one to four) additional therapeutic agents, and a pharmaceutically acceptable carrier, diluent, or excipient are provided.

In certain embodiments, the present disclosure provides a method for treating an HIV infection, comprising administering to a subject in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein, or a pharmaceutically acceptable salt thereof, is administered with one or more additional therapeutic agents. Co-administration of a compound disclosed herein, or a pharmaceutically acceptable salt thereof, with one or more additional therapeutic agents generally refers to simultaneous or sequential administration of a compound disclosed herein and one or more additional therapeutic agents, such that therapeutically effective amounts of the compound disclosed herein, or a pharmaceutically acceptable salt thereof, and the one or more additional therapeutic agents are both present in the body of the subject. When administered sequentially, the combination may be administered in two or more administrations.

Co-administration includes administration of unit dosages of the compounds disclosed herein, or pharmaceutically acceptable salts thereof, before or after administration of unit dosages of one or more additional therapeutic agents. For example, the compound disclosed herein, or a pharmaceutically acceptable salt thereof, may be administered within seconds, minutes, or hours of the administration of the one or more additional therapeutic agents. In some embodiments, a unit dose of a compound disclosed herein, or a pharmaceutically acceptable salt thereof, is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein, or a pharmaceutically acceptable salt thereof, is combined with one or more additional therapeutic agents in a unitary dosage form for simultaneous administration to a subject. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

In certain embodiments, a compound disclosed herein, or a pharmaceutically acceptable salt thereof, is formulated as a tablet, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof. In certain embodiments, such tablets are suitable for once daily dosing.

HIV Combination Therapy

In the above embodiments, the additional therapeutic agent may be an anti-HIV agent selected from the group consisting of combination drugs for treating HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; cabotegravir and rilpivirine; cabotegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride; lopinavir, ritonavir, zidovudine and lamivudine; Vacc-4× and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, 2G12, C4E10, C2F5+C2G12+C4E10, 3-BNC-117, ANC195, 3BNC117, 3BNC60, 10-1074, PGT145, PGT121, PGT-151, PGT-133, MDX010 (ipilimumab), DH511, N6, VRC01, PGDM1400, A32, 7B2, 10E8, 10E8v4, CAP256-VRC26.25, DRVIA7, VRC-07-523, VRC-HIVMAB080-00-AB, VRC-HIVMAB060-00-AB, VRC-HIVMAB060-00-AB, MGD-014 and VRC07. An example of HIV bispecific antibodies include MGD014.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHlVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4×+romidepsin, variant gp120 polypeptide vaccine, rAd5 gag-pol env A/B/C vaccine, DNA.HTI and MVA.HTI.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with one or two HIV nucleoside or nucleotide inhibitors of reverse transcriptase. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase. In another embodiment, a compound disclosed herein, or a pharmaceutically acceptable salt thereof, is combined with a non-nucleoside inhibitor of reverse transcriptase. In another embodiment, a compound disclosed herein, or a pharmaceutically acceptable salt thereof, is combined with a non-nucleoside inhibitor of reverse transcriptase and an integrase inhibitor.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide fumarate or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide fumarate or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a compound disclosed herein, or a pharmaceutically acceptable salt thereof, is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a compound disclosed herein, or a pharmaceutically acceptable salt thereof, is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, the compound disclosed herein, or a pharmaceutically acceptable salt thereof, and the first and second additional therapeutic agents as disclosed above are administered simultaneously. Optionally, the compound disclosed herein, or a pharmaceutically acceptable salt thereof, and the first and second additional therapeutic agents as disclosed above are combined in a unitary dosage form for simultaneous administration to a subject. In other embodiments, the compound disclosed herein, or a pharmaceutically acceptable salt thereof, and the first and second additional therapeutic agents as disclosed above are administered sequentially.

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In some embodiments, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents, in any dosage amount of the compound (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 1 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Birth Control (Contraceptive) Combination Therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segesterone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of dendritic cell therapy include AGS-004.

Gene Editors

The genome editing system is selected from the group consisting of: a CRISPR/Cas9 system, a zinc finger nuclease system, a TALEN system, a homing endonucleases system, and a meganuclease system. Examples of HIV targeting CRISPR/Cas9 systems include EBT101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+T cell, a CD8+T cell, or a combination thereof. Examples of HIV CAR-T include VC-CAR-T.

TCR-T Cell Therapy

TCR-T cells are engineered to target HIV derived peptides present on the surface of virus-infected cells.

XRPD Data

In certain embodiments, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The characteristic peaks of a given XRPD can be selected according to the peak locations and their relative intensity to conveniently distinguish this crystalline structure from others.

XRPD patterns were collected on a PANanalytical XPERT-PRO diffractometer at ambient conditions under the following experimental settings: 45 KV, 40 mA, Kα1=1.5406 Å, scan range 2° to 40°, step size 0.0084° or 0.0167°, measurement time: 5 min.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7−0.3, i.e., about 8.4. Depending on the sample preparation techniques, the calibration techniques applied to the instruments, human operational variation, and etc., those skilled in the art recognize that the appropriate error of margins for a XRPD can be ±0.5; ±0.4; ±0.3; ±0.2; ±0.1; ±0.05; or less. In certain embodiments of the invention, the XRPD margin of error is±0.2. In certain embodiments of the invention, the XRPD margin of error is±0.5.

Additional details of the methods and equipment used for the XRPD analysis are described in the Examples section.

The XRPD peaks for crystalline Form I are below in Table 1A.

TABLE 1A

XRPD peaks for crystalline Form I
Formula I
Form 1

| Peak Position [°2θ] | Relative Intensity [%] |
| --- | --- |
| 7.2 | 29 |
| 9.9 | 7 |
| 10.8 | 10 |
| 11.7 | 18 |
| 14.3 | 15 |
| 16.9 | 45 |
| 17.8 | 66 |
| 18.3 | 49 |
| 18.8 | 10 |
| 19.3 | 22 |
| 20.7 | 15 |
| 21.4 | 20 |
| 23.4 | 26 |
| 25.1 | 100 |
| 25.8 | 25 |
| 26.3 | 16 |
| 26.8 | 31 |
| 27.5 | 7 |
| 28.7 | 17 |
| 29.7 | 4 |
| 31.3 | 5 |
| 32.0 | 12 |
| 32.5 | 15 |
| 33.8 | 12 |
| 35.3 | 6 |
| 36.5 | 9 |
| 37.4 | 4 |

The XRPD peaks for Formula I Hydrate I are below in Table 1B.

TABLE 1B

XRPD peaks for crystalline Formula I Hydrate I
Formula I
Hydrate I

| Peak Position [°2θ] | Relative Intensity [%] |
| --- | --- |
| 5.3 | 15 |
| 7.4 | 45 |
| 7.6 | 100 |
| 8.3 | 42 |
| 10.6 | 78 |
| 11.7 | 25 |
| 13.6 | 36 |
| 15.9 | 75 |
| 17.6 | 40 |
| 18.0 | 60 |

TABLE 1B-continued

XRPD peaks for crystalline Formula I Hydrate I
Formula I
Hydrate I

| Peak Position [°2θ] | Relative Intensity [%] |
|---|---|
| 18.8 | 57 |
| 19.2 | 15 |
| 19.4 | 21 |
| 19.9 | 25 |
| 20.2 | 38 |
| 20.5 | 43 |
| 20.7 | 21 |
| 21.0 | 16 |
| 21.9 | 61 |
| 22.4 | 29 |
| 22.7 | 17 |
| 23.5 | 26 |
| 24.1 | 43 |
| 25.6 | 23 |
| 26.0 | 21 |
| 26.6 | 24 |
| 27.4 | 23 |
| 28.8 | 13 |
| 34.9 | 8 |
| 35.4 | 7 |

The XRPD peaks for Formula I Acetic Acid Solvate are below in Table 1C.

TABLE 1C

XRPD peaks for Formula I Acetic Acid Solvate
Formula I
Acetic Acid Solvate

| Peak Position [°2θ] | Relative Intensity [%] |
|---|---|
| 7.2 | 51 |
| 9.3 | 22 |
| 10.0 | 6 |
| 10.7 | 15 |
| 11.4 | 28 |
| 12.8 | 9 |
| 14.0 | 39 |
| 14.7 | 10 |
| 16.8 | 97 |
| 17.3 | 51 |
| 18.4 | 48 |
| 19.1 | 42 |
| 20.0 | 22 |
| 20.5 | 89 |
| 21.3 | 100 |
| 22.1 | 16 |
| 22.8 | 64 |
| 23.1 | 74 |
| 23.8 | 33 |
| 24.5 | 9 |
| 25.0 | 10 |
| 25.8 | 9 |
| 26.2 | 18 |
| 27.0 | 20 |
| 28.4 | 42 |
| 29.2 | 6 |
| 30.5 | 19 |
| 31.3 | 8 |
| 32.7 | 7 |
| 33.6 | 10 |
| 38.8 | 6 |
| 39.5 | 7 |

The XRPD peaks for Formula I Esylate I are below in Table 1D.

TABLE 1D

XRPD peaks for crystalline Formula I Esylate I
Formula I
Esylate

| Peak Position [°2θ] | Relative Intensity [%] |
|---|---|
| 9.9 | 10 |
| 10.2 | 7 |
| 11.1 | 22 |
| 11.3 | 5 |
| 13.4 | 6 |
| 14.1 | 26 |
| 15.6 | 26 |
| 16.6 | 34 |
| 17.9 | 44 |
| 19.0 | 6 |
| 19.6 | 9 |
| 19.9 | 25 |
| 20.3 | 17 |
| 20.9 | 17 |
| 21.5 | 100 |
| 22.1 | 49 |
| 22.6 | 26 |
| 22.9 | 26 |
| 23.8 | 52 |
| 24.8 | 14 |
| 25.0 | 9 |
| 26.6 | 30 |
| 27.3 | 6 |
| 28.0 | 27 |
| 28.6 | 8 |
| 29.6 | 7 |
| 32.5 | 5 |
| 34.9 | 12 |
| 35.7 | 11 |
| 36.0 | 10 |
| 36.6 | 5 |
| 37.1 | 6 |
| 38.9 | 6 |

The XRPD peaks for crystalline Formula I Besylate I are below in Table 1E.

TABLE 1E

XRPD peaks for crystalline Formula I Besylate I
Formula I
Besylate

| Peak Position [°2θ] | Relative Intensity [%] |
|---|---|
| 8.4 | 53 |
| 12.3 | 5 |
| 13.9 | 15 |
| 16.6 | 15 |
| 17.5 | 9 |
| 18.8 | 6 |
| 19.4 | 35 |
| 21.4 | 10 |
| 22.2 | 8 |
| 24.0 | 10 |
| 25.0 | 100 |
| 26.5 | 14 |
| 30.6 | 16 |
| 33.5 | 11 |
| 36.7 | 5 |

The XRPD peaks for crystalline Formula I Hemisulfate I are below in Table 1F.

TABLE 1F

XRPD peaks for crystalline Formula I Hemisulfate I
Formula I
Hemisulfate

| Peak Position [°2θ] | Relative Intensity [%] |
| --- | --- |
| 3.4 | 100 |
| 4.8 | 26 |
| 7.6 | 73 |
| 8.7 | 9 |
| 9.7 | 15 |
| 10.2 | 14 |
| 12.1 | 27 |
| 13.0 | 11 |
| 14.1 | 8 |
| 15.5 | 23 |
| 17.0 | 11 |
| 17.5 | 7 |
| 18.9 | 10 |
| 19.5 | 64 |
| 20.8 | 10 |
| 21.7 | 40 |
| 22.3 | 43 |
| 22.9 | 33 |
| 23.9 | 7 |
| 25.0 | 7 |
| 25.8 | 30 |
| 26.3 | 34 |
| 28.4 | 8 |
| 29.3 | 5 |
| 31.1 | 6 |
| 31.7 | 5 |
| 33.2 | 5 |

The XRPD peaks for crystalline Formula I Napsylate I are below in Table 1G.

TABLE 1G

XRPD peaks for crystalline Formula I Napsylate I
Formula I
Napsylate

| Peak Position [°2θ] | Relative Intensity [%] |
| --- | --- |
| 3.4 | 37 |
| 6.7 | 3 |
| 8.0 | 3 |
| 10.0 | 64 |
| 11.8 | 33 |
| 13.3 | 33 |
| 16.3 | 14 |
| 16.7 | 11 |
| 17.9 | 28 |
| 20.0 | 100 |
| 21.1 | 7 |
| 23.4 | 34 |
| 25.6 | 3 |
| 26.8 | 25 |
| 28.1 | 4 |
| 33.1 | 4 |

The XRPD peaks for crystalline Formula I Hemiedisylate I are below in Table 1H.

TABLE 1H

XRPD peaks for crystalline Formula I Hemiedisylate I
Formula I
Hemiedisylate

| Peak Position [°2θ] | Relative Intensity [%] |
| --- | --- |
| 5.4 | 1 |
| 8.0 | 100 |
| 9.1 | 3 |
| 10.7 | 4 |
| 13.5 | 27 |
| 14.9 | 4 |
| 16.1 | 10 |
| 18.8 | 14 |
| 21.5 | 4 |
| 24.2 | 28 |
| 27.0 | 3 |
| 32.6 | 5 |

The XRPD peaks for crystalline Formula I Tosylate I are below in Table 1I.

TABLE 1I

XRPD peaks for crystalline Formula I Tosylate I
Formula I
Tosylate

| Peak Position [°2θ] | Relative Intensity [%] |
| --- | --- |
| 5.3 | 100 |
| 6.7 | 14 |
| 9.4 | 18 |
| 10.5 | 10 |
| 11.7 | 8 |
| 12.5 | 7 |
| 13.8 | 40 |
| 14.3 | 32 |
| 14.6 | 45 |
| 15.0 | 31 |
| 16.8 | 9 |
| 17.3 | 12 |
| 18.9 | 43 |
| 19.7 | 9 |
| 20.7 | 25 |
| 21.3 | 29 |
| 22.1 | 8 |
| 23.3 | 22 |
| 23.6 | 52 |
| 24.5 | 14 |
| 25.2 | 5 |
| 26.8 | 6 |
| 29.1 | 7 |

The XRPD peaks for Formula I, Material A are below in Table 1J.

TABLE 1J

XRPD peaks for Formula I, Material A
Formula I, Material A

| Pos. [°2Th.] | Rel. Int. [%] |
| --- | --- |
| 5.2 | 2 |
| 7.1 | 19 |
| 7.6 | 14 |
| 8.3 | 5 |
| 9.9 | 17 |
| 10.6 | 13 |
| 11.7 | 33 |

TABLE 1J-continued

XRPD peaks for Formula I, Material A
Formula I, Material A

| Pos. [°2Th.] | Rel. Int. [%] |
|---|---|
| 13.5 | 4 |
| 14.1 | 9 |
| 15.9 | 11 |
| 16.8 | 53 |
| 17.6 | 34 |
| 18.2 | 100 |
| 18.4 | 47 |
| 18.8 | 33 |
| 19.2 | 48 |
| 19.8 | 6 |
| 20.6 | 19 |
| 21.3 | 20 |
| 21.6 | 19 |
| 22.6 | 4 |
| 23.1 | 9 |
| 23.4 | 13 |
| 24.7 | 14 |
| 25.1 | 21 |
| 25.7 | 19 |
| 26.2 | 11 |
| 26.8 | 9 |
| 27.4 | 5 |
| 28.7 | 21 |
| 29.7 | 5 |
| 31.3 | 3 |
| 32.0 | 8 |
| 35.3 | 4 |
| 36.5 | 4 |
| 37.4 | 3 |

The XRPD peaks for the MEK solvate of Formula I are below in Table 1K.

TABLE 1K

XRPD peaks for Formula I, MEK solvate
Formula I, MEK solvate

| Pos. [°2Th.] | Rel. Int. [%] |
|---|---|
| 7.0 | 16 |
| 9.4 | 10 |
| 10.5 | 9 |
| 10.8 | 7 |
| 11.4 | 10 |
| 13.0 | 5 |
| 13.7 | 26 |
| 14.1 | 14 |
| 14.5 | 6 |
| 15.0 | 6 |
| 16.6 | 61 |
| 17.5 | 37 |
| 18.8 | 20 |
| 19.1 | 11 |
| 19.6 | 8 |
| 20.1 | 23 |
| 20.8 | 100 |
| 21.1 | 52 |
| 21.5 | 31 |
| 22.6 | 73 |
| 22.9 | 55 |
| 23.3 | 62 |
| 25.0 | 3 |
| 25.5 | 13 |
| 26.1 | 9 |
| 27.2 | 22 |
| 27.9 | 20 |
| 28.2 | 12 |
| 28.7 | 5 |
| 29.1 | 9 |
| 29.8 | 10 |

TABLE 1K-continued

XRPD peaks for Formula I, MEK solvate
Formula I, MEK solvate

| Pos. [°2Th.] | Rel. Int. [%] |
|---|---|
| 31.4 | 9 |
| 33.6 | 3 |
| 36.4 | 3 |
| 37.7 | 8 |
| 39.1 | 6 |

The XRPD peaks for the MeTHF solvate of Formula I are below in Table 1L.

TABLE 1L

XRPD peaks for MeTHF solvate of Formula I
Formula I, MeTHF solvate

| Pos. [°2Th.] | Rel. Int. [%] |
|---|---|
| 7.1 | 21 |
| 9.2 | 7 |
| 10.5 | 27 |
| 11.3 | 10 |
| 13.7 | 41 |
| 14.0 | 29 |
| 14.5 | 13 |
| 14.8 | 9 |
| 16.5 | 50 |
| 17.2 | 26 |
| 18.6 | 21 |
| 19.0 | 6 |
| 19.5 | 13 |
| 20.4 | 68 |
| 21.1 | 55 |
| 21.4 | 14 |
| 22.7 | 100 |
| 23.3 | 24 |
| 25.4 | 13 |
| 26.9 | 18 |
| 27.5 | 11 |
| 27.9 | 18 |
| 29.0 | 8 |
| 29.7 | 15 |
| 33.2 | 11 |

The XRPD peaks for the MeOAc solvate of Formula I are below in Table 1M.

TABLE 1M

XRPD peaks for MeOAc solvate of Formula I
Formula I, MeOAc solvate

| Pos. [°2Th.] | Rel. Int. [%] |
|---|---|
| 7.2 | 44 |
| 9.5 | 14 |
| 10.2 | 8 |
| 10.5 | 9 |
| 11.4 | 12 |
| 13.0 | 6 |
| 13.8 | 36 |
| 14.2 | 19 |
| 15.1 | 8 |
| 16.7 | 81 |
| 17.6 | 52 |
| 18.9 | 25 |
| 19.2 | 13 |
| 19.7 | 5 |
| 20.3 | 38 |
| 20.7 | 85 |

TABLE 1M-continued

XRPD peaks for MeOAc solvate of Formula I
Formula I, MeOAc solvate

| Pos. [°2Th.] | Rel. Int. [%] |
|---|---|
| 20.9 | 100 |
| 21.3 | 81 |
| 21.5 | 48 |
| 22.9 | 73 |
| 23.4 | 72 |
| 25.6 | 9 |
| 27.4 | 17 |
| 28.0 | 19 |
| 28.5 | 13 |
| 29.3 | 31 |
| 29.9 | 9 |
| 30.4 | 7 |
| 31.6 | 9 |
| 35.6 | 6 |
| 36.5 | 10 |

The XRPD peaks for ethyl formate solvate of Formula I are below in Table 1N.

TABLE 1N

XRPD peaks for ethyl formate solvate of Formula I
Formula I, ethyl formate solvate

| Pos. [°2Th.] | Rel. Int. [%] |
|---|---|
| 7.2 | 26 |
| 9.5 | 17 |
| 10.2 | 7 |
| 10.8 | 7 |
| 11.5 | 22 |
| 13.1 | 11 |
| 14.0 | 18 |
| 16.6 | 50 |
| 17.6 | 74 |
| 18.9 | 20 |
| 19.4 | 50 |
| 20.3 | 27 |
| 20.9 | 100 |
| 21.4 | 71 |
| 22.9 | 90 |
| 23.4 | 42 |
| 24.5 | 5 |
| 26.1 | 11 |
| 26.6 | 6 |
| 27.4 | 16 |
| 28.0 | 14 |
| 28.5 | 15 |
| 29.5 | 12 |
| 30.6 | 8 |
| 31.7 | 6 |
| 32.8 | 7 |
| 34.9 | 9 |

Preparation of Crystalline Forms

One method of synthesizing darunavir (e.g. Formula I) has been previously described in PCT Publication No.WO1995/006030, filed Aug. 23, 1994. This reference is hereby incorporated herein by reference in its entirety, and specifically with respect to the synthesis of darunavir.

For example, in one aspect, provided is a method of producing a composition comprising one or more crystalline forms of Formula I, wherein the method comprises combining a compound of Formula I with a suitable solvent or a mixture of suitable solvents to produce a composition comprising one or more crystalline forms of the compound of Formula I. In another aspect, provided is another method of producing a composition comprising one or more crystalline forms of Formula I, wherein the method comprises combining Formula I with a suitable solvent or a mixture of suitable solvents.

The choice of a particular solvent or combination of solvents or method of combining solvents affects the formation favoring one crystalline form of Formula I over another. Solvents suitable for crystal formation may include, for example: isopropyl acetate, methyl tert-butyl ether, n-heptane, butyl acetate, ethyl acetate, methyl isobutyl ketone, acetic acid, water, acetonitrile, and any mixtures thereof.

The presence of impurities may affect the formation favoring one crystalline form of Formula I over another. In some embodiments, the form is prepared by a process comprising Formula I having impurities. In another embodiment, the form is prepared by a process comprising substantially pure Formula I.

In another aspect, provided is also one or more crystalline forms of Formula I produced according to any of the methods described herein.

It should be understood that the methods for preparing the crystalline forms described herein may yield quantity and quality differences compared to the methods for preparing a compound of Formula I produced on laboratory scale.

Formula I Form I

In some embodiments, provided is a method of producing a composition comprising crystalline Form I, wherein the method comprises combining Formula I with a solvent to produce a composition comprising crystalline Form I, wherein the solvent is isopropyl acetate.

Provided is crystalline Form I produced by combining Formula I with a solvent, wherein the solvent is isopropyl acetate.

In some embodiments, provided is a method of producing a composition comprising crystalline Form I, wherein the method comprises combining Formula I with a solvent to produce a composition comprising crystalline Form I, wherein the solvent is methyl tert-butyl ether.

Provided is crystalline Form I produced by combining Formula I with a solvent, wherein the solvent is methyl tert-butyl ether.

In some embodiments, provided is a method of producing a composition comprising crystalline Form I, wherein the method comprises combining Formula I with a solvent and an antisolvent to produce a composition comprising crystalline Form I, wherein the solvent is ethyl acetate and the antisolvent is hexane or n-heptane.

Provided is crystalline Formula I Form I produced by combining Formula I with a solvent and an antisolvent, wherein the solvent is ethyl acetate and the antisolvent is hexane or n-heptane.

In some embodiments, provided is a method of producing a composition comprising crystalline Form I, wherein the method comprises combining Formula I with a solvent to produce a composition comprising crystalline Form I, wherein the solvent is methyl isobutyl ketone.

Provided is crystalline Form I produced by combining Formula I with a solvent, wherein the solvent is methyl isobutyl ketone.

In some embodiments, provided is a method of producing a composition comprising crystalline Form I, wherein the method comprises combining Formula I with a solvent to produce a composition comprising crystalline Form I, wherein the solvent is isopropyl acetate and n-heptane.

Provided is crystalline Form I produced by combining Formula I with a solvent, wherein the solvent is isopropyl acetate and n-heptane.

In some embodiments, provided is a method of producing a composition comprising crystalline Form I, wherein the method comprises combining Formula I with a solvent to produce a composition comprising crystalline Form I, wherein the solvent is isopropyl acetate and methyl tert-butyl ether.

Provided is crystalline Form I produced by combining Formula I with a solvent, wherein the solvent is isopropyl acetate and methyl tert-butyl ether.

In some embodiments, provided is a method of producing a composition comprising crystalline Form I, wherein the method comprises combining Formula I with a solvent to produce a composition comprising crystalline Form I, wherein the solvent is butyl acetate. Provided is crystalline Form I produced by combining Formula I with a solvent, wherein the solvent is butyl acetate.

In some embodiments, provided is a method of producing a composition comprising crystalline Form I, wherein the method comprises combining Formula I with a solvent to produce a composition comprising crystalline Form I, wherein the solvent is butyl acetate and methyl tert-butyl ether.

Provided is crystalline Form I produced by combining Formula I with a solvent, wherein the solvent is butyl acetate and methyl tert-butyl ether.

In some embodiments, provided is a method of producing a composition comprising crystalline Form I, wherein the method comprises combining Formula I with a solvent to produce a composition comprising crystalline Form I, wherein the solvent is butyl acetate and n-heptane.

Provided is crystalline Form I produced by combining Formula I with a solvent, wherein the solvent is butyl acetate and n-heptane.

Formula I Hydrate I

In some embodiments, provided is a method of producing a composition comprising crystalline Formula I Hydrate I, wherein the method comprises combining Formula I with a stoichiometric or non-stoichiometric amount of solvent to produce a composition comprising crystalline Formula I Solvate, wherein the solvent is water. Formula I, Hydrate I can have a range of water content depending on drying or hydrating conditions. In some embodiments, Formula I, Hydrate I has about 6 equiv. of water. In some embodiments, Formula I, Hydrate I has more than about 6 equiv. of water.

Provided is crystalline Formula I Hydrate I produced by combining Formula I with a solvent, wherein the solvent is water.

Formula I Acetic Acid Solvate

In some embodiments, provided is a method of producing a composition comprising crystalline Formula I Acetic Acid Solvate, wherein the method comprises combining Formula I with a solvent to produce a composition comprising crystalline Formula I Acetic Acid Solvate, wherein the solvent is acetic acid and n-heptane.

Provided is crystalline Formula I Acetic Acid Solvate produced by combining Formula I with a solvent, wherein the solvent is acetic acid and n-heptane.

Formula I Esylate I

In some embodiments, provided is a method of producing a composition comprising crystalline Formula I Esylate I, wherein the method comprises combining Formula I with ethanesulfonic acid and a solvent to produce a composition comprising crystalline Formula I Esylate I, wherein the solvent is acetonitrile.

Provided is crystalline Formula I Esylate I produced by combining Formula I with ethanesulfonic acid and a solvent, wherein the solvent is acetonitrile.

Formula I Besylate I

In some embodiments, provided is a method of producing a composition comprising crystalline Formula I Besylate I, wherein the method comprises combining Formula I with benzenesulfonic acid and a solvent to produce a composition comprising crystalline Formula I Besylate I, wherein the solvent is acetonitrile.

Provided is crystalline Formula I Besylate I produced by combining Formula I with benzenesulfonic acid and a solvent, wherein the solvent is acetonitrile.

Formula I Hemisulfate I

In some embodiments, provided is a method of producing a composition comprising crystalline Formula I Hemisulfate I, wherein the method comprises combining Formula I with sulfuric acid and a solvent to produce a composition comprising crystalline Formula I Hemisulfate I, wherein the solvent is acetonitrile.

Provided is crystalline Formula I Hemisulfate I produced by combining Formula I with sulfuric acid and a solvent, wherein the solvent is acetonitrile.

Formula I Napsylate I

In some embodiments, provided is a method of producing a composition comprising crystalline Formula I Napsylate I, wherein the method comprises combining Formula I with 2-naphthalenesulfonic acid and a solvent to produce a composition comprising crystalline Formula I Napsylate I, wherein the solvent is acetonitrile. Provided is crystalline Formula I Napsylate I produced by combining Formula I with 2-naphthalenesulfonic acid and a solvent, wherein the solvent is acetonitrile.

Formula I Hemiedisylate I

In some embodiments, provided is a method of producing a composition comprising crystalline Formula I Hemiedisylate I, wherein the method comprises combining Formula I with ethane-1,2-disulfonic acid and a solvent to produce a composition comprising crystalline Formula I Hemiedisylate I, wherein the solvent is acetonitrile. Provided is crystalline Formula I Hemiedisylate I produced by combining Formula I with ethane-1,2-disulfonic acid and a solvent, wherein the solvent is acetonitrile.

Formula I Tosylate I

In some embodiments, provided is a method of producing a composition comprising crystalline Formula I Tosylate I, wherein the method comprises combining Formula I with p-toluenesulfonic acid monohydrate and a solvent to produce a composition comprising crystalline Formula I Tosylate I, wherein the solvent is acetonitrile.

Provided is crystalline Formula I Tosylate I produced by combining Formula I with p-toluenesulfonic acid monohydrate and a solvent, wherein the solvent is acetonitrile.

Formula I, Material A

In some embodiments, provided is a method of producing a composition comprising free base Formula I, Material A, wherein the method comprises dehydrating Formula I, Hydrate I. Provided herein is crystalline free base, Material A form of Formula I produced by dehydrating a free base hydrate I form of Formula I.

Formula I, MEK Solvate

In some embodiments, provided is a method of producing a composition comprising Formula I, MEK solvate, wherein the method comprises combining free base Formula I with a solvent to produce a composition comprising Formula I, MEK solvate, wherein the solvent is methyl ethyl ketone and n-heptane.

Provided herein is Formula I, MEK solvate produced by combining free base Formula I with a solvent or a combination of solvents. In certain embodiments, the solvent is methyl ethyl ketone. In certain embodiments, the solvent is methyl ethyl ketone and n-heptane.

Formula I, MeTHF Solvate

In some embodiments, provided is a method of producing a composition comprising Formula I, MeTHF solvate, wherein the method comprises combining free base Formula I with a solvent to produce a composition comprising Formula I, MEK solvate, wherein the solvent is MeTHF and n-heptane.

Provided herein is Formula I, MeTHF solvate produced by combining free base Formula I with a solvent or a combination of solvents. In certain embodiments, the solvent is MeTHF. In certain embodiments, the solvent is MeTHF and n-heptane.

Formula I, MeOAc Solvate

In some embodiments, provided is a method of producing a composition comprising Formula I, MeOAc solvate, wherein the method comprises combining free base Formula I with a solvent to produce a composition comprising Formula I, MeOAc solvate, wherein the solvent is MeTHF and n-heptane.

Provided herein is Formula I, MeOAc solvate produced by combining free base Formula I with a solvent or a combination of solvents. In certain embodiments, the solvent is MeOAc. In certain embodiments, the solvent is MeOAc and n-heptane.

Formula I, Ethyl Formate Solvate

In some embodiments, provided is a method of producing a composition comprising Formula I, ethyl formate solvate form, wherein the method comprises combining free base Formula I with a solvent to produce a composition comprising Formula I, ethyl formate solvate, wherein the solvent is ethyl formate and n-heptane.

Provided herein is Formula I, ethyl formate solvate produced by combining free base Formula I with a solvent or a combination of solvents. In certain embodiments, the solvent is ethyl formate. In certain embodiments, the solvent is ethyl formate and n-heptane.

Uses in Manufacturing of Drug Product

Provided is also a use of the crystalline forms described herein in the manufacture of a drug product. The one or more of the crystalline forms described herein (e.g., the compounds of Formula I described herein) may be used in the manufacturing process to produce the drug product. The one or more of the crystalline forms described herein (e.g., the compounds of Formula I described herein) may be used as an intermediate in the manufacturing process to produce the drug product.

In certain embodiments, crystalline compounds of Formula I are used in the manufacture of an active pharmaceutical ingredient. In certain embodiments, Formula I Form I is used in the manufacture of an active pharmaceutical ingredient. In certain embodiments, Formula I Acetic Acid Solvate is used in the manufacture of an active pharmaceutical ingredient. In certain embodiments, Formula I Hydrate I is used in the manufacture of an active pharmaceutical ingredient. In certain embodiments, Formula I, Hydrate I having approximately 6 equiv of water is used in the manufacture of an active pharmaceutical ingredient. In certain embodiments, Formula I Esylate I is used in the manufacture of an active pharmaceutical ingredient. In certain embodiments, Formula I Besylate I is used in the manufacture of an active pharmaceutical ingredient. In certain embodiments, Formula I Hemisulfate I is used in the manufacture of an active pharmaceutical ingredient. In certain embodiments, Formula I Napsylate I is used in the manufacture of an active pharmaceutical ingredient. In certain embodiments, Formula I Hemiedisylate I is used in the manufacture of an active pharmaceutical ingredient. In certain embodiments, Formula I Tosylate I is used in the manufacture of an active pharmaceutical ingredient. In certain embodiments, Formula I, Material A is used in the manufacture of an active pharmaceutical ingredient. In certain embodiments, Formula I, MEK (methyl ethyl ketone) solvate is used in the manufacture of an active pharmaceutical ingredient. In certain embodiments, Formula I, MeTHF (methyl tetrahydrofuran) solvate is used in the manufacture of an active pharmaceutical ingredient. In certain embodiments, Formula I, MeOAc (methyl acetate) solvate is used in the manufacture of an active pharmaceutical ingredient. In certain embodiments, Formula I, ethyl formate solvate is used in the manufacture of an active pharmaceutical ingredient.

Articles of Manufacture and Kits

Compositions comprising one or more of the crystalline forms described herein (e.g., a compound of Formula I described herein) and formulated in one or more pharmaceutically acceptable excipients or other ingredients can be prepared, placed in an appropriate container, and labeled for treatment of an indicated condition. Accordingly, there also is contemplated an article of manufacture, such as a container comprising a dosage form of one or more of the crystalline forms described herein and a label containing instructions for use of the compound(s). In some embodiments, the article of manufacture is a container comprising a dosage form of one or more of the crystalline forms described herein, and one or more pharmaceutically acceptable excipients or other ingredients. In some embodiments of the articles of manufacture described herein, the dosage form is a solution.

Kits also are contemplated. For example, a kit can comprise a dosage form of a pharmaceutical composition and a package insert containing instructions for use of the composition in treatment of a medical condition. In another embodiment a kit may comprise multiple individual dosage forms, each comprising a therapeutically effective amount of a compound as described herein, and instructions for their administration to a human in need thereof. Each of the individual dosage forms may comprise a therapeutically effective amount of a compound as described herein in combination with at least one pharmaceutically effective excipient. The individual dosage forms may be in the form of, as examples, a solution, a tablet, a pill, a capsule, a sachet, a sublingual medicament, a lyophilized powder, a spray-dried powder, or a liquid composition for oral, parenteral, or topical administration. The instructions for use in the kit may be for treating an HIV virus infection. The instructions may be directed to any of the viral infections and methods described herein. The instructions may be for prophylaxis or the treatment of an existing viral infection.

In certain embodiments, the crystalline or salt forms described herein may potentially exhibit improved properties. For example, in certain embodiments, the crystalline or salt forms described herein may potentially exhibit improved stability. Such improved stability could have a potentially beneficial impact on the manufacture of the compound of Formula I, such as for example offering the ability to store process intermediate for extended periods of time. Improved stability could also potentially benefit a composition or pharmaceutical composition of the compound of Formula I. In certain embodiments, the crystalline or salt described herein may also potentially result in improved yield of the compound of Formula I, or potentially result in an improvement of the quality of the compound of Formula I. In certain embodiments, the crystalline, salt and solvate forms described herein may also exhibit improved pharmacokinetic properties and/or potentially improved bioavailability.

Methods

Formula I Form I

Formula I (about 300 mg) was added to a glass vial. Isopropyl acetate (about 1 mL) was added, the vial was capped, and the suspension was heated to about 70° C. for about 16 hours. Isopropyl acetate (about 0.5 mL) was added, the suspension was cooled to about room temperature and stirred for about 24 hours. Formula I Form I was isolated as a solid from the suspension by filtration and characterized as discussed below.

In an alternative method, Formula I (about 300 mg) was added to a glass vial. Methyl tert-butyl ether (about 1 mL) was added, the vial was capped, and the suspension was heated to about 70° C. for about 20 hours, and cooled to about room temperature and stirred for about 24 hours. Formula I Form I was isolated as a solid from the suspension by filtration and characterized as discussed below.

In an alternative method, Formula I (about 1 gram) was slurried in about 5 mL of toluene in a vial for about 4 days at about 22° C. The resulting suspension was isolated as a solid by filtration and characterized as discussed below.

In an alternative method, Formula I (about 1 gram) was slurried in about 5 mL of butyl acetate/ n-heptane 1/1 (v/v) solution in a vial for about 5 days at about 22° C. The resulting suspension was isolated as a solid by filtration and characterized as discussed below.

Formula I Hydrate I

Formula I (about 500 mg) was added to a glass vial. Water (about 5 mL) was added and the vial was capped at about room temperature. The mixture was stirred for about nine days. Formula I Hydrate I was isolated as a solid from the suspension by filtration and characterized as discussed below.

Formula I, Hydrate I having more water content is shown in FIG. 7b to have a weight loss of 16.3% at 150° C. that can be attributed to loss of water. Based on the molecular weight of free base Formula I, this weight loss corresponds to approximately 6 equivalents of water. DSC analysis of the same material hydrate I (FIG. 6b) shows a broad endotherm that spans from ambient temperature to 75° C., followed by another broad endotherm that starts at 100° C.

Formula I Acetic Acid Solvate

Formula I (about 1000 mg) was added to a glass vial. Acetic acid (about 1 mL) and n-heptane (about 0.25 mL) were added and the vial was stirred at about room temperature for about 16 hours. Formula I Acetic Acid Solvate was isolated as a solid from the suspension by filtration and characterized as discussed below.

Formula I Esylate I

Formula I (about 1 g) was added to a glass vial. Acetonitrile (about 5 mL) and ethanesulfonic acid (about 0.20 g) were added and the vial was capped. The solution was sonicated and stirred for about 12 hours. Formula I Esylate I was isolated as a solid from the suspension by filtration and characterized as discussed below.

Formula I Besylate I

Formula I (about 1 g) was added to a glass vial. Acetonitrile (about 5 mL) and benzensulfonic acid (about 0.29 g) were added and the vial was capped. The solution was sonicated, diluted with acetonitrile (about 10 mL) and stirred for about 12 hours. Formula I Besylate I was isolated as a solid from the suspension by filtration and characterized as discussed below.

Formula I Hemisulfate I

Formula I (about 1 g) was added to a glass vial. Acetonitrile (about 5 mL) and sulfuric acid (about 0.05 g) were added and the vial was capped. The solution was sonicated, diluted with acetonitrile (about 10 mL) and stirred for about 12 hours. Formula I Hemisulfate I was isolated as a solid from the suspension by filtration and characterized as discussed below.

Formula I Napsylate I

Formula I (about 1 g) was added to a glass vial. Acetonitrile (about 5 mL) and 2-naphthalenesulfonic acid (about 0.38 g) were added and the vial was capped. The solution was sonicated, diluted with acetonitrile (about 10 mL) and stirred for about 12 hours. Formula I Napsylate I was isolated as a solid from the suspension by filtration and characterized as discussed below.

Formula I Hemiedisylate I

Formula I (about 1 g) was added to a glass vial. Acetonitrile (about 5 mL) and ethane-1,2-disulfonic acid (about 0.10 g) were added and the vial was capped. The solution was sonicated, diluted with acetonitrile (about 10 mL) and stirred for about 12 hours. Formula I Hemiedisylate I was isolated as a solid from the suspension by filtration and characterized as discussed below.

Formula I Tosylate I

Formula I (about 1 g) was added to a glass vial. Acetonitrile (about 5 mL) and p-toluenesulfonic acid monohydrate (about 0.35 g) were added and the vial was capped. The solution was sonicated, diluted with acetonitrile (about 10 mL), partially capped and stirred for about 12 hours. Formula I Tosylate I was isolated as a solid from the suspension by filtration and characterized as discussed below.

Formula I, Material A

Formula I, Material A (free base) is obtained from Formula I, Hydrate I via dehydration by vacuum or at elevated temperatures or a combination of both. FIG. 26 shows the XRPD pattern of Formula I, Material A, produced by drying Formula I, Hydrate I under vacuum at 50° C. The TGA analysis of Formula I, Material A is shown in FIG. 28. The solids lost about 0.64% weight at150° C. Based on the molecular weight of free base Formula I, this corresponds to about 0.2 eq. of water. The DSC thermogram of Formula I, Material A that has been dried at 50° C. under vacuum, is shown in FIG. 27.

Formula I, MEK Solvate

A solution containing about 300 mg of free base Formula I in 1 mL MEK was stirred at about 22° C. overnight, then about 70° C. for 1 day, and at about 22° C. for another day. It remained as a solution. A small amount of seeds of Formula I, Form I was added and the sample became a thick slurry after 1 day. The sample was filtered, dried in the vacuum oven at 50° C. to become partially de-solvated.

An alternative method of obtaining free base Formula I, MEK solvate is: 20 g of amorphous Formula I was dissolved in 40 mL MEK at 20° C. Seeds of MEK solvate from experiment above were then added to the solution. After stirring for 30 min, 40 mL methyl tert-butyl ether (MTBE) was added over 2 h and held overnight. An additional 40 mL n-hetpane was added over 1 h. The slurry was filtered, washed with 20 mL heptane, and dried at 50° C. in the vacuum oven for 2 days. The XRPD pattern of free base Formula I, MEK solvate, as a wet cake, is shown in FIG. 29. The TGA analysis of free base Formula I, MEK solvate form (after drying) is shown in FIG. 31. The material lost about 7.8% weight at 189° C. The DSC thermogram of free base Formula I, MEK solvate is shown in FIG. 30. The melting onset is about 71.3° C.

Formula I, MeTHF Solvate

Formula I, MeTHF solvate was first obtained as follows: a solution containing about 200 mg of free base Formula I in 1 mL 2-methyltetrahydrofuran was stirred at about 22° C. overnight, then 70° C. for 1 day, and at about 22° C. for another day. The resulting composition was a thick slurry, and was filtered, dried in the vacuum oven at 50° C.

Alternatively, Formula I, MeTHF solvate can be obtained through the following method: 20 g of amorphous Formula I was dissolved in 60 mL 2-methyltetrahydrofuran at 20° C., stirred at for 1 h to form a slurry. To the slurry was added 40 mL n-heptane over 2 h. The slurry was filtered, washed with 40 mL heptane, and dried in the vacuum oven at 50° C. for 2 h.

The XRPD pattern of darunavir Formula I, MeTHF solvate is shown in FIG. 32. The TGA analysis of free base Formula I, MeTHF solvate is shown in FIG. 34. The material lost about 12.5% weight at 200° C. The DSC thermogram of Formula I, MeTHF solvate is shown in FIG. 33. The melting onset for Formula I, MeTHF solvate is about 85.5° C.

Solvated Darunavir (Formula I, MeOAc Solvate)

Formula I methyl acetate (MeOAc) solvate was first obtained as follows: 1 g of amorphous Formula I was dissolved in 5 mL of methyl acetate at room temperature. To the solution 1.5 mL of n-heptane was added and the mixture was sonicated for 15 seconds to form slurry, to which an additional 1.5 mL of n-heptane was added. The resulting solids were filtered and dried under vacuum at about 20° C.

Alternatively, Formula I, methyl acetate solvate can also be prepared as follows: 12 g of free base Formula I was dissolved in 60 mL of methyl acetate at 40° C. to afford a clear solution. The solution was cooled to room temperature (22° C.), followed by addition of 18 mL of n-heptane. The solution was seeded (optional) with seeds obtained from above. An additional 42 mL of n-heptane was added to complete the crystallization. Crystalline methyl acetate solvate was filtered and dried in the vacuum oven at room temperature.

The XRPD pattern of Formula I methyl acetate is shown in FIG. 35. Single crystal was successfully grown from methyl acetate and n-heptane using procedure similar to the process described above. Structure elucidation indicates it is a API:solvent=1:1 channel solvate with methyl acetate residing in the void space within the crystal structure. The simulated XRPD pattern (based on single crystal structure) is matching well with the experimental XRPD pattern (FIG. 35). Due to the channel solvate nature of the crystals and the relatively low boiling point, methyl acetate is prone to escape from the crystal structure upon drying. The TGA analysis of free base Formula I, methyl acetate solvate, upon drying at 50° C. under vacuum, is shown in FIG. 37. The material lost about 7.6% weight at 200° C. $^1$H NMR analysis of the same sample indicates 0.6 equivalent of methyl acetate in the sample. Despite the deficiency of methyl acetate based on TGA and $^1$H NMR results, the crystal structure remains mostly intact with similar XRPD patterns. The DSC thermogram of free base Formula I, methyl acetate solvate form is shown in FIG. 36. The convoluted melting/desolvation endotherm has an onset about 74.8° C.

Formula I, Ethyl Formate Solvate

Formula I, ethyl formate solvate was prepared as follows: 1 g of amorphous free base Formula I was dissolved in 5 mL of ethyl formate at room temperature. To the solution 1.5 mL of n-heptane was added and the mixture was sonicated for 15 seconds to form a slurry. An additional 0.5 mL of n-heptane was added, and the mixture was sonicated for another 30 seconds. A final charge of 1 mL of n-heptane was followed by 1 minute of sonication and the resulting solid was filtered and dried under vacuum at room temperature.

Alternatively Formula I ethyl formate solvate can be prepared as follows: 12 g of free base Formula I was dissolved in 60 mL of ethyl formate at 40° C. to give a clear solution. The solution was cooled to room temperature (22° C.), followed by addition of 18 mL of n-heptane. The solution was seeded (optional) with seeds obtained from above. An additional 42 mL of n-heptane was added to the mixture over 6 hours to complete the crystallization. Crystalline Formula I, ethyl formate solvate form was filtered and dried in the vacuum oven at room temperature.

Single crystal was successfully grown from ethyl formate and n-heptane using procedure similar to the process described above. Structure elucidation indicates it is a API:solvent=1:1 channel solvate with ethyl formate residing in the void space within the crystal structure. The simulated XRPD pattern (based on single crystal structure) is matching well with the experimental XRPD pattern as shown in FIG. 38.

Due to the channel solvate nature of the crystal and the relatively low boiling point, ethyl formate is prone to escape from the crystal structure upon drying. The TGA analysis of Formula I, ethyl formate solvate, upon drying at 50° C. under vacuum, is shown in FIG. 40. The material lost about 8.2% weight at 200° C.

$^1$H NMR analysis of Formula I, ethyl formate solvate form, indicated 0.6 equivalent of ethyl formate in the sample. Despite the deficiency of ethyl formate based on TGA and $^1$H NMR results, the crystal structure remains mostly intact with similar XRPD patterns (FIG. 38). The DSC thermogram of Formula I ethyl formate solvate is shown in FIG. 39. The convoluted desolvation/melting endotherm has an onset at about 75.5° C.

The crystalline forms of the present invention were characterized by various analytical techniques, including X-ray powder diffraction (XRPD), differential scanning calorimetry (DSC), thermogravimetric analysis (TGA), and dynamic vapor sorption (DVS) using the procedures described below.

X-Ray Powder Diffraction:

XRPD analysis was conducted on a diffractometer (PANanalytical XPERT-PRO, PANanalytical B.V., Almelo, Netherlands) using copper radiation (Cu Kα, λ=1.5406 Å). Samples were prepared for analysis by depositing the powdered sample in the center of a steel holder equipped with a zero background plate. The generator was operated at a voltage of 45 kV and amperage of 40 mA. Slits used were Soller 0.02 rad., antiscatter 1.0°, and divergence. The sample rotation speed was 2 revolutions/second. Scans were performed from 2 to 40° 2θ during 5 min with a step size of 0.0084 to 0.0167° 2θ. Data analysis was performed by X'Pert Date Viewer version 2.2c (PANalytical B.V., Almelo, Netherlands) and X'Pert data viewer version 1.2d (PANalytical B.V., Almelo, Netherlands).

The XRPD pattern for Formula I Form I is represented in FIG. 1.

The XRPD pattern for Formula I Hydrate I is represented in FIG. 5.

The XRPD pattern for Formula I Acetic Acid Solvate I is represented in FIG. 8.

The XRPD pattern for Formula I Esylate I is represented in FIG. 11.

The XRPD pattern for Formula I Besylate I is represented in FIG. 15.

The XRPD pattern for Formula I Hemisulfate I is represented in FIG. 18.

The XRPD pattern for Formula I Napsylate I is represented in FIG. 20.

The XRPD pattern for Formula I Hemiedisylate I is represented in FIG. 22.

The XRPD pattern for Formula I Tosylate I is represented in FIG. 24.

The XRPD pattern for Formula I, Material A is represented in FIG. 26.

The XRPD pattern for Formula I, MEK solvate is represented in FIG. 29.

The XRPD pattern for Formula I, MeTHF solvate is represented in FIG. 32.

The XRPD pattern for Formula I, MeOAc solvate is represented in FIG. 35.

The XRPD pattern for Formula I, ethyl formate solvate is represented in FIG. 38.

Differential Scanning Calorimetry:

Thermal properties were evaluated using a Differential Scanning calorimetry (DSC) instrument (TA Q2000, TA Instruments, New Castle, Del., USA). Approximately 1 to 5 mg of solid sample was placed in a standard aluminum pan vented with a pinhole for each experiment and heated at a rate of about 10° C/min under a 50 mL/min nitrogen purge. Data analysis was conducted using Universal Analysis 2000 Version 4.7A (TA Instruments, New Castle, Del., USA).

The DSC for Formula I Form I is represented in FIG. 2.

The DSC for Formula I Hydrate I is represented in FIGS. 6a and 6b.

The DSC for Formula I Acetic Acid Solvate I is represented in FIG. 9.

The DSC for Formula I Esylate I is represented in FIG. 12.

The DSC for Formula I Besylate I is represented in FIG. 16.

The DSC for Formula I Hemisulfate I is represented in FIG. 19.

The DSC for Formula I Napsylate I is represented in FIG. 21.

The DSC for Formula I Hemiedisylate I is represented in FIG. 23.

The DSC for Formula I Tosylate I is represented in FIG. 25.

The DSC for Formula I, Material A is represented in FIG. 27.

The DSC for Formula I, MEK solvate form is represented in FIG. 30.

The DSC for Formula I, MeTHF solvate form is represented in FIG. 33.

The DSC for Formula I, MeOAc solvate form is represented in FIG. 36.

The DSC for Formula I, ethyl formate solvate form is represented in FIG. 39.

Thermogravimetric Analysis:

Thermogravimetric analysis (TGA) was performed on a TGA instrument (TA Q5000, TA Instruments, New Castle, Del., USA). Approximately 1 to 5 mg of solid sample was placed in an open aluminum pan for each experiment and heated at a rate of about 10° C./min under a 25 mL/min nitrogen purge using. Data analysis was conducted using Universal Analysis 2000 Version 4.7A (TA Instruments, New Castle, Del., USA).

The TGA for Formula I Form I is represented in FIG. 3.

The TGA for Formula I Hydrate I is represented in FIG. 7.

The TGA for Formula I Acetic Acid Solvate I is represented in FIG. 10.

The TGA for Formula I Esylate I is represented in FIG. 13.

The TGA for Formula I Besylate I is represented in FIG. 17.

The TGA for Formula I, Material A is represented in FIG. 28.

The TGA for Formula I, MEK solvate form is represented in FIG. 31.

The TGA for Formula I, MeTHF solvate form is represented in FIG. 34.

The TGA for Formula I, MeOAc solvate form is represented in FIG. 37.

The TGA for Formula I, ethyl formate solvate form is represented in FIG. 40.

Dynamic Vapor Sorption:

The hygroscopicity was evaluated at room temperature using a dynamic vapor sorption (DVS) instrument (TGA Q5000 TA Instruments, New Castle, Del.). Water adsorption and desorption were studied as a function of relative humidity (RH) over the range of 0 to 90% at 25° C. The relative humidity in the chamber was increased by 10% RH and held until the solid and atmosphere reached equilibration. The equilibrium test was continued until passed or expired after 5 or 10 hours. At this point, RH was raised 10% higher and the process was repeated until 90% RH was reached and equilibrated. During this period, the water sorption was monitored. For desorption, the relative humidity was decreased in a similar manner to measure a full sorption/desorption cycle. The cycle was optionally repeated. All experiments were operated in dm/dt mode (mass variation over time) to determine the equilibration endpoint. Approximately 5-10 mg of solid was used. Data analysis was conducted using Universal Analysis 2000 Version 4.7A (TA Instruments, New Castle, Del., USA).

The DVS for Formula I Form I is represented in FIG. 4.

The DVS for Formula I Esylate I is represented in FIG. 14.

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A crystalline form of darunavir, wherein the crystalline form is Form I characterized by an X-ray powder diffraction (XRPD) pattern having peaks at about 7.2°, 17.8°, and 25.1° 2-θ±0.2° 2-θ.

2. The crystalline form of claim 1, wherein the X-ray powder diffraction (XRPD) pattern has further peaks at about 10.8°, 14.3° and 18.3° 2-θ±0.2° 2-θ.

3. The crystalline form of claim 1, characterized by an X-ray powder diffraction (XRPD) pattern substantially as set forth in FIG. 1.

4. The crystalline form of claim 1, characterized by differential scanning calorimetry (DSC) pattern substantially as set forth in FIG. 2.

5. The crystalline form of claim 1, characterized by thermogravimetric analysis (TGA) pattern substantially as set forth in FIG. 3.

6. The crystalline form of claim 1, characterized by a dynamic vapor sorption (DVS) pattern substantially as set forth in FIG. 4.

7. A pharmaceutical composition comprising a therapeutically effective amount of the crystalline form of darunavir of claim 1 and a pharmaceutically acceptable excipient.

8. The pharmaceutical composition of claim 7, further comprising one to three additional therapeutic agents.

9. The pharmaceutical composition of claim 8, wherein the additional therapeutic agents are each active against HIV.

10. The pharmaceutical composition of claim 7, wherein the pharmaceutical composition is in a unit dosage form.

11. The pharmaceutical composition of claim 10, wherein the unit dosage form is a tablet.

12. A pharmaceutical composition prepared by combining a therapeutically effective amount of the crystalline form of darunavir of claim 1 with a pharmaceutically acceptable excipient.

13. A method of treating a virus infection caused by HIV in a human, the method comprising administering to a human in need thereof a therapeutically effective amount of the crystalline form of darunavir of claim 1.

* * * * *